US008017582B2

(12) United States Patent
Shirwan et al.

(10) Patent No.: US 8,017,582 B2
(45) Date of Patent: *Sep. 13, 2011

(54) IMMUNOSTIMULATORY COMPOSITIONS AND METHODS

(75) Inventors: Haval Shirwan, Louisville, KY (US);
Kutlu G. Elpek, Louisville, KY (US);
Esma S. Yolcu, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/553,770

(22) Filed: Sep. 3, 2009

(65) Prior Publication Data

US 2010/0158936 A1 Jun. 24, 2010

Related U.S. Application Data

(62) Division of application No. 11/635,066, filed on Dec. 7, 2006, now Pat. No. 7,598,345.

(60) Provisional application No. 60/863,173, filed on Oct. 27, 2006, provisional application No. 60/799,643, filed on May 12, 2006, provisional application No. 60/771,179, filed on Feb. 6, 2006, provisional application No. 60/748,177, filed on Dec. 8, 2005.

(51) Int. Cl.
*A61K 38/16* (2006.01)
(52) U.S. Cl. .................................................. 514/21.2
(58) Field of Classification Search .................. None
See application file for complete search history.

(56) References Cited

U.S. PATENT DOCUMENTS

| 6,232,088 | B1 | 5/2001 | Franklin et al. |
|---|---|---|---|
| 7,238,360 | B2 | 7/2007 | Shirwan |
| 7,598,345 | B2 | 10/2009 | Shirwan et al. |
| 7,622,444 | B2 | 11/2009 | Weinberg |
| 7,745,215 | B2 | 6/2010 | Shirwan et al. |
| 2006/0052295 | A1 | 3/2006 | Terman |
| 2007/0172504 | A1 | 7/2007 | Shirwan et al. |
| 2007/0172947 | A1 | 7/2007 | Shirwan et al. |
| 2010/0240585 | A1 | 9/2010 | Shirwan et al. |

FOREIGN PATENT DOCUMENTS

| EP | 1 736 482 A1 | 12/2006 |
|---|---|---|
| WO | WO 00/67788 A2 | 11/2000 |
| WO | WO 02/02751 | 1/2002 |
| WO | WO 2007/000675 A2 | 1/2007 |

OTHER PUBLICATIONS

U.S. Appl. No. 12/823,430, filed Jun. 25, 2010, Shirwan et al.
Notice of Allowance issued on Jan. 27, 2010 by the Examiner in U.S. Appl. No. 11/635,087 (US 7,745,215).
Office Action issued on Aug. 20, 2010 by the Examiner in U.S. Appl. No. 12/499,488 (US 2010/0240585).
Zheng et al., "Induction of Antitumor Immunity via Intratumoral Tetra-Costimulator Protein Transfer," *Cancer Research*, vol. 61, pp. 8127-8134, Nov. 15, 2001.
U.S. Appl. No. 12/499,488, filed Jul. 8, 2009, Shirwan et al.
Lynch, "The promise of 4-1BB (D137)-mediated immunomodulation and the immunotherapy of cancer," *Immunological Reviews*, 2008, 222:277-286.
Boon et al., "Human T Cell Responses Against Melanoma," *Annu. Rev. Immunol.*, 2006, 24:175-208.
Nielson et al., "Melanoma vaccines: the paradox of T Cell activation without clinical response," *Cancer Chemother. Pharmacol.*, 2000, 46 (Suppl.): S62-S66.
Lee et al., "Increased Vaccine-Specific T Cell Frequency After Peptide-Based Vaccination Correlates with Increased Susceptibility to In Vitro Sitmulation But Does Not Lead to Tumor Regression," *J. Immunol.*, 1999, 163:6292-6300.
Blazer et al., "Infusuion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," *J. Immunol.*, 1996, 157:3250-3259.
Melero et al., "Amplification of tumor immunity by gene transfer of the co-stimulatory 4-1BB ligand: synergy with the CD28 co-stimulatory pathway," *Eur. J. Immnol.*, 1998, 28:1116-1121.
International Search Report issued in application No. PCT/US2006/046662 (corresponding to US 2007/0172947), mailed Nov. 13, 2007.
Office Action dated Dec. 4, 2007, issued by the Examiner in U.S. Appl. No. 11/635,087 (US 2007/0172947).
Office Action dated Apr. 30, 2008, issued by the Examiner in U.S. Appl. No. 11/635,087 (US 2007/0172947).
Office Action dated Jan. 16, 2009, issued by the Examiner in U.S. Appl. No. 11/635,087 (US 2007/0172947).
Office Action dated Jan. 9, 2009, issued by the Examiner in U.S. Appl. No. 11/635,075 (US 2007/0172504).
Office Action dated Apr. 17, 2008, issued by the Examiner in U.S. Appl. No. 11/635,075 (US 2007/0172504).
Office Action dated Dec. 4, 2007, issued by the Examiner in U.S. Appl. No. 11/635,075 (US 2007/0172504).
International Search Report issued in application No. PCT/US2006/046663 (corresponding to US 2007/0172504), mailed Sep. 21, 2007.
Asai, T. et al., "A human biotin acceptor domain allows site-specific conjugation o fan enzyme to an antibody-avidin fusion protein for targeted drug delivery", Biomolecular Engineering, vol. 21, No. 6, pp. 145-155 (2005).
Huang, T-H, "Improved immunogenicity of a self-tumor antigen by covalent linkage to CD40 ligand", Intl J. Cancer, vol. 108, pp. 696-703 (2004).

(Continued)

*Primary Examiner* — Ilia Ouspenski
(74) *Attorney, Agent, or Firm* — Foley & Lardner LLP

(57) ABSTRACT

The invention provides conjugates comprising an immune co-stimulatory polypeptide and an antigen or infectious agent. The conjugates are useful for generating or enhancing an immune response against the antigen or infectious agent. The invention also provides immune cells modified with a conjugate that are useful for generating or enhancing an immune response to an antigen or infectious agent. The invention also provides immunostimulatory moieties comprising an immune co-stimulatory polypeptide that are useful for stimulating an immune response. The invention also provides immunotherapy methods and methods of treating or preventing infections.

17 Claims, 33 Drawing Sheets

OTHER PUBLICATIONS

Huang, T-H, et al., "Enhanced antitumor immunity by fusion of CTLA-4 to a self tumor antigen", Blood, vol. 96, No. 12, pp. 3663-3670 (2000).

Rohrbach, F., et al., "Targeted delivery of the ErbB2/HER2 tumor antigen to professional APCs results in effective antitumor immunity", J. Immuno., vol. 174, No. 9, pp. 5481-5489 (2005).

Askenasy, Nadir et al., "Display of Fas Ligand Protein on Cardiac Vasculature as a Novel Means of Regulating Allograft Rejection", *Circulation*, vol. 107, No. 11, pp. 1525-1531 (2003).

Briones, Javier et al., "Antitumor Immunity After Vaccination With B Lymphoma Cells Overexpressing a Triad of Costimulatory Molecules", *Journal of the National Cancer Institute*, vol. 95, No. 7, pp. 548-555 (2003).

Kilinc, Mehmet O. et al., "Generation of a multimeric form of CD40L with potent immunostimulatory activity using streptavidin as a chaperon", *Experimental and Molecular Pathology*, vol. 80, No. 3, pp. 252-261 (2006).

Hodge, James W. et al., "A Triad of Costimulatory Molecules Synergize to Amplify T-Cell Activation", *Cancer Research*, vol. 59, pp. 5800-5807 (1999).

Singh, Narendra P. et al., "A Novel Approach to Cancer Immunotherapy: Tumor Cells Decorated with CD80 Generate Effective Antitumor Immunity", *Cancer Research*, vol. 63, No. 14, pp. 4067-4073 (2003).

Singh, Narendra P. et al., "ProtEx™: A Novel Technology to Display Exogenous Proteins on the Cell Surface for Immunomodulation", *Ann. N.Y. Acad. Sci.*, vol. 1056, pp. 344-358 (2005).

Singh, Narendra P. et al., "Primary Tumor Cells Resected from Cancer Patients and Decorated with a Novel Form of CD80 Protein Serve as Effective Antigen-Presenting Cells for the Induction of Autologous T Cell Immune Responses Ex Vivo", *Human Gene Therapy*, vol. 17, No. 3, pp. 334-346 (2006).

Yolcu, Esma S. et al., "Cell Membrane Modification for Rapid Display of Proteins as a novel Means of Immunomodulation: FasL-Decorated Cells Prevent Islet Graft Rejection", *Immunity*, 17:795-808 (2002).

Moro, Monica et al., "Induction of Therapeutic T-Cell Immunity by tumor Targeting with Soluble Recombinant B7-Immunoglobulin Costimulatory Molecules", *Cancer Research*, vol. 59, No. 11, pp. 2650-2656 (1999).

Symington, Frank W. et al., "Expression and Function of B7 on Human Epidermal Langerhans Cells", *Journal of Immunology*, vol. 150, No. 4, pp. 1286-1295 (1993).

Kudo-Saito, Chie et al., "Intratumoral Vaccination and Diversified Subcutaneous/Intratumoral Vaccination with Recombinant Poxviruses Costimulatory Molecules", *Clincal Cancer Research*, vol. 10, No. 3, pp. 1090-1099 (2004).

De Jong, Marg O. et al., "Biotinylation of interleukin-s (IL-2) for flow cytometric analysis of IL-2 receptor expression", *J. Immunol. Methods*, 184:101-112 (1995).

Jordan, Robert A. et al., "Production of Genetically Engineered Biotinylated Interleukin-s and Its Applications in a Rapid Nonradioactive Assay for T-Cell Activation", *Clin.Diag. Lab. Immunol.*, vol. 10, No. 3, pp. 339-344 (2003).

Notice of Allowance issued on Jun. 5, 2009, by the Examiner in U.S. Appl. No. 11/635,066 (US 7,598,345).

Office Action issued on Feb. 24, 2009, by the Examiner in U.S. Appl. No. 11/635,066 (US 7,598,345).

Office Action issued on Apr. 21, 2008, by the Examiner in U.S. Appl. No. 11/635,066 (US 7,598,345).

Office Action issued on Dec. 4, 2007, by the Examiner in U.S. Appl. No. 11/635,066 (US 7,598,345).

Notice of Allowance issued on Sep. 10, 2009, by the Examiner in U.S. Appl. No. 11/635,087 (US 2007-0172947).

International Search Report issued on Feb. 14, 2008, in application No. PCT/US2006/046664 (corresponding to US 7,598,345).

Rabu et al., "Production of Recombinant Human Trimeric CD137L (4-1BBL): Cross-Linking is Essential to its T Cell Co-Stimulation Activity," *The Journal of Biological Chemistry*, vol. 280, No. 50, pp. 41472-41481 (Dec. 16, 2005).

Office Action issued on Jan. 20, 2011 by the Examiner in U.S. Appl. No. 12/499,488 (US 2010/0240585).

FIGURE 1A

CSA-LIGHT Nucleotide Construct (SEQ ID NO:1)

ACCCGTGTGTAAAGCCGCGTTTCCAAAATGTATAAAACCGAGAGCATCTGGCCAATG
TGCATCAGTTGTGGTCAGCAGCAAAATCAAGTGAATCATCTCAGTGCAACTAAAGGG
GGGATCCGATCTCAATATGAAGTTATGCATATTACTGGCCGTCGTGGCCTTTGTTGG
CCTCTCGCTCGGGAGATCTCATCATCACCATCACCATATCACCGGCACCTGGTACAA
CCAGCTCGGCTCGACCTTCATCGTGACCGCGGGCGCCGATGGCGCCCTGACCGGAAC
CTACGAGTCGGCCGTCGGCAACGCCGAGAGCCGCTACGTCCTGACCGGTCGTTACGA
CAGCGCCCCGGCCACCGACGGCAGCGGCACCGCCCTCGGTTGGACGGTGGCCTGGAA
GAATAACTACCGCAACGCCCACTCCGCGACCACGTGGAGCGGCCAGTACGTCGGCGG
CGCCGAGGCGAGGATCAACACCCAGTGGCTGCTGACCTCCGGCGCCACCGAGGCCAA
CGCCTGGAAGTCCACGCTGGTCGGCCACGACACCTTCACCAAGGTGAAGCCGTCCGC
CGCCTCAAGCGAATTCCAACGATCTCACCAGGCCAACCCAGCAGCACATCTTACAGG
AGCCAACGCCAGCTTGATAGGTATTGGTGGACCTCTGTTATGGGAGACACGACTTGG
CCTGGCCTTCTTGAGGGGCTTGACGTATCATGATGGGCCCTGGTGACCATGGAGCC
CGGTTACTACTATGTGTACTCCAAAGTGCAGCTGAGCGGCGTGGGCTGCCCCCAGGG
GCTGGCCAATGGCCTCCCCATCACCCATGGACTATACAAGCGCACATCCCGCTACCC
GAAGGAGTTAGAACTGCTGGTCAGTCGGCGGTCACCCTGTGGCCGGGCCAACAGCTC
CCGAGTCTGGTGGGACAGCAGCTTCCTGGGCGGCGTGGTACATCTGGAGGCTGGGGA
AGAGGTGGTGGTCCGCGTGCCTGGAAACCGCCTGGTCAGACCACGTGACGGCACCAG
GTCCTATTTCGGAGCTTTCATGGTCTGAAGGCTGCGGTGACAATGTATTTTGTGGAG
GGACCTCTCCAGGACTCACCCTCGAGTCTAGAGGGCCCTTCGAAGGTAAGCCTATCC
CTAACCCTCTCCTCGGTCTCGATTCTACGCGTACCGGTCATCATCACCATCACCATT
GAGTTTAAACCCGCTG

FIGURE 1B

CSA-LIGHT Fusion Protein (SEQ ID NO:2)

MKLCILLAVVAFVGLSLGRSHHHHHH<u>ITGTWYNQLGSTFIVTAGADGALTGTYESAV
GNAESRYVLTGRYDSAPATDGSGTALGWTVAWKNNYRNAHSATTWSGQYVGGAEARI
NTQWLLTSGATEANAWKSTLVGHDTFTKVKPSAAS</u>SEFQRSHQANPAAHLTGANASL
IGIGGPLLWETRLGLAFLRGLTYHDGALVTMEPGYYYVYSKVQLSGVGCPQGLANGL
PITHGLYKRTSRYPKELELLVSRRSPCGRANSSRVWWDSSFLGGVVHLEAGEEVVVR
VPGNRLVRPRDGTRSYFGAFMV

FIGURE 2A

CD80-CSA Nucleotide Construct (SEQ ID NO:3)

CATCTCCAGTGCAACTAAAGGGGGGATCCGATCTCAATATGAAGTTATGC
ATATTACTGGCCGTCGTGGCCTTTGTTGGCCTCTCGCTCGGGAGATCTAT
CCACGTGACCAAGGAAGTGAAAGAAGTGGCAACGCTGTCCTGTGGTCACA
ATGTTTCTGTTGAAGAGCTGGCACAAACTCGCATCTACTGGCAAAAGGAG
AAGAAAATGGTGCTGACTATGATGTCTGGGGACATGAATATATGGCCCGA
GTACAAGAACCGGACCATCTTTGATATCACTAATAACCTCTCCATTGTGA
TCCTGGCTCTGCGCCCATCTGACGAGGGCACATACGAGTGTGTTGTTCTG
AAGTATGAAAAAGACGCTTTCAAGCGGGAACACCTGGCTGAAGTGACGTT
ATCAGTCAAAGCTGACTTCCCTACACCTAGTATATCTGACTTTGAAATTC
CAACTTCTAATATTAGAAGGATAATTTGCTCAACCTCTGGAGGTTTTCCA
GAGCCTCACCTCTCCTGGTTGGAAAATGGAGAAGAATTAAATGCCATCAA
CACAACAGTTTCCCAAGATCCTGAAACTGAGCTCTATGCTGTTAGCAGCA
AACTGGATTTCAATATGACAACCAACCACAGCTTCATGTGTCTCATCAAG
TATGGACATTTAAGAGTGAATCAGACCTTCAACTGGAATACAACCAAGCA
AGAGAGATCTCATCATCACCATCACCATATCACCGGCACCTGGTACAACC
AGCTCGGCTCGACCTTCATCGTGACCGCGGGCGCCGACGGCGCCCTGACC
GGAACCTACGAGTCGGCCGTCGGCAACGCCGAGAGCCGCTACGTCCTGAC
CGGTCGTTACGACAGCGCCCCGGCCACCGACGGCAGCGGCACCGCCCTCG
GTTGGACGGTGGCCTGGAAGAATAACTACCGCAACGCCCACTCCGCGACC
ACGTGGAGCGGCCAGTACGTCGGCGGCGCCGAGGCGAGGATCAACACCCA
GTGGCTGTTGACCTCCGGCGCCACCGAGGCCAACGCCTGGAAGTCCACGC
TGGTCGGCCACGACACCTTCACCAAGGTGAAGCCGTCCGCCGCCTCAAGC
CGAATTCTGCAGATATCCAGCACAGTGGCGGCCGCTCGAGTCTAGAGGGC
CCTTCGAAGGTAAGCCTATCCCTAACCCTCTCCTCGGTCTCGATTCTACG
CGTACCGGTCATCATCACCATCACCATTGAGTTTAAACCCGCTGATCAGC
CTCGACTGTGCTTTCTAA

FIGURE 2B

CD80-CSA Fusion Protein (SEQ ID NO:4)

CSA-4-1BBL Nucleotide Construct (SEQ ID NO:5)

TTCATGCAACTAAAGGGGGGATCCGATCTCAATATGAAGTTATGCATATT
ACTGGCCGTCGTGGCCTTTGTTGGCCTCTCGCTCGGGAGATCTCATCATC
ACCATCACCATATCACCGGCACCTGGTACAACCAGCTCGGCTCGACCTTC
ATCGTGACCGCGGGCGCCGATGGCGCCCTGACCGGAACCTACGAGTCGGC
CGTCGGCAACGCCGAGAGCCGCTACGTCCTGACCGGTCGTTACGACAGCG
CCCCGGCCACCGACGGCAGCGGCACCGCCCTCGGTTGGACGGTGGCCTGG
AAGAATAACTACCGCAACGCCCACTCCGCGACCACGTGGAGCGGCCAGTA
CGTCGGCGGCGCCGAGGCGAGGATCAACACCCAGTGGCTGTTGACCTCCG
GCGCCACCGAGGCCAACGCCTGGAAGTCCACGCTGGTCGGCCACGACACC
TTCACCAAGGTGAAGCCGTCCGCCGCCTCAAGCGAATTCCGCACCGAGCC
TCGGCCAGCGCTCACAATCACCACCTCGCCCAACCTGGGTACCCGAGAGA
ATAATGCAGACCAGGTCACCCCTGTTTCCCACATTGGCTGCCCCAACACT
ACACAACAGGGCTCTCCTGTGTTCGCCAAGCTACTGGCTAAAAACCAAGC
ATCGTTGTGCAATACAACTCTGAACTGGCACAGCCAAGATGGAGCTGGGA
GCTCATACCTATCTCAAGGTCTGAGGTACGAAGAAGACAAAAAGGAGTTG
GTGGTAGACAGTCCCGGGCTCTACTACGTATTTTTGGAACTGAAGCTCAG
TCCAACATTCACAAACACAGGCCACAAGGTGCAGGGCTGGGTCTCTCTTG
TTTTGCAAGCAAAGCCTCAGGTAGATGACTTTGACAACTTGGCCCTGACA
GTGGAACTGTTCCCTTGCTCCATGGAGAACAAGTTAGTGGACCGTTCCTG
GAGTCAACTGTTGCTCCTGAAGGCTGGCCACCGCCTCAGTGTGGGTCTGA
GGGCTTATCTGCATGGAGCCCAGGATGCATACAGAGACTGGGAGCTGTCT
TATCCCAACACCACCAGCTTTGGACTCTTTCTTGTGAAACCCGACAACCC
ATGGGAATGAGAACTATCCTTCTTGTGACTCCTAGTTGCTAAGTCCTCAA
GCTGCTATGCTCGAGTCTAGAGGGCCCTTCGAAGGTAAGCCTATCCCTAA
CCCTCTCCTCGGTCTCGATTCTACGCGTACCGGTCATCATCACCATCACC
ATTGAGTTTAAACCCGCTGATCAGCCTCGACTGTGCCTTTCTAA

FIGURE 3B

CSA-murine 4-1BBL Fusion Protein (SEQ ID NO:6)

CSA-human 4-1BBL Nucleotide Sequence (SEQ ID NO:7)

```
TTCATGCAACTAAAGGGGGGATCCGATCTCAATATGAAGTTATGCATATTACTGGCC
GTCGTGGCCTTTGTTGGCCTCTCGCTCGGGAGATCTCATCATCACCATCACCATATC
ACCGGCACCTGGTACAACCAGCTCGGCTCGACCTTCATCGTGACCGCGGGCGCCGAT
GGCGCCCTGACCGGAACCTACGAGTCGGCCGTCGGCAACGCCGAGAGCCGCTACGTC
CTGACCGGTCGTTACGACAGCGCCCCGGCCACCGACGGCAGCGGCACCGCCCTCGGT
TGGACGGTGGCCTGGAAGAATAACTACCGCAACGCCCACTCCGCGACCACGTGGAGC
GGCCAGTACGTCGGCGGCGCCGAGGCGAGGATCAACACCCAGTGGCTGTTGACCTCC
GGCGCCACCGAGGCCAACGCCTGGAAGTCCACGCTGGTCGGCCACGACACCTTCACC
AAGGTGAAGCCGTCCGCCGCCTCAAGCGAATTCGCCTGCCCCTGGGCCGTGTCCGGG
GCTCGCGCCTCGCCCGGCTCCGCGGCCAGCCCGAGACTCCGCGAGGGTCCCGAGCTT
TCGCCCGACGATCCCGCCGGCCTCTTGGACCTGCGGCAGGGCATGTTTGCGCAGCTG
GTGGCCCAAAATGTTCTGCTGATCGATGGGCCCCTGAGCTGGTACAGTGACCCAGGC
CTGGCAGGCGTGTCCCTGACGGGGGGCCTGAGCTACAAAGAGGACACGAAGGAGCTG
GTGGTGGCCAAGGCTGGAGTCTACTATGTCTTCTTTCAACTAGAGCTGCGGCGCGTG
GTGGCCGGCGAGGGCTCAGGCTCCGTTTCACTTGCGCTGCACCTGCAGCCACTGCGC
TCTGCTGCTGGGGCCGCCGCCCTGGCTTTGACCGTGGACCTGCCACCCGCCTCCTCC
GAGGCTCGGAACTCGGCCTTCGGTTTCCAGGGCCGCTTGCTGCACCTGAGTGCCGGC
CAGCGCCTGGGCGTCCATCTTCACACTGAGGCCAGGGCACGCCATGCCTGGCAGCTT
ACCCAGGGCGCCACAGTCTTGGGACTCTTCCGGGTGACCCCCGAAATCCCAGCCGGA
CTCCCTTCACCGAGGTCGGAATAACGCCCAGCCTGGGTGCAGCCCACCTGGACAGAG
TCCGAATCCTACTCCATCCTCTCGAGTCTAGAGGGCCCTTCGAAGGTAAGCCTATCC
CTAACCCTCTCCTCGGTCTCGATTCTACGCGTACCGGTCATCATCACCATCACCATT
GAGTTTAAACCCGCTGATCAGCCTCGACTGTGCCTTTCTAA
```

FIGURE 4B

CSA-human 4-1BBL Fusion Protein (SEQ ID NO:8)

MKLCILLAVVAFVGLSLGRSHHHHHH<u>ITGTWYNQLGSTFIVTAGADGALTGTYESAV
GNAESRYVLTGRYDSAPATDGSGTALGWTVAWKNNYRNAHSATTWSGQYVGGAEARI
NTQWLLTSGATEANAWKSTLVGHDTFTKVKPSAASS</u>EFACPWAVSGARASPGSAASP
RLREGPELSPDDPAGLLDLRQGMFAQLVAQNVLLIDGPLSWYSDPGLAGVSLTGGLS
YKEDTKELVVAKAGVYYVFFQLELRRVVAGEGSGSVSLALHLQPLRSAAGAAALALT
VDLPPASSEARNSAFGFQGRLLHLSAGQRLGVHLHTEARARHAWQLTQGATVLGLFR
VTPEIPAGLPSPRSE

FIGURE 5A

CD86-CSA Nucleotide Construct (SEQ ID NO:9)

CATCTCCAGTGCAACTAAAGGGGGGATCCGATCTCAATATGAAGTTATGCATATTAC
TGGCCGTCGTGGCCTTTGTTGGCCTCTCGCTCGGGAGATCTGCTCCTCTGAAGATTC
AAGCTTATTTCAATGAGACTGCAGACCTGCCATGCCAATTTGCAAACTCTCAAAACC
AAAGCCTGAGTGAGCTAGTAGTATTTTGGCAGGACCAGGAAAACTTGGTTCTGAATG
AGGTATACTTAGGCAAAGAGAAATTTGACAGTGTTCATTCCAAGTATATGGGCCGCA
CAAGTTTTGATTCGGACAGTTGGACCCTGAGACTTCACAATCTTCAGATCAAGGACA
AGGGCTTGTATCAATGTATCATCCATCACAAAAAGCCCACAGGAATGATTCGCATCC
ACCAGATGAATTCTGAACTGTCAGTGCTTGCTAACTTCAGTCAACCTGAAATAGTAC
CAATTTCTAATATAACAGAAAATGTGTACATAAATTTGACCTGCTCATCTATACACG
GTTACCCAGAACCTAAGAAGATGAGTGTTTTGCTAAGAACCAAGAATTCAACTATCG
AGTATGATGGTATTATGCAGAAATCTCAAGATAATGTCACAGAACTGTACGACGTTT
CCATCAGCTTGTCTGTTTCATTCCCTGATGTTACGAGCAATATGACCATCTTCTGTA
TTCTGGAAACTGACAAGACGCGGCTTTTATCTTCACCTTTCTCTATAGAGCTTGAGG
ACCCTCAGCCTCCCCCAGACCACATTCCTAGATCTCATCATCACCATCACCATATCA
CCGGCACCTGGTACAACCAGCTCGGCTCGACCTTCATCGTGACCGCGGGCGCCGACG
GCGCCCTGACCGGAACCTACGAGTCGGCCGTCGGCAACGCCGAGAGCCGCTACGTCC
TGACCGGTCGTTACGACAGCGCCCCGGCCACCGACGGCAGCGGCACCGCCCTCGGTT
GGACGGTGGCCTGGAAGAATAACTACCGCAACGCCCACTCCGCGACCACGTGGAGCG
GCCAGTACGTCGGCGGCGCCGAGGCGAGGATCAACACCCAGTGGCTGTTGACCTCCG
GCGCCACCGAGGCCAACGCCTGGAAGTCCACGCTGGTCGGCCACGACACCTTCACCA
AGGTGAAGCCGTCCGCCGCCTCAAGCCGAATTCTGCAGATATCCAGCACAGTGGCGG
CCGCTCGAGTCTAGAGGGCCCTTCGAAGGTAAGCCTATCCCTAACCCTCTCCTCGGT
CTCGATTCTACGCGTACCGGTCATCATCACCATCACCATTGAGTTTAAACCCGCTGA
TCAGCCTCGACTGTGCTTTCTAA

FIGURE 5B

CD86-CSA Fusion Protein (SEQ ID NO:10)

MKLCILLAVVAFVGLSLGRSAPLKIQAYFNETADLPCQFANSQNQSLSELVVFWQDQ
ENLVLNEVYLGKEKFDSVHSKYMGRTSFDSDWTLRLHNLQIKDKGLYQCIIHHKKP
TGMIRIHQMNSELSVLANFSQPEIVPISNITENVYINLTCSSIHGYPEPKKMSVLLR
TKNSTIEYDGIMQKSQDNVTELYDVSISLSVSFPDVTSNMTIFCILETDKTRLLSSP
FSIELEDPQPPPDHIPRSHHHHHH**ITGTWYNQLGSTFIVTAGADGALTGTYESAVGN
AESRYVLTGRYDSAPATDGSGTALGWTVAWKNNYRNAHSATTWSGQYVGGAEARINT
QWLLTSGATEANAWKSTLVGHDTFTKVKPSAASS**

FIGURE 6A

HPV16 E6 Amino Acid Sequence (SEQ ID NO:11)

MHQKRTAMFQDPQERPRKLPQLCTELQTTIHDIILECVYCKQQLLRREVYDFAFRDL
CIVYRDGNPYAVCDKCLKFYSKISEYRHYCYSLYGTTLEQQYNKPLCDLLIRCINCQ
KPLCPEEKQRHLDKKQRFHNIRGRWTGRCMSCCRSSRTRRETQL

FIGURE 6B

Variant HPV16 E6 Amino Acid Sequence (SEQ ID NO:12)

MFQDPQERPTKLPDLCTELQTTIHDIILECVYCKQQLLRREVYDFAFRDLCIVYRDG
NPYAVCDKCLKFYSKISEYRHYCYSLYGTTLEQQYNKPLCDLLIRCINGQKPLCPDE
KQRHLDKKQRFHNIRGRWTGRCMSCCRSSRTRRETQL

FIGURE 6C

HPV16 E7 Amino Acid Sequence (SEQ ID NO:13)

MHGDTPTLHEYMLDLQPETTDLYCYEQLNDSSEEEDEIDGPAGQAEPDRAHYNIVTF
CCKCDSTLRLCVQSTHVDIRTLEDLLMGTLGIVCPICSQKP

FIGURE 7A

CSA-hCD40L Nucleotide Construct (SEQ ID NO:14)

CCGATCTCAATATGAAGTTATGCATATTACTGGCCGTCGTGGCCTTTGTT
GGCCTCTCGCTCGGGAGATCTCATCATCACCATCACCATATCACCGGCAC
CTGGTACAACCAGCTCGGCTCGACCTTCATCGTGACCGCGGGCGCCGATG
GCGCCCTGACCGGAACCTACGAGTCGGCCGTCGGCAACGCCGAGAGCCGC
TACGTCCTGACCGGTCGTTACGACAGCGCCCCGGCCACCGACGGCAGCGG
CACCGCCCTCGGTTGGACGGTGGCCTGGAAGAATAACTACCGCAACGCCC
ACTCCGCGACCACGTGGAGCGGCCAGTACGTCGGCGGCGCCGAGGCGAGG
ATCAACACCCAGTGGCTGTTGACCTCCGGCGCCACCGAGGCCAACGCCTG
GAAGTCCACGCTGGTCGGCCACGACACCTTCACCAAGGTGAAGCCGTCCG
CCGCCTCAAGCGAATTCTTGGACAAGATAGAAGATGAAAGGAATCTTCAT
GAAGATTTTGTATTCATGAAAACGATACAGAGATGCAACACAGGAGAAAG
ATCCTTATCCTTACTGAACTGTGAGGAGATTAAAAGCCAGTTTGAAGGCT
TTGTGAAGGATATAATGTTAAACAAAGAGGAGACGAAGAAAGAAAACAGC
TTTGAAATGCAAAAAGGTGATCAGAATCCTCAAATTGCGGCACATGTCAT
AAGTGAGGCCAGCAGTAAAACAACATCTGTGTTACAGTGGGCTGAAAAAG
GATACTACACCATGAGCAACAACTTGGTAACCCTGGAAAATGGGAAACAG
CTGACCGTTAAAAGACAAGGACTCTATTATATCTATGCCCAAGTCACCTT
CTGTTCCAATCGGGAAGCTTCGAGTCAAGCTCCATTTATAGCCAGCCTCT
GCCTAAAGTCCCCCGGTAGATTCGAGAGAATCTTACTCAGAGCTGCAAAT
ACCCACAGTTCCGCCAAACCTTGCGGGCAACAATCCATTCACTTGGGAGG
AGTATTTGAATTGCAACCAGGTGCTTCGGTGTTTGTCAATGTGACTGATC
CAAGCCAAGTGAGCCATGGCACTGGCTTCACGTCCTTTGGCTTACTCAAA
CTCTGAACAGTGTCACCTTGCAGGAGCTCTAAGCCGAATTCTGCAGATAT
CCAGCACAGTGGCGGCCGCTCGAGTCTAGAGGGCCCTTCGAAGGTAAGCC
TATCCCTAACCCTCTCCTCGGTCTCGATTCTACGCGTACCGGTCATCATC
ACCATCACCATTGAGTTTAAACCCGCTGATCAGCCTCGACTGTGCCTTTC
TAA

FIGURE 7B

CSA-hCD40L Proten (SEQ ID NO:15)

```
M K L C I L L A V V A F V G L S L G R S H H H H H H I T G
T W Y N Q L G S T F I V T A G A D G A L T G T Y E S A V G
N A E S R Y V L T G R Y D S A P A T D G S G T A L G W T V
A W K N N Y R N A H S A T T W S G Q Y V G G A E A R I N T
Q W L L T S G A T E A N A W K S T L V G H D T F T K V K P
S A A S S E F L D K I E D E R N L H E D F V F M K T I Q R
C N T G E R S L S L L N C E E I K S Q F E G F V K D I M L
N K E E T K K E N S F E M Q K G D Q N P Q I A A H V I S E
A S S K T T S V L Q W A E K G Y Y T M S N N L V T L E N G
K Q L T V K R Q G L Y Y I Y A Q V T F C S N R E A S S Q A
P F I A S L C L K S P G R F E R I L L R A A N T H S S A K
P C G Q Q S I H L G G V F E L Q P G A S V F V N V T D P S
Q V S H G T G F T S F G L L K L
```

FIGURE 11
A.
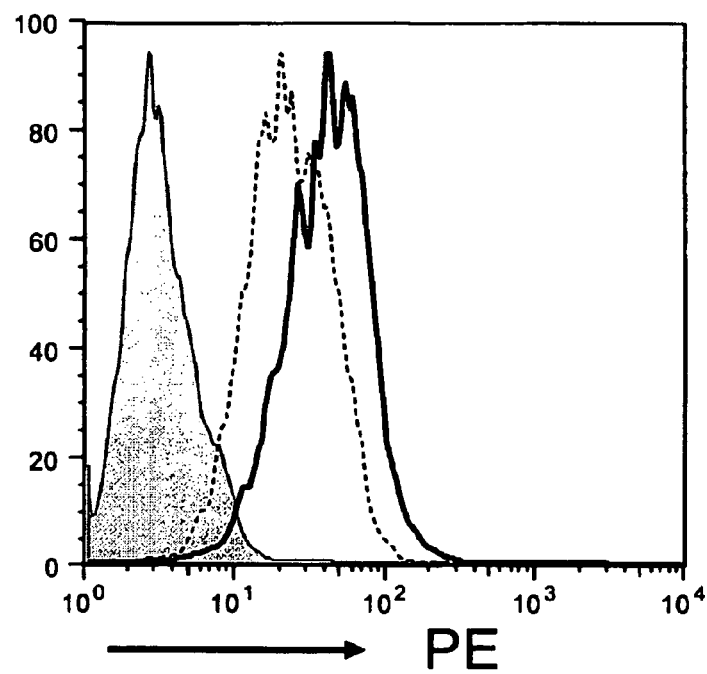
B.
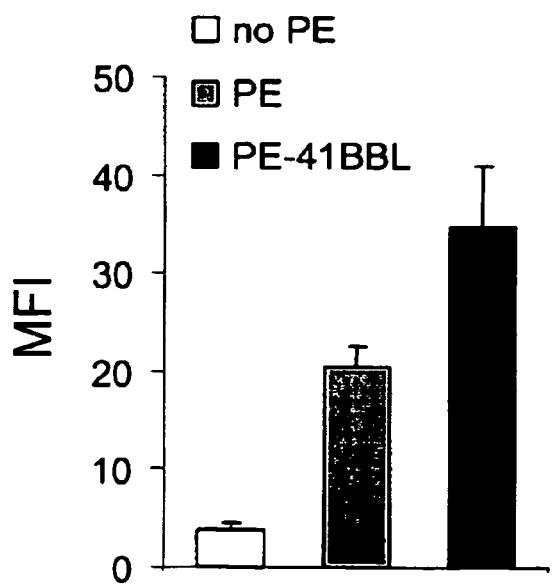

FIGURE 12
A.
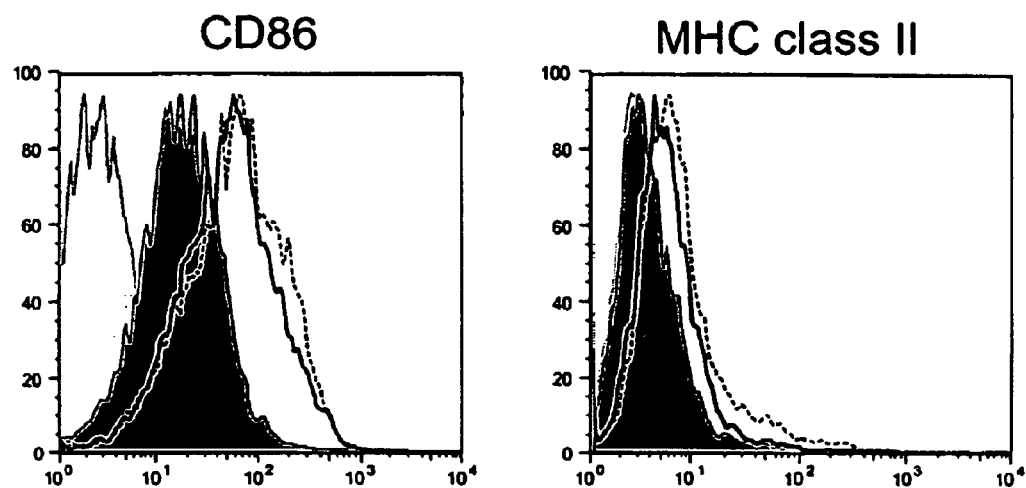
B.
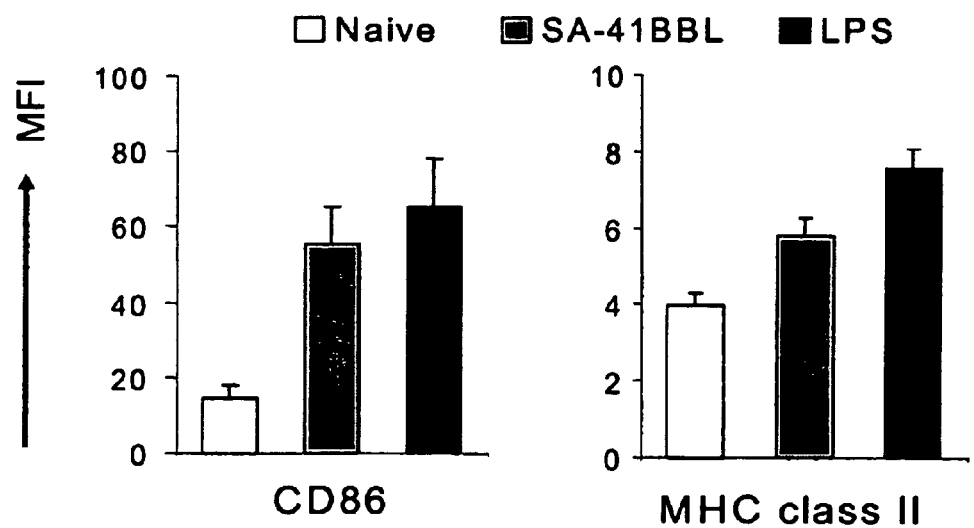

FIGURE 14
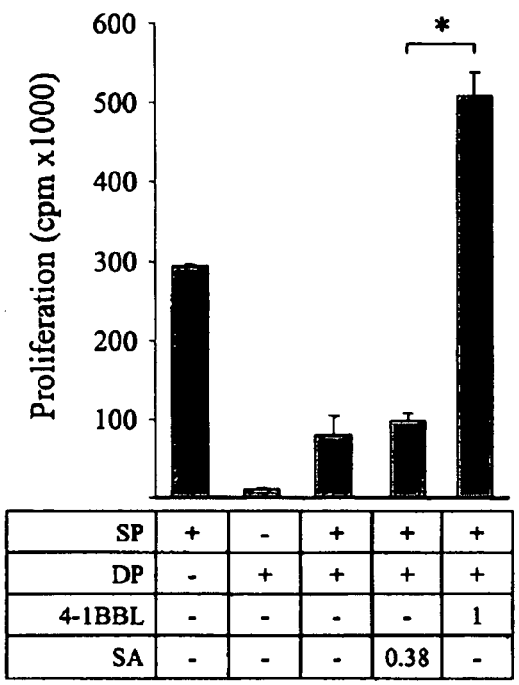
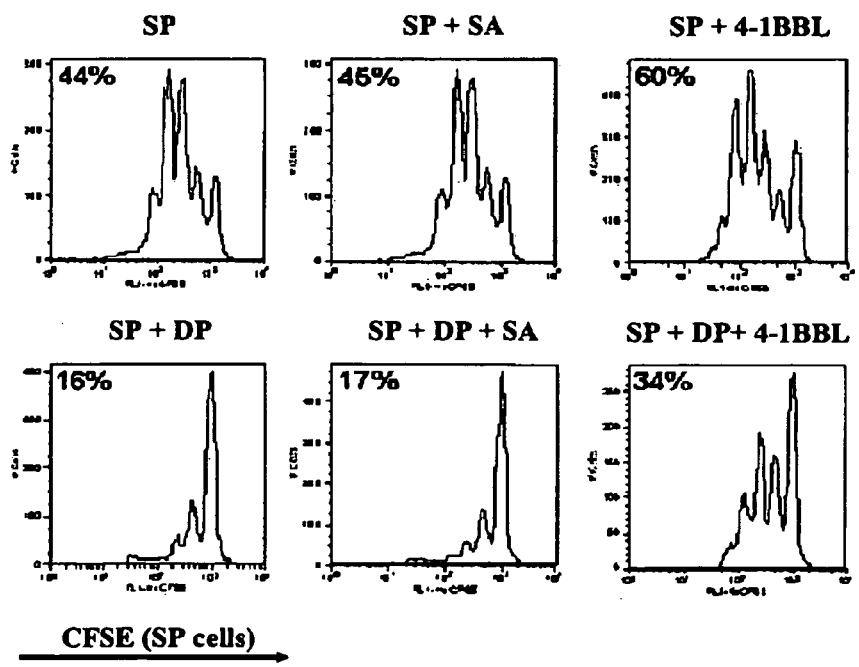
CFSE (SP cells)

SEQUENCE LISTING

<160> NUMBER OF SEQ ID NOS: 23

<210> SEQ ID NO 1
<211> LENGTH: 1213
<212> TYPE: DNA
<213> ORGANISM: Artificial Sequence

```
<220> FEATURE:
<223> OTHER INFORMATION: Description of Artificial Sequence: Synthetic
      nucleotide construct

<400> SEQUENCE: 1
acccgtgtgt aaagccgcgt ttccaaaatg tataaaaccg agagcatctg gccaatgtgc      60
atcagttgtg gtcagcagca aaatcaagtg aatcatctca gtgcaactaa aggggggatc     120
cgatctcaat atgaagttat gcatattact ggccgtcgtg gcctttgttg gcctctcgct     180
cgggagatct catcatcacc atcaccatat caccggcacc tggtacaacc agctcggctc     240
gaccttcatc gtgaccgcgg gcgccgatgg cgccctgacc ggaacctacg agtcggccgt     300
cggcaacgcc gagagccgct acgtcctgac cggtcgttac gacagcgccc cggccaccga     360
cggcagcggc accgccctcg gttggacggt ggcctggaag aataactacc gcaacgccca     420
ctccgcgacc acgtggagcg gccagtacgt cggcggcgcc gaggcgagga tcaacaccca     480
gtggctgctg acctccggcg ccaccgaggc caacgcctgg aagtccacgc tggtcggcca     540
cgacaccttc accaaggtga agccgtccgc cgcctcaagc gaattccaac gatctcacca     600
ggccaaccca gcagcacatc ttacaggagc aacgccagc ttgataggta ttggtggacc      660
tctgttatgg gagacacgac ttggcctggc cttcttgagg ggcttgacgt atcatgatgg     720
ggccctggtg accatggagc ccggttacta ctatgtgtac tccaaagtgc agctgagcgg     780
cgtgggctgc ccccaggggc tggccaatgg cctccccatc acccatggac tatacaagcg     840
cacatcccgc tacccgaagg agttagaact gctggtcagt cggcggtcac cctgtggccg     900
ggccaacagc tcccgagtct ggtgggacag cagcttcctg ggcggcgtgg tacatctgga     960
ggctggggaa gaggtggtgg tccgcgtgcc tggaaaccgc ctggtcagac acgtgacgg    1020
caccaggtcc tatttcggag ctttcatggt ctgaaggctg cggtgacaat gtattttgtg    1080
gagggacctc tccaggactc accctcgagt ctagagggcc cttcgaaggt aagcctatcc    1140
ctaaccctct cctcggtctc gattctacgc gtaccggtca tcatcaccat caccattgag    1200
tttaaacccg ctg                                                       1213

<210> SEQ ID NO 2
<211> LENGTH: 307
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 2

Met Lys Leu Cys Ile Leu Leu Ala Val Val Ala Phe Val Gly Leu Ser
  1               5                  10                  15

Leu Gly Arg Ser His His His His His His Ile Thr Gly Thr Trp Tyr
             20                  25                  30

Asn Gln Leu Gly Ser Thr Phe Ile Val Thr Ala Gly Ala Asp Gly Ala
         35                  40                  45

Leu Thr Gly Thr Tyr Glu Ser Ala Val Gly Asn Ala Glu Ser Arg Tyr
     50                  55                  60

Val Leu Thr Gly Arg Tyr Asp Ser Ala Pro Ala Thr Asp Gly Ser Gly
 65                  70                  75                  80

Thr Ala Leu Gly Trp Thr Val Ala Trp Lys Asn Asn Tyr Arg Asn Ala
                 85                  90                  95

His Ser Ala Thr Thr Trp Ser Gly Gln Tyr Val Gly Gly Ala Glu Ala
            100                 105                 110
```

-continued

```
Arg Ile Asn Thr Gln Trp Leu Leu Thr Ser Gly Ala Thr Glu Ala Asn
            115                 120                 125
Ala Trp Lys Ser Thr Leu Val Gly His Asp Thr Phe Thr Lys Val Lys
        130                 135                 140
Pro Ser Ala Ala Ser Ser Glu Phe Gln Arg Ser His Gln Ala Asn Pro
145                 150                 155                 160
Ala Ala His Leu Thr Gly Ala Asn Ala Ser Leu Ile Gly Ile Gly Gly
                165                 170                 175
Pro Leu Leu Trp Glu Thr Arg Leu Gly Leu Ala Phe Leu Arg Gly Leu
            180                 185                 190
Thr Tyr His Asp Gly Ala Leu Val Thr Met Glu Pro Gly Tyr Tyr Tyr
        195                 200                 205
Val Tyr Ser Lys Val Gln Leu Ser Gly Val Gly Cys Pro Gln Gly Leu
    210                 215                 220
Ala Asn Gly Leu Pro Ile Thr His Gly Leu Tyr Lys Arg Thr Ser Arg
225                 230                 235                 240
Tyr Pro Lys Glu Leu Glu Leu Leu Val Ser Arg Arg Ser Pro Cys Gly
                245                 250                 255
Arg Ala Asn Ser Ser Arg Val Trp Trp Asp Ser Ser Phe Leu Gly Gly
            260                 265                 270
Val Val His Leu Glu Ala Gly Glu Glu Val Val Val Arg Val Pro Gly
        275                 280                 285
Asn Arg Leu Val Arg Pro Arg Asp Gly Thr Arg Ser Tyr Phe Gly Ala
    290                 295                 300
Phe Met Val
305

<210> SEQ ID NO 3
<211> LENGTH: 1268
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 3
catctccagt gcaactaaag gggggatccg atctcaatat gaagttatgc atattactgg      60
ccgtcgtggc ctttgttggc ctctcgctcg ggagatctat ccacgtgacc aaggaagtga     120 agaagtggc aacgctgtcc tgtggtcaca atgtttctgt tgaagagctg cacaaactc      180 gcatctactg gcaaaggag aagaaaatgg tgctgactat gatgtctggg acatgaata     240 tatggcccga gtacaagaac cggaccatct ttgatatcac taataacctc tccattgtga     300
tcctggctct cgcccatctg acgagggca catacgagtg tgttgttctg aagtatgaaa     360
aagacgcttt caagcgggaa cacctggctg aagtgacgtt atcagtcaaa gctgacttcc     420
ctacacctag tatatctgac tttgaaattc aacttctaa tattagaagg ataatttgct     480
caacctctgg aggttttcca gagcctcacc tctcctggtt ggaaaatgga gaagaattaa     540
atgccatcaa cacaacagtt tcccaagatc ctgaaactga gctctatgct gttagcagca     600
aactggattt caatatgaca accaaccaca gcttcatgtg tctcatcaag tatggacatt     660
taagagtgaa tcagaccttc aactggaata caaccaagca agagatct catcatcacc     720 atcaccatat caccggcacc tggtacaacc agctcggctc gaccttcatc gtgaccgcgg     780
gcgccgacgg cgccctgacc ggaacctacg agtcggccgt cggcaacgcc gagagccgct     840
acgtcctgac cggtcgttac gacagcgccc cggccaccga cggcagcggc accgccctcg     900
```

```
gttggacggt ggcctggaag aataactacc gcaacgccca ctccgcgacc acgtggagcg    960
gccagtacgt cggcggcgcc gaggcgagga tcaacacccg tggctgttg acctccggcg   1020 ccaccgaggc caacgcctgg aagtccacgc tggtcggcca cgacaccttc accaaggtga   1080
agccgtccgc cgcctcaagc cgaattctgc agatatccag cacagtggcg gccgctcgag   1140
tctagagggc ccttcgaagg taagcctatc cctaaccctc tcctcggtct cgattctacg   1200
cgtaccggtc atcatcacca tcaccattga gtttaaaccc gctgatcagc ctcgactgtg   1260
ctttctaa                                                           1268
```

<210> SEQ ID NO 4
<211> LENGTH: 368
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 4

Met Lys Leu Cys Ile Leu Leu Ala Val Val Ala Phe Val Gly Leu Ser
 1               5                  10                  15

Leu Gly Arg Ser Ile His Val Thr Lys Glu Val Lys Glu Val Ala Thr
            20                  25                  30

Leu Ser Cys Gly His Asn Val Ser Val Glu Glu Leu Ala Gln Thr Arg
        35                  40                  45

Ile Tyr Trp Gln Lys Glu Lys Lys Met Val Leu Thr Met Met Ser Gly
    50                  55                  60

Asp Met Asn Ile Trp Pro Glu Tyr Lys Asn Arg Thr Ile Phe Asp Ile
65                  70                  75                  80

Thr Asn Asn Leu Ser Ile Val Ile Leu Ala Leu Arg Pro Ser Asp Glu
                85                  90                  95

Gly Thr Tyr Glu Cys Val Val Leu Lys Tyr Glu Lys Asp Ala Phe Lys
            100                 105                 110

Arg Glu His Leu Ala Glu Val Thr Leu Ser Val Lys Ala Asp Phe Pro
        115                 120                 125

Thr Pro Ser Ile Ser Asp Phe Glu Ile Pro Thr Ser Asn Ile Arg Arg
    130                 135                 140

Ile Ile Cys Ser Thr Ser Gly Gly Phe Pro Glu Pro His Leu Ser Trp
145                 150                 155                 160

Leu Glu Asn Gly Glu Glu Leu Asn Ala Ile Asn Thr Thr Val Ser Gln
                165                 170                 175

Asp Pro Glu Thr Glu Leu Tyr Ala Val Ser Ser Lys Leu Asp Phe Asn
            180                 185                 190

Met Thr Thr Asn His Ser Phe Met Cys Leu Ile Lys Tyr Gly His Leu
        195                 200                 205

Arg Val Asn Gln Thr Phe Asn Trp Asn Thr Thr Lys Gln Glu Arg Ser
    210                 215                 220

His His His His His Ile Thr Gly Thr Trp Tyr Asn Gln Leu Gly
225                 230                 235                 240

Ser Thr Phe Ile Val Thr Ala Gly Ala Asp Gly Ala Leu Thr Gly Thr
                245                 250                 255

Tyr Glu Ser Ala Val Gly Asn Ala Glu Ser Arg Tyr Val Leu Thr Gly
            260                 265                 270

Arg Tyr Asp Ser Ala Pro Ala Thr Asp Gly Ser Gly Thr Ala Leu Gly
        275                 280                 285

Trp Thr Val Ala Trp Lys Asn Asn Tyr Arg Asn Ala His Ser Ala Thr

```
                290              295              300
Thr Trp Ser Gly Gln Tyr Val Gly Gly Ala Glu Ala Arg Ile Asn Thr
305              310              315              320

Gln Trp Leu Leu Thr Ser Gly Ala Thr Glu Ala Asn Ala Trp Lys Ser
            325              330              335

Thr Leu Val Gly His Asp Thr Phe Thr Lys Val Lys Pro Ser Ala Ala
        340              345              350

Ser Ser Arg Ile Leu Gln Ile Ser Ser Thr Val Ala Ala Ala Arg Val
    355              360              365

<210> SEQ ID NO 5
<211> LENGTH: 1294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 5
ttcatgcaac taaagggggg atccgatctc aatatgaagt tatgcatatt actggccgtc      60
gtggcctttg ttggcctctc gctcgggaga tctcatcatc accatcacca tatcaccggc     120
acctggtaca accagctcgg ctcgaccttc atcgtgaccg cgggcgccga tggcgccctg     180
accggaacct acgagtcggc cgtcggcaac gccgagagcc gctacgtcct gaccggtcgt     240
tacgacagcg ccccggccac cgacggcagc ggcaccgccc tcggttggac ggtggcctgg     300
aagaataact accgcaacgc ccactccgcg accacgtgga cggccagta cgtcggcggc     360
gccgaggcga ggatcaacac ccagtggctg ttgacctccg gcgccaccga ggccaacgcc     420
tggaagtcca cgctggtcgg ccacgacacc ttcaccaagg tgaagccgtc cgccgcctca     480
agcgaattcc gcaccgagcc tcggccagcg ctcacaatca ccacctcgcc caacctgggt     540
acccgagaga taatgcaga ccaggtcacc cctgtttccc acattggctg ccccaacact     600
acacaacagg gctctcctgt gttcgccaag ctactggcta aaaccaagc atcgttgtgc     660
aatacaactc tgaactggca cagccaagat ggagctggga gctcatacct atctcaaggt     720
ctgaggtacg aagaagacaa aaaggagttg gtggtagaca gtcccgggct ctactacgta     780
tttttggaac tgaagctcag tccaacattc acaaacacag gccacaaggt gcagggctgg     840
gtctctcttg tttttgcaagc aaagcctcag gtagatgact ttgacaactt ggccctgaca     900
gtggaactgt tcccttgctc catggagaac aagttagtgg accgttcctg gagtcaactg     960
ttgctcctga aggctggcca ccgcctcagt gtgggtctga gggcttatct gcatggagcc    1020
caggatgcat acagagactg ggagctgtct tatcccaaca ccaccagctt tggactcttt    1080
cttgtgaaac ccgacaaccc atgggaatga gaactatcct tcttgtgact cctagttgct    1140
aagtcctcaa gctgctatgc tcgagtctag agggcccttc gaaggtaagc ctatccctaa    1200
ccctctcctc ggtctcgatt ctacgcgtac cggtcatcat caccatcacc attgagttta    1260
aacccgctga tcagcctcga ctgtgccttt ctaa                                1294

<210> SEQ ID NO 6
<211> LENGTH: 358
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 6
```

```
Met Lys Leu Cys Ile Leu Leu Ala Val Val Ala Phe Val Gly Leu Ser
 1               5                  10                  15

Leu Gly Arg Ser His His His His Ile Thr Gly Thr Trp Tyr
            20                  25                  30

Asn Gln Leu Gly Ser Thr Phe Ile Val Thr Ala Gly Ala Asp Gly Ala
            35                  40                  45

Leu Thr Gly Thr Tyr Glu Ser Ala Val Gly Asn Ala Glu Ser Arg Tyr
 50                  55                  60

Val Leu Thr Gly Arg Tyr Asp Ser Ala Pro Ala Thr Asp Gly Ser Gly
 65                  70                  75                  80

Thr Ala Leu Gly Trp Thr Val Ala Trp Lys Asn Asn Tyr Arg Asn Ala
                85                  90                  95

His Ser Ala Thr Thr Trp Ser Gly Gln Tyr Val Gly Gly Ala Glu Ala
            100                 105                 110

Arg Ile Asn Thr Gln Trp Leu Leu Thr Ser Gly Ala Thr Glu Ala Asn
            115                 120                 125

Ala Trp Lys Ser Thr Leu Val Gly His Asp Thr Phe Thr Lys Val Lys
        130                 135                 140

Pro Ser Ala Ala Ser Ser Glu Phe Arg Thr Glu Pro Arg Pro Ala Leu
145                 150                 155                 160

Thr Ile Thr Thr Ser Pro Asn Leu Gly Thr Arg Glu Asn Asn Ala Asp
                165                 170                 175

Gln Val Thr Pro Val Ser His Ile Gly Cys Pro Asn Thr Thr Gln Gln
                180                 185                 190

Gly Ser Pro Val Phe Ala Lys Leu Leu Ala Lys Asn Gln Ala Ser Leu
            195                 200                 205

Cys Asn Thr Thr Leu Asn Trp His Ser Gln Asp Gly Ala Gly Ser Ser
210                 215                 220

Tyr Leu Ser Gln Gly Leu Arg Tyr Glu Glu Asp Lys Lys Glu Leu Val
225                 230                 235                 240

Val Asp Ser Pro Gly Leu Tyr Tyr Val Phe Leu Glu Leu Lys Leu Ser
                245                 250                 255

Pro Thr Phe Thr Asn Thr Gly His Lys Val Gln Gly Trp Val Ser Leu
            260                 265                 270

Val Leu Gln Ala Lys Pro Gln Val Asp Asp Phe Asp Asn Leu Ala Leu
        275                 280                 285

Thr Val Glu Leu Phe Pro Cys Ser Met Glu Asn Lys Leu Val Asp Arg
    290                 295                 300

Ser Trp Ser Gln Leu Leu Leu Lys Ala Gly His Arg Leu Ser Val
305                 310                 315                 320

Gly Leu Arg Ala Tyr Leu His Gly Ala Gln Asp Ala Tyr Arg Asp Trp
                325                 330                 335

Glu Leu Ser Tyr Pro Asn Thr Thr Ser Phe Gly Leu Phe Leu Val Lys
            340                 345                 350

Pro Asp Asn Pro Trp Glu
        355
```

<210> SEQ ID NO 7
<211> LENGTH: 1295
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 7

```
ttcatgcaac taaagggggg atccgatctc aatatgaagt tatgcatatt actggccgtc      60
gtggcctttg ttggcctctc gctcgggaga tctcatcatc accatcacca tatcaccggc     120
acctggtaca accagctcgg ctcgaccttc atcgtgaccg cgggcgccga tggcgccctg     180
accggaacct acgagtcggc cgtcggcaac gccgagagcc gctacgtcct gaccggtcgt     240
tacgacagcg ccccggccac cgacggcagc ggcaccgccc tcggttggac ggtggcctgg     300
aagaataact accgcaacgc ccactccgcg accacgtgga cggccagta cgtcggcggc     360
gccgaggcga ggatcaacac ccagtggctg ttgacctccg gcgccaccga ggccaacgcc     420
tggaagtcca cgctggtcgg ccacgacacc ttcaccaagg tgaagccgtc cgccgcctca     480
agcgaattcg cctgccccctg ggccgtgtcc ggggctcgcg cctcgcccgg ctccgcggcc     540
agcccgagac tccgcgaggg tcccgagctt tcgcccgacg atcccgccgg cctcttggac     600
ctgcggcagg gcatgtttgc gcagctggtg gcccaaaatg ttctgctgat cgatgggccc     660
ctgagctggt acagtgaccc aggcctggca ggcgtgtccc tgacgggggg cctgagctac     720
aaagaggaca cgaaggagct ggtggtggcc aaggctggag tctactatgt cttctttcaa     780
ctagagctgc ggcgcgtggt ggccggcgag ggctcaggct ccgtttcact tgcgctgcac     840
ctgcagccac tgcgctctgc tgctgggggcc gccgccctgg ctttgaccgt ggacctgcca     900
cccgcctcct ccgaggctcg gaactcggcc ttcggtttcc agggccgctt gctgcacctg     960
agtgccggcc agcgcctggg cgtccatctt cacactgagg ccagggcacg ccatgcctgg    1020
cagcttaccc agggcgccac agtcttggga ctcttccggg tgaccccccga atcccagcc    1080
ggactcccctt caccgaggtc ggaataacgc ccagcctggg tgcagcccac ctggacagag    1140
tccgaatcct actccatcct ctcgagtcta gagggccctt cgaaggtaag cctatcccta    1200
accctctcct cggtctcgat tctacgcgta ccggtcatca tcaccatcac cattgagttt    1260
aaacccgctg atcagcctcg actgtgcctt tctaa                               1295
```

<210> SEQ ID NO 8
<211> LENGTH: 357
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 8

Met Lys Leu Cys Ile Leu Leu Ala Val Val Ala Phe Val Gly Leu Ser
1               5                   10                  15

Leu Gly Arg Ser His His His His His His Ile Thr Gly Thr Trp Tyr
            20                  25                  30

Asn Gln Leu Gly Ser Thr Phe Ile Val Thr Ala Gly Ala Asp Gly Ala
        35                  40                  45

Leu Thr Gly Thr Tyr Glu Ser Ala Val Gly Asn Ala Glu Ser Arg Tyr
    50                  55                  60

Val Leu Thr Gly Arg Tyr Asp Ser Ala Pro Ala Thr Asp Gly Ser Gly
65                  70                  75                  80

Thr Ala Leu Gly Trp Thr Val Ala Trp Lys Asn Asn Tyr Arg Asn Ala
                85                  90                  95

His Ser Ala Thr Thr Trp Ser Gly Gln Tyr Val Gly Gly Ala Glu Ala
            100                 105                 110

Arg Ile Asn Thr Gln Trp Leu Leu Thr Ser Gly Ala Thr Glu Ala Asn
        115                 120                 125

Ala Trp Lys Ser Thr Leu Val Gly His Asp Thr Phe Thr Lys Val Lys

```
                130             135             140
Pro Ser Ala Ala Ser Ser Glu Phe Ala Cys Pro Trp Ala Val Ser Gly
145                 150                 155                 160

Ala Arg Ala Ser Pro Gly Ser Ala Ala Ser Pro Arg Leu Arg Glu Gly
                165                 170                 175

Pro Glu Leu Ser Pro Asp Asp Pro Ala Gly Leu Leu Asp Leu Arg Gln
            180                 185                 190

Gly Met Phe Ala Gln Leu Val Ala Gln Asn Val Leu Leu Ile Asp Gly
        195                 200                 205

Pro Leu Ser Trp Tyr Ser Asp Pro Gly Leu Ala Gly Val Ser Leu Thr
    210                 215                 220

Gly Gly Leu Ser Tyr Lys Glu Asp Thr Lys Glu Leu Val Val Ala Lys
225                 230                 235                 240

Ala Gly Val Tyr Tyr Val Phe Phe Gln Leu Glu Leu Arg Arg Val Val
                245                 250                 255

Ala Gly Glu Gly Ser Gly Ser Val Ser Leu Ala Leu His Leu Gln Pro
            260                 265                 270

Leu Arg Ser Ala Ala Gly Ala Ala Ala Leu Ala Leu Thr Val Asp Leu
        275                 280                 285

Pro Pro Ala Ser Ser Glu Ala Arg Asn Ser Ala Phe Gly Phe Gln Gly
    290                 295                 300

Arg Leu Leu His Leu Ser Ala Gly Gln Arg Leu Gly Val His Leu His
305                 310                 315                 320

Thr Glu Ala Arg Ala Arg His Ala Trp Gln Leu Thr Gln Gly Ala Thr
                325                 330                 335

Val Leu Gly Leu Phe Arg Val Thr Pro Glu Ile Pro Ala Gly Leu Pro
            340                 345                 350

Ser Pro Arg Ser Glu
        355
```

<210> SEQ ID NO 9
<211> LENGTH: 1334
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 9

| | | | | | |
|---|---|---|---|---|---|
| catctccagt | gcaactaaag | gggggatccg | atctcaatat | gaagttatgc | atattactgg | 60 |
| ccgtcgtggc | ctttgttggc | ctctcgctcg | ggagatctgc | tcctctgaag | attcaagctt | 120 |
| atttcaatga | gactgcagac | ctgccatgcc | aatttgcaaa | ctctcaaaac | caaagcctga | 180 |
| gtgagctagt | agtattttgg | caggaccagg | aaaacttggt | tctgaatgag | gtatacttag | 240 |
| gcaaagagaa | atttgacagt | gttcattcca | gtatatgggc | cgcacaagtt | tttgattcgg | 300 |
| acagttggac | cctgagactt | cacaatcttc | agatcaagga | caagggcttg | tatcaatgta | 360 |
| tcatccatca | caaaagccca | acaggaatga | ttcgcatcca | ccagatgaat | tctgaactgt | 420 |
| cagtgcttgc | taacttcagt | caacctgaaa | tagtaccaat | ttctaatata | acagaaaatg | 480 |
| tgtacataaa | tttgacctgc | tcatctatac | acggttaccc | agaacctaag | aagatgagtg | 540 |
| ttttgctaag | aaccaagaat | tcaactatcg | agtatgatgg | tattatgcag | aaatctcaag | 600 |
| ataatgtcac | agaactgtac | gacgtttcca | tcagcttgtc | tgtttcattc | cctgatgtta | 660 |
| cgagcaatat | gaccatcttc | tgtattctgg | aaactgacaa | gacgcggctt | ttatcttcac | 720 |
| ctttctctat | agagcttgag | gaccctcagc | ctccccccaga | ccacattcct | agatctcatc | 780 |

```
atcaccatca ccatatcacc ggcacctggt acaaccagct cggctcgacc ttcatcgtga      840
ccgcgggcgc cgacggcgcc ctgaccggaa cctacgagtc ggccgtcggc aacgccgaga      900
gccgctacgt cctgaccggt cgttacgaca gcgccccggc caccgacggc agcggcaccg      960
ccctcggttg acggtggcc tggaagaata actaccgcaa cgcccactcc gcgaccacgt      1020
ggagcggcca gtacgtcggc ggcgccgagg cgaggatcaa cacccagtgg ctgttgacct      1080
ccggcgccac cgaggccaac gcctggaagt ccacgctggt cggccacgac accttcacca      1140
aggtgaagcc gtccgccgcc tcaagccgaa ttctgcagat atccagcaca gtggcggccg      1200
ctcgagtcta gagggccctt cgaaggtaag cctatcccta accctctcct cggtctcgat      1260
tctacgcgta ccggtcatca tcaccatcac cattgagttt aaacccgctg atcagcctcg      1320
actgtgcttt ctaa                                                        1334
```

<210> SEQ ID NO 10
<211> LENGTH: 376
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 10

```
Met Lys Leu Cys Ile Leu Leu Ala Val Val Ala Phe Val Gly Leu Ser
 1               5                  10                  15

Leu Gly Arg Ser Ala Pro Leu Lys Ile Gln Ala Tyr Phe Asn Glu Thr
             20                  25                  30

Ala Asp Leu Pro Cys Gln Phe Ala Asn Ser Gln Asn Gln Ser Leu Ser
         35                  40                  45

Glu Leu Val Val Phe Trp Gln Asp Gln Glu Asn Leu Val Leu Asn Glu
     50                  55                  60

Val Tyr Leu Gly Lys Glu Lys Phe Asp Ser Val His Ser Lys Tyr Met
 65                  70                  75                  80

Gly Arg Thr Ser Phe Asp Ser Asp Ser Trp Thr Leu Arg Leu His Asn
                 85                  90                  95

Leu Gln Ile Lys Asp Lys Gly Leu Tyr Gln Cys Ile Ile His His Lys
            100                 105                 110

Lys Pro Thr Gly Met Ile Arg Ile His Gln Met Asn Ser Glu Leu Ser
        115                 120                 125

Val Leu Ala Asn Phe Ser Gln Pro Glu Ile Val Pro Ile Ser Asn Ile
    130                 135                 140

Thr Glu Asn Val Tyr Ile Asn Leu Thr Cys Ser Ser Ile His Gly Tyr
145                 150                 155                 160

Pro Glu Pro Lys Lys Met Ser Val Leu Leu Arg Thr Lys Asn Ser Thr
                165                 170                 175

Ile Glu Tyr Asp Gly Ile Met Gln Lys Ser Gln Asp Asn Val Thr Glu
            180                 185                 190

Leu Tyr Asp Val Ser Ile Ser Leu Ser Val Ser Phe Pro Asp Val Thr
        195                 200                 205

Ser Asn Met Thr Ile Phe Cys Ile Leu Glu Thr Asp Lys Thr Arg Leu
    210                 215                 220

Leu Ser Ser Pro Phe Ser Ile Glu Leu Glu Asp Pro Gln Pro Pro Pro
225                 230                 235                 240

Asp His Ile Pro Arg Ser His His His His His Ile Thr Gly Thr
                245                 250                 255
```

```
Trp Tyr Asn Gln Leu Gly Ser Thr Phe Ile Val Thr Ala Gly Ala Asp
            260                 265                 270

Gly Ala Leu Thr Gly Thr Tyr Glu Ser Ala Val Gly Asn Ala Glu Ser
        275                 280                 285

Arg Tyr Val Leu Thr Gly Arg Tyr Asp Ser Ala Pro Ala Thr Asp Gly
    290                 295                 300

Ser Gly Thr Ala Leu Gly Trp Thr Val Ala Trp Lys Asn Asn Tyr Arg
305                 310                 315                 320

Asn Ala His Ser Ala Thr Thr Trp Ser Gly Gln Tyr Val Gly Gly Ala
                325                 330                 335

Glu Ala Arg Ile Asn Thr Gln Trp Leu Leu Thr Ser Gly Ala Thr Glu
            340                 345                 350

Ala Asn Ala Trp Lys Ser Thr Leu Val Gly His Asp Thr Phe Thr Lys
        355                 360                 365

Val Lys Pro Ser Ala Ala Ser Ser
    370                 375

<210> SEQ ID NO 11
<211> LENGTH: 158
<212> TYPE: PRT
<213> ORGANISM: Human papillomavirus

<400> SEQUENCE: 11

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 12
<211> LENGTH: 151
<212> TYPE: PRT
<213> ORGANISM: Human papillomavirus

<400> SEQUENCE: 12

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
```

```
                        50                  55                  60
Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Gly Gln Lys Pro Leu Cys Pro
            100                 105                 110

Asp Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 13
<211> LENGTH: 98
<212> TYPE: PRT
<213> ORGANISM: Human papillomavirus

<400> SEQUENCE: 13

Met His Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 14
<211> LENGTH: 1303
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 14
ccgatctcaa tatgaagtta tgcatattac tggccgtcgt ggcctttgtt ggcctctcgc      60
tcgggagatc tcatcatcac catcaccata tcaccggcac ctggtacaac cagctcggct    120
cgaccttcat cgtgaccgcg ggcgccgatg cgccctgac cggaacctac gagtcggccg     180
tcggcaacgc cgagagccgc tacgtcctga ccggtcgtta cgacagcgcc ccggccaccg    240
acggcagcgg caccgccctc ggttggacgg tggcctggaa gaataactac cgcaacgccc    300
actccgcgac cacgtggagc ggccagtacg tcggcggcgc cgaggcgagg atcaacaccc    360
agtggctgtt gacctccggc gccaccgagg ccaacgcctg gaagtccacg ctggtcggcc    420
acgacaccct caccaaggtg aagccgtccg ccgcctcaag cgaattcttg acaagatag     480 aagatgaaag gaatcttcat gaagattttg tattcatgaa acgatacag agatgcaaca    540 caggagaaag atcctatcc ttactgaact gtgaggagat taaagccag tttgaaggct    600 ttgtgaagga tataatgtta aacaaagagg agacgaagaa agaaaacagc tttgaaatgc    660
```

```
aaaaaggtga tcagaatcct caaattgcgg cacatgtcat aagtgaggcc agcagtaaaa    720
caacatctgt gttacagtgg gctgaaaaag gatactacac catgagcaac aacttggtaa    780
ccctggaaaa tgggaaacag ctgaccgtta aaagacaagg actctattat atctatgccc    840
aagtcacctt ctgttccaat cgggaagctt cgagtcaagc tccatttata gccagcctct    900
gcctaaagtc ccccggtaga ttcgagagaa tcttactcag agctgcaaat acccacagtt    960
ccgccaaacc ttgcgggcaa caatccattc acttgggagg agtatttgaa ttgcaaccag   1020
gtgcttcggt gtttgtcaat gtgactgatc caagccaagt gagccatggc actggcttca   1080
cgtcctttgg cttactcaaa ctctgaacag tgtcaccttg caggagctct aagccgaatt   1140
ctgcagatat ccagcacagt ggcggccgct cgagtctaga gggcccttcg aaggtaagcc   1200
tatccctaac cctctcctcg gtctcgattc tacgcgtacc ggtcatcatc accatcacca   1260
ttgagtttaa acccgctgat cagcctcgac tgtgcctttc taa                     1303
```

<210> SEQ ID NO 15
<211> LENGTH: 364
<212> TYPE: PRT
<213> ORGANISM: Artificial Sequence
<220> FEATURE:
<223> OTHER INFORMATION: Description of Artificial Sequence: Synthetic
    protein construct

<400> SEQUENCE: 15

```
Met Lys Leu Cys Ile Leu Leu Ala Val Val Ala Phe Val Gly Leu Ser
  1               5                  10                  15

Leu Gly Arg Ser His His His His His His Ile Thr Gly Thr Trp Tyr
             20                  25                  30

Asn Gln Leu Gly Ser Thr Phe Ile Val Thr Ala Gly Ala Asp Gly Ala
         35                  40                  45

Leu Thr Gly Thr Tyr Glu Ser Ala Val Gly Asn Ala Glu Ser Arg Tyr
     50                  55                  60

Val Leu Thr Gly Arg Tyr Asp Ser Ala Pro Ala Thr Asp Gly Ser Gly
 65                  70                  75                  80

Thr Ala Leu Gly Trp Thr Val Ala Trp Lys Asn Asn Tyr Arg Asn Ala
                 85                  90                  95

His Ser Ala Thr Thr Trp Ser Gly Gln Tyr Val Gly Gly Ala Glu Ala
            100                 105                 110

Arg Ile Asn Thr Gln Trp Leu Leu Thr Ser Gly Ala Thr Glu Ala Asn
        115                 120                 125

Ala Trp Lys Ser Thr Leu Val Gly His Asp Thr Phe Thr Lys Val Lys
    130                 135                 140

Pro Ser Ala Ala Ser Ser Glu Phe Leu Asp Lys Ile Glu Asp Glu Arg
145                 150                 155                 160

Asn Leu His Glu Asp Phe Val Phe Met Lys Thr Ile Gln Arg Cys Asn
                165                 170                 175

Thr Gly Glu Arg Ser Leu Ser Leu Leu Asn Cys Glu Glu Ile Lys Ser
            180                 185                 190

Gln Phe Glu Gly Phe Val Lys Asp Ile Met Leu Asn Lys Glu Glu Thr
        195                 200                 205

Lys Lys Glu Asn Ser Phe Glu Met Gln Lys Gly Asp Gln Asn Pro Gln
    210                 215                 220

Ile Ala Ala His Val Ile Ser Glu Ala Ser Lys Thr Thr Ser Val
225                 230                 235                 240

Leu Gln Trp Ala Glu Lys Gly Tyr Tyr Thr Met Ser Asn Asn Leu Val
```

```
                    245                 250                 255

Thr Leu Glu Asn Gly Lys Gln Leu Thr Val Lys Arg Gln Gly Leu Tyr
            260                 265                 270

Tyr Ile Tyr Ala Gln Val Thr Phe Cys Ser Asn Arg Glu Ala Ser Ser
        275                 280                 285

Gln Ala Pro Phe Ile Ala Ser Leu Cys Leu Lys Ser Pro Gly Arg Phe
    290                 295                 300

Glu Arg Ile Leu Leu Arg Ala Ala Asn Thr His Ser Ser Ala Lys Pro
305                 310                 315                 320

Cys Gly Gln Gln Ser Ile His Leu Gly Gly Val Phe Glu Leu Gln Pro
                325                 330                 335

Gly Ala Ser Val Phe Val Asn Val Thr Asp Pro Ser Gln Val Ser His
            340                 345                 350

Gly Thr Gly Phe Thr Ser Phe Gly Leu Leu Lys Leu
        355                 360

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser Gly Gly Gly Gly Ser Gly Gly Gly Gly Ser
 1               5                  10                  15

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Glu Asn Asp Ala Gln Ala Pro Lys Ser
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gln Asn Asp Ala Gln Ala Pro Lys Ser
 1               5                  10

<210> SEQ ID NO 19
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 19

Arg Ala His Tyr Asn Ile Val Thr Phe
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Ala Pro Gly Asn Tyr Pro Ala Leu
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ile Ile Asn Phe Glu Lys Leu
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala His Tyr Asn Ile Val Thr Phe
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
 1               5
```

IMMUNOSTIMULATORY COMPOSITIONS AND METHODS

CROSS REFERENCE TO RELATED APPLICATIONS

The present application is a divisional of U.S. application Ser. No. 11/635,066, filed Dec. 7, 2006, which claims the benefit under 35 U.S.C. §119(e) of the filing dates of the following U.S. provisional applications: 60/748,177 (filed Dec. 8, 2005); 60/771,179 (Feb. 6, 2006); 60/799,643 (filed May 12, 2006); and 60/863,173 (filed Oct. 27, 2006). Each of the foregoing applications is incorporated by reference herein in its entirety.

FIELD OF THE INVENTION

The present invention generally relates to methods of generating or enhancing an immune response, including an immune response against an antigen, to compositions for effecting the methods, and to modified immune cells useful in such methods.

BACKGROUND OF THE INVENTION

Approaches directed to boosting a host's immune response to address diseases and conditions characterized by a deficiency in immunity or resolvable by a more aggressive immune response have been described. Exemplary diseases or conditions where such approaches may be advantageous include cancer, influenza and human immunodeficiency virus (HIV).

Cancer treatments involving surgery, chemotherapy and radiotherapy are commonly used, but these approaches lack tumor specificity, resulting in adverse side effects and less than satisfactory clinical responses. Accordingly, methods of boosting the immune response to cancer by specifically directing that response to the target cancerous cells without significant, detrimental effects on normal cells would offer distinct advantages over traditional cancer therapy.

There is a consensus that immune surveillance plays a role in the prevention and eradication of tumors, and adaptive immunity mediated by T cells plays a role in this process. See, e.g., Pardoll, Nat. Rev. Immunol. 2002, 2:227-38; Rosenberg, Nature 2001, 411: 380-84; Finn, O J. Nat. Rev. Immunol. 2003, 3:630-41. T cell-mediated immunity also plays a role in various immunotherapeutic approaches that have shown efficacy in preclinical and limited clinical settings. See, e.g., Pardoll, supra; Finn, supra; Antonia et al., Curr. Opin. Immunol 2004, 16:130-6. Tumors are targeted by the immune system because they express tumor associated antigens (TAAs), which are either mutated or over/aberrantly expressed self-proteins, or proteins derived from oncogenic viruses. See, e.g., Finn, supra; Antonio, supra. Under physiological conditions, tumor antigens are picked up by dendritic cells (DC), carried to peripheral lymphoid organs, and presented to naïve T cells under immunogenic conditions allowing for their activation and differentiation into effector cells ($T_{eff}$). These cells then traffic to tumor sites and generate anti-tumor responses for tumor eradication. See, e.g., Spiotto, et al., Immunity. 2002; 17:737-47; Ochsenbein et al., Nature 2001; 411:1058-64; Yu et al., Nat. Immunol. 2004; 5:141-9.

A productive T cell response requires three distinct signals: Signals 1, 2, and 3. Signal 1 is generated by T cell receptors (TCR) interacting with nominal peptides presented by major histocompatibility complex (MHC) molecules on the surface of professional antigen presenting cells (APCs). Signal 2 is mediated by a series of costimulatory molecules and is critical to a sustained immune response. Signal 3 is transduced via cytokines elaborated by activated lymphocytes and APCs, such as macrophages and DC, and is important to the maintenance of effector immune responses.

Tumors have developed various mechanisms to evade immune surveillance. These mechanisms include: (i) lack of Signal 1, arising from either the inefficient display of MHC/tumor antigen bimolecular complexes on tumor cells, defects in the transduction of this signal, or expression of MHC homologues, MIC, that inhibit natural killer (NK cells) expressing NKG2 inhibitory receptors; (ii) absence of Signal 2 originating from the lack of costimulatory molecules or expression of coinhibitory molecules on tumor cells; (iii) tumor-mediated suppression of immune responses through the secretion of anti-inflammatory molecules, induction of anergy in tumor-reactive T cells, physical elimination of $T_{eff}$ cells via apoptosis, or induction of naturally occurring $CD4^+$ $CD25^+FoxP3^+T$ regulatory ($T_{reg}$) cells, and (iv) regulation of immunity by the tumor stroma. Accumulating evidence suggests that many of these mechanisms may operate simultaneously in patients with large tumor burdens.

Cancer vaccines which include antigens from the target cancer have attracted particular interest because of the promise of specificity, safety, efficacy and the long-term memory of the immune system that may prevent recurrence of the cancer. Once it was established that the immune system plays an important role in safeguarding individuals against cancer and may be modulated to eradicate existing tumors in animal models, intense efforts were devoted to the development of therapeutic vaccines. See, e.g., Berzofsky et al., J. Clin. Invest 2004, 113:1515-25; Platsoucas et al., Anticancer Res. 2003; 23, 1969-96; Finn, supra. Current vaccine strategies include the use of specific TAAs in conjunction with nonspecific or specific adjuvants, whole tumor cell lysates, tumor cells genetically modified to express costimulatory molecules, cytokines, and/or chemokines, DC pulsed with tumor antigens or transfected with tumor RNA or DNA, and intratumoral injection of a range of vectors encoding various immunostimulatory molecules. The limited efficacy of these approaches may stem from the ability of progressing tumors to control immune responses using one or several immune evasion strategies, or due to immunosuppressive mechanisms, inefficient presentation of TAAs, or lack of potent activation of DC, $T_{eff}$ cells, and NK cells.

SUMMARY OF THE INVENTION

The present invention provides immunostimulatory compositions and methods.

In accordance with one embodiment, the invention provides a combination comprising (a) a first conjugate comprising (i) a conjugate member comprising a first immune co-stimulatory polypeptide and (ii) a conjugate member comprising a first member of a binding pair; and (b) a second conjugate comprising (i) a conjugate member comprising a first antigen and (ii) a conjugate member comprising a second member of the binding pair. In one embodiment, the first member of the binding pair may comprise avidin or streptavidin and the second member of the binding pair may comprise biotin. In another embodiment, the first conjugate may comprise a fusion polypeptide comprising the first immune co-stimulatory polypeptide and the first member of the binding pair. In one specific embodiment, the first immune co-stimulatory polypeptide is selected from the group consisting of 4-1BBL, CD86, ICOSL, PD-L1, PD-L2, B7-H3, B7-H4, OX40L, CD27L, CD30L, LIGHT, BAFF, APRIL, CD80 and CD40L.

In one specific embodiment, the first antigen is associated with an infectious agent, such as human or avian influenza or human immunodeficiency virus. In another specific embodiment, the first antigen is a tumor associated antigen.

In one embodiment, the combination further comprises a third conjugate comprising (i) a conjugate member comprising a second immune co-stimulatory polypeptide and a first member of a binding pair and (ii) a conjugate member comprising a second antigen and a second member of a binding pair. In this embodiment, the second immune co-stimulatory polypeptide is the same as or different from the first immune co-stimulatory polypeptide; the second antigen is the same as or different from the first antigen; the first and second binding pair members of the third conjugate are the same as or different from the first and second binding pair members of the first and second conjugates. Additionally, the first conjugate member may be bound to the second conjugate member via binding between the first and second binding pair members.

In another embodiment, the second conjugate of the combination comprises (i) a conjugate member comprising an infectious agent and (ii) a conjugate member comprising a second member of the binding pair.

In accordance with another aspect of the invention, there is provided a method of generating or enhancing an immune response against a tumor which expresses a first tumor-associated antigen, comprising administering to a patient with the tumor (a) a first conjugate comprising (i) a conjugate member comprising a first immune co-stimulatory polypeptide and (ii) a conjugate member comprising a first member of a binding pair, and a second conjugate comprising (i) a conjugate member comprising the first tumor-associated antigen and (ii) a conjugate member comprising a second member of the binding pair; or (b) immune cells which have been treated in vitro with the first and second conjugates.

In one embodiment, the first and second conjugates are administered to the patient, separately or simultaneously, including as part of a single composition.

In another embodiment, the patient is administered immune cells which have been treated in vitro with the first and second conjugates. In one specific embodiment, the immune cells comprise a receptor for the immune co-stimulatory polypeptide, and wherein the first conjugate is conjugated to the immune cells via binding between the immune co-stimulatory polypeptide and the receptors, and the second conjugate is conjugated to the immune cell via binding between the first and second binding pair members.

In one embodiment, the method further comprises administering a third conjugate comprising (i) a conjugate member comprising a second immune co-stimulatory polypeptide and a first member of a binding pair and (ii) a conjugate member comprising a second tumor-associated antigen and a second member of a binding pair. In this embodiment, the second immune co-stimulatory polypeptide is the same as or different from the first immune co-stimulatory polypeptide; the second antigen is the same as or different from the first antigen; the first and second binding pair members of the third conjugate are the same as or different from the first and second binding pair members of the first and second conjugates. Additionally, the first conjugate member may be bound to the second conjugate member via binding between the first and second binding pair members.

In accordance with another aspect of the invention, there is provided a method of modifying immune cells to generate or enhance an immune response to a tumor expressing a tumor-associated antigen or to an infectious agent, comprising contacting immune cells expressing a receptor for a first immune co-stimulatory polypeptide with (a) a first conjugate comprising (i) a conjugate member comprising the first immune co-stimulatory polypeptide and (ii) a conjugate member comprising a first member of a binding pair; and (b) a second conjugate comprising (i) a conjugate member comprising an antigen associated with the tumor or infectious agent or the infectious agent and (ii) a conjugate member comprising a second member of the binding pair. The first conjugate may be conjugated to the immune cells via binding between the immune co-stimulatory polypeptide and the receptor, and the second conjugate may be conjugated to the immune cell via binding between the first and second binding pair members.

In one embodiment, the immune cell is a T cell, such as a CD4+ cell or CD8+ cell, or a neutrophil, natural killer cell, monocyte or dendritic cell.

In another embodiment, the immune cells comprise a receptor for a second immune co-stimulatory polypeptide and the method further comprises contacting the immune cells with a third conjugate comprising (i) a conjugate member comprising the second immune co-stimulatory polypeptide and a first member of a binding pair and (ii) a conjugate member comprising a second antigen associated with the tumor or infectious agent or the infectious agent and a second member of the binding pair. In this embodiment, the second immune co-stimulatory polypeptide is the same as or different from the first immune co-stimulatory polypeptide; the second antigen, if present, is the same as or different from the first antigen, if present; the first and second binding pair members of the third conjugate are the same as or different from the first and second binding pair members of the first and second conjugates. Additionally, the first conjugate member may be bound to the second conjugate member via binding between the first and second binding pair members.

In accordance with another aspect of the invention, there is provided a modified immune cell expressing a receptor for a first immune co-stimulatory polypeptide, wherein the modified immune cell is modified with (a) a first conjugate comprising (i) a conjugate member comprising the first immune co-stimulatory polypeptide and (ii) a conjugate member comprising a first member of a binding pair; and (b) a second conjugate comprising (i) a conjugate member comprising a first antigen or infectious agent and (ii) a conjugate member comprising a second member of the binding pair, wherein the first conjugate is conjugated to the immune cell via binding between the immune co-stimulatory polypeptide and the receptor, and the second conjugate is conjugated to the immune cell via binding between the first and second binding pair members. In one embodiment, the immune cell is a T cell, such as a CD4+ cell or CD8+ cell, or a neutrophil, natural killer cell, monocyte or dendritic cell.

In accordance with another aspect of the invention, there is provided a method of inducing or enhancing an immune response against an infectious agent, comprising administering to a patient suffering from or at risk of infection with the infectious agent (a) a first conjugate comprising (i) a conjugate member comprising a first immune co-stimulatory polypeptide and (ii) a conjugate member comprising a first member of a binding pair; and (b) a second conjugate comprising (i) a conjugate member comprising a first antigen associated with the infectious agent or comprising the infectious agent and (ii) a conjugate member comprising a second member of the binding pair. In one embodiment, at least one of the first and second conjugates is administered by direct injection into a site of infection.

In one specific embodiment, the infection is human or avian influenza and the first antigen is selected from the group consisting of H, N, M1, M2e, NS1, NS2 (NEP), NP, PA, PB1, and PB2. In another specific embodiment, the infection is HIV and the first antigen is selected from the group of HIV antigens consisting of Gag proteins, Pol, Vif, Vpr, Rev, Vpu, envelope eptiopes, Tat, and Nef.

In one embodiment, the method further comprises administering a third conjugate comprising (i) a conjugate member comprising a second immune co-stimulatory polypeptide and a first member of a binding pair and (ii) a conjugate member comprising a second antigen associated with the infection or the infectious agent and a second member of the binding pair, wherein the second immune co-stimulatory polypeptide is the same as or different from the first immune co-stimulatory polypeptide; the second antigen, if present, is the same as or different from the first antigen, if present; the first and second binding pair members of the third conjugate are the same as or different from the first and second binding pair members of the first and second conjugates, and the first conjugate member is bound to the second conjugate member via binding between the first and second binding pair members.

In accordance with another aspect of the invention, there is provided a conjugate comprising an immune co-stimulatory polypeptide and avidin or streptavidin.

In accordance with another aspect of the invention, there is provided a method of inducing an immunostimulatory response in an animal comprising administering to the animal a conjugate comprising an immune co-stimulatory polypeptide and avidin or streptavidin. In some embodiments, the method further comprises administering an antigen to the animal.

BRIEF DESCRIPTION OF THE DRAWINGS

FIGS. 1A and 1B set forth the nucleotide sequence (SEQ ID NO:1) and amino acid sequence (SEQ ID NO:2), respectively, of a fusion protein comprising core streptavidin and the extracellular domain of the murine LIGHT protein. The core streptavidin sequence is underlined in FIG. 1B.

FIGS. 2A and 2B set forth the nucleotide sequence (SEQ ID NO:3) and amino acid sequence (SEQ ID NO:4), respectively, of a fusion protein comprising the extracellular domain of human CD80 and core streptavidin. The core streptavidin sequence is underlined in FIG. 2B.

FIGS. 3A and 3B set forth the nucleotide sequence (SEQ ID NO:5) and amino acid sequence (SEQ ID NO:6), respectively, of a fusion protein comprising the extracellular domain of murine 4-1BBL and core streptavidin. The core streptavidin sequence is underlined in FIG. 3B.

FIGS. 4A and 4B set forth the nucleotide sequence (SEQ ID NO:7) and amino acid sequence (SEQ ID NO:8), respectively, of a fusion protein comprising core streptavidin and the extracellular domain of human 4-1BBL. The core streptavidin sequence is underlined in FIG. 4B.

FIGS. 5A and 5B set forth the nucleotide sequence (SEQ ID NO:9) and amino acid sequence (SEQ ID NO:10), respectively, of a fusion protein comprising core streptavidin and the extracellular domain of human CD86. The core streptavidin sequence is underlined in FIG. 5B.

FIGS. 6A, 6B and 6C set forth the amino acid sequences of HPV16 E6 (SEQ ID NO:11), an HPV16 E6 variant (SEQ ID NO:12), and HV16 E7 (SEQ ID NO:13).

FIGS. 7A & 7B set forth the nucleotide and amino acid sequences of the CSA-human CD40L (SEQ ID NOs 14 & 15) constructs used in the examples.

FIG. 11A is a histogram showing PE+ cells of untreated DC (gray filled area), DC treated with biotinylated PE (dashed line) and DC treated with biotinylated PE/CSA-4-1BBL conjugate (solid line). FIG. 11B shows the mean fluorescence intensity (MFI) of PE for DC receiving each treatment.

FIG. 12A shows the results of flow cytometry performed to analyze CD86 and MHC class II levels of DC untreated (dark gray) or treated with CSA-41BBL (solid line) or LPS (dashed line) in the presence of GM-CSF. FIG. 12B shows the mean fluorescence intensity of CD86 and MHC class II.

FIG. 14A shows the results of coculture experiments where CD4$^+$ CD25$^-$ (single positive, SP) and CD4$^+$ CD25$^+$ (double positive, DP) T cells were sorted from the spleen and peripheral lymph nodes of naïve BALB/c mice and cultured alone or at 1:1 ratio for 3 days, in cultures supplemented with irradiated splenocytes, an anti-CD3 antibody (0.5 µg/ml), and indicated concentrations (µg/ml) of 4-1BBL or equimolar amount of control CSA protein. FIG. 14B shows the results of a CFSE assay where SP T cells labeled with CFSE were used in a suppression assay under conditions described for FIG. 14A, except that 4-1BBL was used at 0.5 µg/ml. The percentage of dividing cells is shown for each histogram.

FIG. 20D shows the results when a murine macrophage cell line genetically modified to express human CD40 (CD40KO) was stimulated with CSA or CSA-hCD40L (1 µg/ml) for 3 hours and RNA was extracted and analyzed by RNAse protection assay using the RiboQuant multiprobe RNAse protection system with the template mck-3b. The protected probes for IL-6, L32, and GAPDH are shown. The histogram represents the band density of IL-6 after normalization with the housekeeping gene L32.

DETAILED DESCRIPTION

Figure 8:
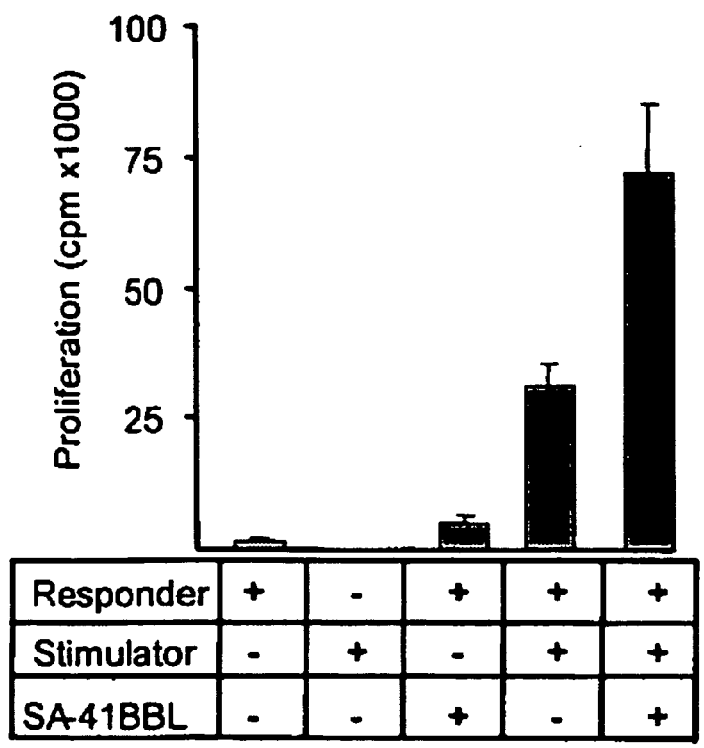
FIG. 8 shows the results of allogenic mixed lymphocyte reactions using naïve BALB/c lymphocytes as responders and allogeneic C57BL/6 irradiated splenocytes as stimulators. Indicated cultures were supplemented with 1 µg/ml CSA-41BBL fusion protein.

The present invention provides methods and compositions for generating or enhancing an immune response, including an immune response against an antigen, such as a TAA or antigen associated with an infectious agent such as human and avian influenza or HIV. The invention also provides modified immune cells that are useful for generating or enhancing an immune response to an antigen. The invention also provides immunotherapy methods, including cancer immunotherapy methods, such as methods of reducing tumor size and methods of inhibiting the growth of tumor cells, and methods of treating or preventing infections.

A productive adaptive immune response requires coordinated and timely interactions between naïve T effector ("Teff") cells and APCs within the organized structures of secondary lymphoid organs. This interaction promotes reciprocal activation of Teff cells and APCs, leading to the expression of various cell surface ligands and receptors as well as soluble proteins that are important for the initiation, maintenance, and long-term memory of the response. As discussed above, at least three signals (Signal 1, 2, and 3), are involved in the initial activation of naïve T cells. Several immune co-stimulatory molecules have been implicated that stimulate one or more of these Signals.

The present invention relates to the use of one or more immune co-stimulatory polypeptides and one or more antigens associated with a tumor or infectious agent in methods that present the antigen to immune cells such that an effective immune response against the tumor or infectious agent is induced. Alternatively, an infectious agent can be used in place of an antigen associated therewith. While not wanting to be bound by any theory, it is believed that the present invention achieves advantageous results by facilitating antigen presentation and activating the immune response. In another alternative embodiment, the invention provides immunostimulatory moieties comprising an immune co-stimulatory polypeptide, that are useful for stimulating an immune response.

For the purposes of the present application, the following terms have these definitions:

As used herein "a" or "an" means one or more, unless specifically indicated to mean only one.

"Administration" as used herein encompasses all suitable means of providing a substance to a patient. Common routes include oral, sublingual, transmucosal, transdermal, rectal, vaginal, subcutaneous, intramuscular, intravenous, intra-arterial, intrathecal, via catheter, via implant etc. In some embodiments, a composition is administered near or directly to the tumor, such as by direct injection into the tumor or injection into the blood such as when the tumor is a tumor of the blood.

"Antigen" is used herein without limitation. Antigens include proteins, lipids, sugars, nucleic acids, chemical moieties, and other moieties that induce an immune response. Antigens include proteins, which may or may not be modified, such as by glycosylation or methylation, that are cyclized or bound to lipids, for example. Antigens associated with an infectious agent or disease include antigens that are part of the infectious agent, such as envelope proteins, capsid proteins, surface proteins, toxins, cell walls, antigenic lipids, and the like. Other antigens may be expressed only in the presence of the host. Other suitable antigens may, in some embodiments, include antigens of the host, including those that are induced, modified or otherwise overexpressed as a marker of infection or disease. All such antigens that are derived from, or associated with, an infectious agent, an infection, a condition or disease, are suitable for use in the present invention. Also suitable for use as an "antigen" in accordance with the present invention are peptides comprising antigenic portions of full-length proteins, such as peptides comprising a portion of a protein that induces an immune response, such as an immunogenic epitope. For example, suitable antigens may include synthetic peptides that induce an immune response.

"Binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like.

"Immune co-stimulatory polypeptide" means a polypeptide that increases an individual's immune response against a pathogen (including an infectious agent) or tumor.

"Immune cell" as used herein includes any cell that is involved in the generation, regulation or effect of the acquired or innate immune system. Immune cells include T cells such as CD4+ cells, CD8+ cells and various other T cell subsets, B cells, natural killer cells, macrophages, monocytes and dendritic cells, and neutrophils.

"Patient" as used herein includes any vertebrate animal, including equine, ovine, caprine, bovine, porcine, avian, canine, feline and primate species. In one embodiment, the patient is human. A person of ordinary skill in the art will recognize that particular immune co-stimulatory molecules, signaling molecules, cell markers, cell types, infectious agents etc., discussed with reference to one species, may have corresponding analogues in different species, and that such analogues, and their use in corresponding and related species, are encompassed by the present invention.

"Tumor" as used herein includes solid and non solid tumors (such as leukemia); and different stages of tumor development from pre-cancerous lesions and benign tumors, to cancerous, malignant and metastatic tumors.

In general terms, the invention provides methods whereby an immune response against a first antigen is generated or enhanced using (a) a first conjugate comprising (i) a conjugate member comprising a first immune co-stimulatory polypeptide and (ii) a conjugate member comprising a first member of a binding pair, and (b) a second conjugate comprising (i) a conjugate member comprising the first antigen and (ii) a conjugate member comprising a second member of the binding pair. The antigen may be a TAA or an antigen associated with an infectious agent, or the infectious agent itself. The conjugates may be administered directly to a patient comprising the antigen or infectious agent, or may be used to treat immune cells which then are administered to the patient. The invention also provides compositions comprising the conjugates, immune cells treated with the conjugates, and methods of making treated immune cells.

The invention also provides immunostimulatory moieties comprising an immune co-stimulatory polypeptide, such as a conjugate or fusion protein comprising an immune co-stimulatory polypeptide and avidin or streptavidin. The invention also provides a method of inducing an immunostimulatory response in an animal comprising administering an immunostimulatory moiety to the animal. In some embodiments, an antigen also is administered to the animal. Compositions comprising the moiety also are provided.

In accordance with one aspect of the invention, the antigen or infectious agent is presented to immune cells as part of a conjugate comprising an immune co-stimulatory polypeptide that selectively targets one or more types of immune cells, such as any of the immune co-stimulatory polypeptides described below. Thus, in accordance with one embodiment, the invention provides a conjugate comprising an immune co-stimulatory polypeptide and an antigen associated with a tumor or infectious agent or the infectious agent. The antigen or infectious agent can be conjugated to the immune co-stimulatory polypeptide by any means, including by covalent bonding, directly or through a linker, or through binding pair members.

In one embodiment, the antigen or infectious agent is conjugated to the immune co-stimulatory polypeptide through the binding interactions of a binding pair. In accordance with this embodiment, each of the antigen (or infectious agent) and the immune co-stimulatory polypeptide is conjugated to a member of a binding pair, and the binding interactions of the binding pair members link the antigen (or infectious agent) and immune co-stimulatory polypeptide together in a conjugate, such as an immune co-stimulatory polypeptide-first binding pair member::second binding pair member—antigen (or infectious agent) conjugate.

In accordance with this embodiment, the invention provides a combination comprising (a) a first conjugate comprising (i) a conjugate member comprising a first immune co-stimulatory polypeptide and (ii) a conjugate member comprising a first member of a binding pair, and (b) a second conjugate comprising (i) a conjugate member comprising a first antigen associated with a tumor or infectious agent (or the infectious agent itself) and (ii) a conjugate member comprising a second member of the binding pair.

In another embodiment, the combination comprises a third conjugate comprising (i) a conjugate member comprising a second immune co-stimulatory polypeptide and (ii) a conjugate member comprising a second antigen associated with the tumor or infectious agent (or the infectious agent itself), wherein the immune co-stimulatory polypeptide of the third conjugate is the same as or different from the immune co-stimulatory polypeptide of the first conjugate and the second antigen is the same as or different from the first antigen. In a specific aspect of this embodiment, the immune co-stimulatory polypeptide and second antigen of the third conjugate are bound together via binding between binding pair members associated with each of the immune co-stimulatory polypeptide and second antigen. In accordance with this embodiment, the binding pair members of the third conjugate may be the same as or different from the first and second biding pair members of the first and second conjugates.

The first, second and optional third conjugates may be provided in separate compositions. Alternatively, the first and second conjugates may be provided in a single composition, and the third conjugate may be provided in a separate composition. In yet another alternative, the first, second and third conjugates are provided in a single composition. In another alternative, the first conjugate is provided in one composition and the second and third conjugates are provided in another composition Each composition optionally may comprise a pharmaceutically acceptable carrier. A pharmaceutically acceptable carrier is a material that can be used as a vehicle for the composition because the material is inert or otherwise medically acceptable, as well as compatible with the active agent(s), in the context of administration. A pharmaceutically acceptable carrier can contain conventional pharmaceutical additives as are well known in the art.

Immune Co-Stimulatory Polypeptides

Immune co-stimulatory molecules are involved in the natural interaction between naïve T cells and antigen presenting cells, which results in their reciprocal activation and prompts the expression of various cell surface ligands and receptors, and soluble proteins that contribute to the initiation, maintenance, and long-term memory of the immune response. As discussed above, at least three signals are required for the initial activation of naïve T cells. Signal 1 is generated by interactions between a T cell receptor (TCR) and a nominal peptide presented by major histocompatibility complex (MHC) molecules on the surface of professional APC, such as dendritic cells (DC). Signal 2 can be mediated by several different molecules and is important to a sustained immune response. Signal 3 is transduced via cytokines elaborated by activated T cells and APC and is important to the maintenance of effector immune responses.

A number of immune co-stimulatory molecules have been identified. Exemplary immune co-stimulatory molecules (polypeptides) useful in accordance with the invention include, without limitation, LIGHT, CD80 (B7-1), CD86 (B7-2), ICOS, ICOSL (including B7h, B7-H2, B7RP-1, GL-50 and LICOS), CD94 (KP43), CD40L (CD154), ICAM-1 (CD54), ICAM-2, ICAM-3, SLAM (CD150), HAS (CD24), 4-1BB (CDw137), 4-1BBL (CDw137L), OX40L, CD28, CD40 (BP50), CD25 (IL-2R α), Lymphotoxin (LTα or LTβ), TNF, Fas-L, GITR (activation-inducible TNRF), GITR Ligand, CD11a ($α_L$ integrin), CD11b ($α_M$ integrin), L-selectin (CD62L), CD69 (very early activation antigen), CD70 (CD27L), PD-L1, PD-L2, B7-H3, B7-H4, OX40L, 4-1BBL, CD27L, CD30L, LIGHT, BAFF, and APRIL. See, e.g., Watts & DeBenedette, 1999, *Curr. Opin. Immunol.,* 11:286-93.

Unless specified herein as "full-length," reference herein to an immune co-stimulatory polypeptide encompasses the full-length polypeptide as well as fragments or portions thereof that exhibit immune co-stimulatory function, including, but not limited to those fragments and portions specifically identified below. Thus, for example, reference to a 4-1BBL polypeptide connotes a polypeptide comprising a fragment or portion of full-length 4-1BBL that exhibits immune co-stimulatory function, such as the extracellular domain of 4-1BBL or the full-length 4-1BBL protein. In one embodiment, the immune co-stimulatory polypeptide does not comprise the transmembrane domain of an immune co-stimulatory molecule. In one embodiment, the immune co-stimulatory polypeptide comprises the extracellular domain of an immune co-stimulatory molecule, or a receptor binding fragment thereof.

Examples of representative nucleic acid sequences and the encoded immune co-stimulatory polypeptides include those shown in GenBank Accession Nos. AB029155 (murine LIGHT); NM__172014 (human TNFSF14 mRNA transcript variant 2); NM__003807 (human TNFSF14 mRNA transcript variant 1); NM__005191 (human CD80 mRNA); NM__009855 (mouse CD80 mRNA); NM__214087 *Sus scrofa* CD80 mRNA); NM__009404 (murine Tnfsf9 mRNA); NM__003811 (human TNFSF9 mRNA); NM__181384 (*Rattus norvegicus* Tnfsf9 mRNA); BAA88559 (murine LIGHT protein); Q9QYH9 (murine TNFSF14 membrane bound protein and soluble protein); AAH18058 (human TNFSF14 protein); NP__005182 (human CD80 protein); NP__033985 (murine CD80 protein); NP__037058 (*Rattus norvegicus* CD80 protein); NP__003802 (human TNFSF9 protein); NP__033430 (mouse TNFSF9 protein); NP__852049 (*Rattus norvegicus* TNFSF9 protein); NM__012967 (*Rattus norvegicus* ICAM-1 mRNA); X69711 (human ICAM-1 mRNA); X52264 (murine ICAM-1 mRNA); X69819 (human ICAM-3 mRNA); AF296283 (murine ICAM-4 mRNA); NM__021181 (human SLAMF7 mRNA); NM__033438 (human SLAMF9 mRNA); NM__029612 (murine SLAMF9 mRNA); NM__144539 (murine SLAMF7 mRNA); L13944 (murine CD18 gene); X53586 (human integrin α6 mRNA); X68742 (human integrin α mRNA); J04145 (Human neutrophil adherence receptor alpha-M subunit mRNA); AJ246000 (human leucocyte adhesion receptor, L-selectin mRNA); AY367061 (human L-selectin mRNA, partial cds); Y13636 (murine CD70 mRNA); NM__001252 (human TNFSF7 mRNA); BC000725 (human TNFSF7 mRNA (cDNA clone MGC:1597 IMAGE:3506629), complete cds); X69397 (human CD24 gene and complete CDS); NM__013230 (human CD24 mRNA); NM__012752 (*Rattus norvegicus* CD24 mRNA); Y00137 (murine tumor necrosis factor-beta (lymphotoxin) gene); X02911 (human tumor necrosis factor-beta (lymphotoxin) gene); D00102 (human lymphotoxin mRNA, complete CDS); X01393 (human lymphotoxin mRNA); and A06316 ((human lymphotoxin mRNA). Other nucleic acid sequences encoding the same or other immune co-stimulatory polypeptides and/or amino acid sequences of co-stimulatory polypeptides can be found, for example, by searching the publicly available GenBank database (available, for example, at ncbi.nlm.nih.gov on the World Wide Web).

Interactions between CD28 and CD80/CD86 appear to play a significant role in the transduction of Signal 2. See, e.g., Harding & Allison, J. Exp. Med. 1993, 177: 1791-96; Ramarathinam et al., J. Exp. Med. 1994, 179: 1205-14; Townsend & Allison, Science 1993, 259: 368-70; Gause et al., J. Immunol. 1997, 159: 1055-58. CD80 is usually not expressed on resting B cells and is expressed at low levels on peripheral blood monocytes and DC; however, both of these cells as well as macrophages and other APCs upregulate their expression of CD80 following activation. See, e.g., Lenschow et al., Ann. Rev. Immunol. 1996, 14: 233-58; Freeman et al., J. Immunol. 1989, 143:2714-22. In contrast, CD86 is constitutively expressed on peripheral blood monocytes and DC and more rapidly upregulated on B cells. See, e.g., Lenschow et al., supra, Inaba et al., J. Exp. Med. 1994, 180: 1849-60. TCR interaction with MHC/peptide complex on APCs allows for simultaneous engagement of CD80/86 molecules with CD28 and leads to the tyrosine phosphorylation of the lipid kinase phosphatidylinositol 3-kinase, which in turn initiates a series of complex intracellular events that result in the induction of IL-2 gene expression, cell proliferation, and differentiation into effector function. See, e.g., Slavik et al., Immunol. Res. 1999, 19: 1-24; Azuma et al., Nature 1993, 366: 76-79; Allison & Krummel, Science 1995, 270: 932-33.

Signal 2 may further augment a productive immune response by preventing cell death through the regulation of anti-apoptotic genes, such as Bcl-xL. See, e.g., Radvanyi et al., J. Immunol. 1996, 156: 1788-98; Boise et al., Immunity 1995, 3: 87-98; Boise & Thompson, Science 1996, 274: 67-68. Following the initial stages of immune activation, a number of additional receptor-ligand pairs are upregulated on the surface of T cells and APCs. These "secondary" receptor/ligand pairs, such as 4-1BBL/4-1BB, play important roles in the maintenance of post initial activation events, immune homeostasis, and generation of immunological memory. See, e.g., Yu et al., Nat. Immunol. 2004, 5: 141-49; Armitage et al., Nature 1992, 357: 80-82; Zhai et al., J. Clin. Invest. 1998, 102: 1142-51; Bourgeois et al. Science 2002, 297: 2060-63; Kikuchi et al., Nat. Med. 2000, 6: 1154-59.

1. 4-1BBL

In one particular embodiment of the invention, the immune co-stimulatory polypeptide is a 4-1BBL polypeptide. 4-1BBL (also known as 4-BB-L, 4-BB ligand, TNFSF9, ILA ligand) is a type II protein expressed on activated B cells, macrophages, and DC two to three days following activation. See, e.g., Alderson et al. Eur. J. Immunol. 1994, 24: 2219-27; Goodwin et al., Eur. J. Immunol. 1993, 23: 2631-41; Pollok et al., Eur. J. Immunol. 1994, 24: 367-74; DeBenedette et al., J. Immunol. 1997, 158: 551-59. Its receptor, 4-1BB (CD137), is expressed on the surface of activated $CD4^+$ and $CD8^+$ T cells, on natural killer cells, monocytes, and resting DC. See, e.g., Pollock, supra; Wilcox et al., J. Immunol. 2002, 169: 4230-36; Futagawa et al., Int. Immunol. 2002, 14: 275-86; Pollok et al., J. Immunol. 1993, 150: 771-81.

4-1BB/4-1BBL interactions also transduce Signal 2 to $CD8^+$ T cells in a CD28-independent manner and stimulate them to produce cytokines, expand, and acquire effector functions. See, e.g., Cannons et al., J. Immunol. 2001, 167: 1313-24; Hurtado et al., J. Immunol. 1995, 155: 3360-67. Kim & Broxmeyer, J. Hematother. Stem Cell Res. 2001, 10: 441-49; Saoulli et al., J. Exp. Med. 1998, 187: 1849-62; Shuford et al., J. Exp. Med. 1997, 186:47-55; Tan et al., J. Immunol. 1999, 163: 4859-68; Vinay & Kwon, Semin. Immunol. 1998, 10: 481-89. 4-1BB/4-1BBL interaction is also important for the activation of monocytes and DC, their synthesis of cytokines, and communication with NK cells. See, e.g., Futagawa et al., supra; Wilcox et al., J. Clin. Invest 2002, 109: 651-9. Similarly, in addition to its role in promoting the expansion of antigen-specific T cells through the upregulation of cyclins D2 and E, and downregulation of cyclin-dependent kinase inhibitor p27kip1, 4-1BB signaling plays a role in T cell survival, as it prevents activation-induced cell death via the upregulation of the anti-apoptotic Bcl-xL and Bcl-2 and the establishment of long-term immunological memory. See, e.g., Takahashi et al., J. Immunol. 1999, 162: 5037-40; Hurtado et al., J. Immunol. 1997, 158: 2600-09; Kim et al., Eur. J. Immunol. 1998, 28: 881-90. 4-1BB/4-1BBL interaction has also been shown to selectively promote type 1 cytokines, such as IL-2, IFN-γ, and TNF-α, suggesting that 4-1BB may be a costimulatory molecule specific for type 1 effector T cells, which play a role in tumor eradication.

It has recently been shown that $T_{reg}$ cells constitutively express 4-1BB receptor and that signal transduction through 4-1BB receptor inhibits the suppressive function of these cells. See, e.g., Choi et al., supra; Morris et al., supra, and the Examples below. This is important because $T_{reg}$ cells play a significant role in tumor evasion of the immune system. Several clinical studies demonstrated that a direct correlation exists between the number of $T_{reg}$ cells and tumor progression. Curiel et al., Nat. Med. 2004, 10: 942-49. Indeed, the eradication of $T_{reg}$ cells in animal models has resulted in the eradication of large tumors, providing direct evidence for their dominant role in tumor progression. Yu et al, J. Exp. Med. 2005, 201: 779-91. Similarly, infectious agents, such as HIV, may use $T_{reg}$ cells for immune evasion.

Although not wishing to be bound by theory, it is believed that the use of 4-1BBL as an immune co-stimulatory polypeptide in accordance with the invention may activate the 4-1BB cognate receptor on T cells, resulting in several important immune-stimulatory effects. One effect may be the transduction of Signal 2 to $CD8^+$ T cells in a CD28-independent manner, which stimulates the T cells to produce cytokines, to expand, and acquire effector functions. Another effect of 4-1BB/4-1BBL interaction may be activation of monocytes and DC which results in the synthesis and release of cytokines. Yet another effect of 4-1BB signaling may be the promotion of T cell survival and establishment of long-term immunological memory by preventing activation-induced cell death (AICD). Still another effect of 4-1BB/4-1BBL interaction may be the selective production of type 1 cytokines, such as IL-2, IL-12, IFN-γ, and TNF-α from T cells, DC and macrophages, which act upon type 1 effector T cells important to tumor eradication. Also, as explained above, 4-1BB/4-1BBL interaction may inhibit the suppressor function of $T_{reg}$ cells. Thus, for example, a 4-1BBL-antigen conjugate may specifically bind to DC expressing the 4-1BB receptor, facilitate antigen presentation, activate DC for the generation of a primary T cell response, directly act on activated T cells (including $T_{eff}$ cells) and NK cells to boost their response against the antigen, and inhibit the suppressive function of $T_{reg}$ cells.

4-1BBL contains 254 amino acids (26624 Da). See Alderson et al. Eur J. Immunol. 1994 September; 24(9):2219-27. The full amino acid sequence of human 4-1BBL can be found under accession no. P41273 in the Swiss-Prot database. 4-1BBL is a type II glycoprotein with residues 1-28 forming a potential cytoplasmic domain, residues 29-49 forming a single predicted transmembrane domain, residues 50-254 forming a potential extraceulluar domain, and residues 35-41 representing a poly-Leu stretch. The nucleotide sequence in humans encoding the 4-1BBL can be found in GenBank accession no. NM_003811.

As discussed above, 4-1BBL is expressed by activated antigen presenting cells including activated B cells, macrophages, and DC, 2-3 days following activation. 4-1BB, which is the receptor for 4-1BBL, is expressed on the surface of activated $CD4^+$ and $CD8^+$ T cells, on natural killer cells, monocytes, and resting DC. Residues 50-254 of 4-1BBL or fragments thereof that can bind to its cognate receptor 4-1BB, can be linked or expressed as a fusion with a binding pair member for use in accordance with the present invention. For example, FIGS. 3A and B show the nucleotide and amino acid sequences of a CSA-murine 4-1BBL fusion protein (SEQ ID NOs 5 and 6). FIGS. 4A and B show the nucleotide and amino acid sequences of a fusion protein comprising the extracellular domain of human 4-1BBL and core strepavidin (SEQ ID NOs 7 and 8).

2. CD80 & CD86

CD80 (also known as B7.1, CD28LG, LAB7) and CD86 (also known as B7.2, CD28LG2, LAB72) are exemplary co-stimulatory polypeptides, both of which bind to the CD28/CTLA4 co-receptor expressed by T cells. CD80 contains 288 amino acids (33048 Da). See Freeman et al. J. Immunol. 143 (8), 2714-2722 (1989). The full amino acid sequence of human CD80 can be found under accession no. P33681 in the Swiss-Prot database. CD80 is a type I glycoprotein with residues 1-34 forming a secretion signal, residues 35-242 forming a potential extraceulluar domain, residues 243-263 forming a potential transmembrane domain, and residues 264-288 forming a potential cytoplasmic domain. Thus the mature CD80 molecule without its secretion signal sequence represents amino acids 35-288. The nucleotide sequence in humans encoding CD80 can be found in GenBank accession no. NM_005191.

Figure 2B:
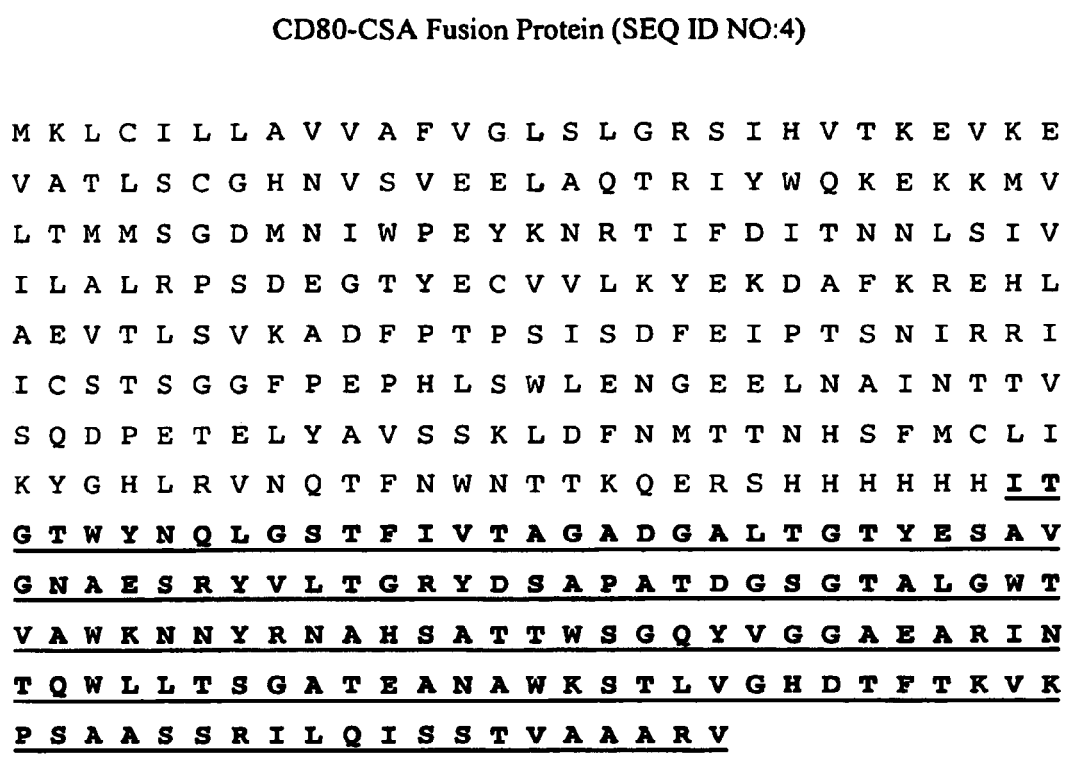

Residues 35-242 of CD80 or fragments thereof that can bind to its cognate receptor CD28 can be linked or expressed as a fusion protein with a binding pair member for use in accordance with the present invention. For example, FIGS. 2A and 2B set forth the nucleotides (SEQ ID NO:3) and amino acid sequence (SEQ ID NO:4) of a fusion protein comprising the extracellular domain of human CD80 (B7.1) and core streptavidin.

CD86 (B7.2) contains 329 amino acids (37696 Da). See Freeman et al. Science 262 (5135), 909-911 (1993). The full amino acid sequence of human CD86 can be found under accession no. P42081 in the Swiss-Prot database. CD86 is a type I glycoprotein with residues 1-23 forming a secretion signal, residues 24-247 forming a potential extracelluluar domain, residues 248-268 forming a potential transmembrane domain, and residues 269-329 forming a potential cytoplasmic domain. Thus, the mature CD86 molecule without its secretion signal sequence represents amino acids 24-329. The nucleotide sequence in humans encoding CD86 can be found in GenBank accession no. NM_175862.

Residues 24-247 of CD86 or fragments thereof that can bind to its cognate receptor CD28, can be linked or expressed as a fusion with a binding pair member for use in accordance with the present invention. For example, FIGS. 5A and 5B set forth the nucleotide (SEQ ID NO:9) and amino acid (SEQ ID NO: 10) sequences of a fusion protein comprising the extracellular domain of human CD86 (B7.2) and core streptavidin.

CD86 is usually not expressed on resting B cells and is expressed at low levels on peripheral blood monocytes (PBC) and DC. Its expression, however, is upregulated on B cells and other APC such as macrophages and DC following activation. In contrast, CD86 is constitutively expressed on PBC and DC and more rapidly upregulated on B cells. T cell receptor (TCR) interaction with the MHC/peptide complex on APC allows for simultaneous engagement of CD80/86 with CD28 on the T cell, which leads to tyrosine phosphorylation of the lipid kinase phosphotidylinositol 3-kinase, which in turn initiates a series of intracellular events that result in the induction of IL-2 gene expression, cell proliferation, and differentiation into effector function. Signal 2 may further augment a productive immune response by preventing cell death through the regulation of antiapoptotic genes, such as Bcl-xL.

3. LIGHT

Following the initial stages of immune activation, "secondary" receptor/ligand pairs such as 4-1BBL/4-1BB (discussed above) and LIGHT/HVEM become upregulated on the surface of T cells and APC. These receptor/ligand pairs are involved in the maintenance of post initial activation events, immune homeostasis, and generation of immunological memory.

The LIGHT polypeptide (also known as TNFS14, HVEM-L, LTg, TR2) is a TNF superfamily member which is homologous to lymphotoxin. See Mauri et al. Immunity 8 (1), 21-30 (1998). The full amino acid sequence of human LIGHT can be found under accession no. O43557 in the Swiss-Prot database. LIGHT contains 240 amino acids (26351 Da) and is a type II glycoprotein with residues 1-37 forming a potential cytoplasmic domain, residues 38-58 forming a single predicted transmembrane domain, and residues 59-240 forming a potential extracelluluar domain. A cleavage site involves residues 82-83. The nucleotide sequence in humans encoding LIGHT can be found in GenBank accession no. NM_172014.

Residues 59-240 of LIGHT or fragments thereof that can bind to its cognate receptor HVEM, LTβR or TR6, can be linked or expressed as a fusion with a binding pair member for use in accordance with the present invention. For example, FIGS. 1A and 1B set forth the nucleotide (SEQ ID NO:1) and amino acid sequences (SEQ ID NO:2) of a fusion comprising core streptavidin and the extracellular domain of murine LIGHT.

LIGHT is primarily expressed on activated T cells, NK cells, and immature dendritic cells, and serves to regulate various aspects of immune responses. LIGHT is synthesized as a membrane-bound protein, but its cell-surface expression is regulated by several posttranslational mechanisms. LIGHT is cleaved from the cell surface by matrix metalloproteinases within minutes of its expression and accumulates as a soluble molecule (isoform 1; represents approximately residues 83-240; Swiss-Prot O43557-1). The cell surface cytoplasmic segment represents isoform 2 (Swiss-Prot O43557-2). Additionally, various cell types store LIGHT in vesicles and excrete them upon activation by various physiological stimuli. Although the role of the soluble form of LIGHT is not well characterized, it may serve as a negative feedback loop to inhibit the function of the membrane-bound form by competing for HVEM and LTβR.

LIGHT interacts with three different receptors: (1) herpesvirus entry mediator (HVEM) on T cells, (2) LTβR which is expressed primarily on epithelial and stromal cells, and (3) the soluble decoy receptor 3 on various cells. These interactions endow LIGHT with different functions. Interaction with LTβR on stromal cells is associated with the production of various cytokines/chemokines, lymph node (LN) organogenesis, and restoration of secondary lymphoid structures. On the other hand, interaction of LIGHT with HVEM receptor on lymphocytes results in activation and production of cytokines, dominated by IFN-γ and GM-CSF. In this context, the LIGHT/HVEM axis appears to deliver costimulatory signals associated with the activation of Th1 type responses which play critical roles in tumor eradication.

LIGHT plays a role in lymphoid organogenesis and in the generation of Th1 type responses. See, e.g., Yang et al., 2002, *J. Biol. Regul. Homeost. Agents,* 16:206-10; Schneider et al., 2004, *Immunol. Rev.,* 202:49-66.

The effect of LIGHT has been shown in different tumor models both in vitro and in vivo. Chronic lymphocytic leukemic cells transduced by herpes simplex virus amplicon expressing LIGHT have been reported to enhance T cell proliferation in mixed lymphocyte reactions. Over-expression of LIGHT on MDA-MB-231 human breast cancer cells has been shown to suppress tumor growth. Transfection of LIGHT into different cancer cell lines stimulate ICAM-1 expression in these cells. The presence of ICAM-1 is believed to be beneficial as it enables effective signaling to produce antitumor activity in tumor cells. Another important function of LIGHT, besides T cell activation, is its ability to transduce signals through LTβR, which plays an important role in the development of secondary lymphoid structures mediated through the induction of chemokine expression as well as adhesion molecules in stromal cells. The interaction of LIGHT with LTβR on stromal cells regulates the expression of CCL21, which control the homing of naïve T cells to lymphoid tissues.

One advantage of embodiments of the invention where the immune co-stimulatory polypeptide is LIGHT is the ability of LIGHT to stimulate lymphoid organogenesis and support the generation of Th1 type responses. Another advantage is the ability of LIGHT to stimulate immune responses against tumors and activate the tumor stroma to further augment these responses.

The stroma serves as a physical barrier to prevent lymphocyte infiltration into the tumor site. The stroma also inhibits lymphocyte activation within the tumor microenvironment.

This may be due to the lack of costimulatory signals needed for T cell activation and/or the presence of various immunoinhibitory soluble mediators, such as TGF-β and IL-10, that are synthesized and secreted by both stromal fibroblasts and tumor cells. The stroma promotes immunological ignorance by confining tumor cells to the tumor site, thereby preventing them from trafficking to the regional lymph nodes.

Tumor stromal cells also express various immunological receptors, such as LTβR, that can be exploited for the enhancement of anti-tumor immunity in accordance with the present invention.

4. OX40L

OX40L is expressed by dendritic cells and other APC and binds to OX40 which is present on activated T cells. OX40L contains 183 amino acids (21950 Da). See Miura et al. Mol. Cell. Biol. 11:1313-1325 (1991). The full amino acid sequence of OX40L can be found under accession no. P23510 in the Swiss-Prot database. OX40L is a type II glycoprotein with a cytoplasmic domain at residues 1-23, a transmembrane domain at residues 24-50 and an extracellular domain at residues 51-183. The nucleotide sequence of OX40L is 3510 bp, with the coding sequence being 157-708 (see Genbank accession no. NM_003326.2). Residues 51-183, or fragments thereof of OX40L that can bind to its cognate receptor OX40, can be linked or expressed as a C-terminal fusion to a binding pair member for use in accordance with the present invention.

5. CD40L

CD40L is expressed by activated T cells and also exists as an extracellular soluble form which derives from the membrane form by proteolytic processing. CD40L (a.k.a. TNFSF5) contains 261 amino acids (29350 Da). See Villinger et al. Immunogenetics 53:315-328 (2001). The full amino acid sequence of CD40L can be found under accession no. Q9BDN3. CD40L is a type II glycoprotein with a cytoplasmic domain at residues 1-22, a transmembrane domain at residues 23-43 and an extracellular domain at residues 44-261. The nucleotide sequence of CD40L is 1834 bp, with the coding sequence being 73-858 (see Genbank accession no. NM_000074). Residues 44-261, or fragments thereof of CD40L that can bind to its cognate receptor CD40, can be linked or expressed as an N-terminal fusion to a binding pair member for use in accordance with the present invention.

6. PD-L1

PD-L1 is expressed on activated T and B cells, dendritic cells, keratinocytes and monocytes. PD-L1 (a.k.a. B7-H; B7H1; PDL1; PDCD1L1) contains 290 amino acids (33275 Da). See Dong et al. Nat. Med. 5: 1365-1369 (1999). The full amino acid sequence of PD-L1 can be found under accession no. Q9NZQ7 in the Swiss-Prot database. PD-L1 contains 290 amino acids of which 18 amino acids at the N terminus represent the signal sequence. The extracellular domain is located at amino acids 19-238, a transmembrane domain is located at resides 239-259 and a cytoplasmic domain is located at residues 260-290. The nucleotide sequence of PD-L1 (1553 bp) is available in public databases (see Genbank accession no. NM_014143) (coding sequence is 53-925). Isoforms of PD-L1 exist by way of alternative splicing. The extracellular domain or fragments thereof of PD-L1 that can bind to its cognate receptor PDCD1, can be linked or expressed as an N-terminal fusion to a binding pair member for use in accordance with the present invention.

7. GL50

GL50 isoform 1 is widely expressed (brain, heart, kidney, liver, lung, pancreas, placenta, skeletal muscle, bone marrow, colon, ovary, prostate, testis, lymph nodes, leukocytes, spleen, thymus and tonsil); GL50 isoform 2 (swissprot O75144) is expressed in lymph nodes, leukocytes and spleen and on activated monocytes and dendritic cells. GL50 (a.k.a. B7-H2; B7H2; B7RP-1; B7RP1; ICOS-L; ICOSLG; KIAA0653; and LICOS) contains 290 amino acids (33275 Da). See Wang et al. Blood 96:2808-2813 (2000). The full amino acid sequence of GL50 can be found under accession no. O75144 in the Swiss-Prot database. GL50 contains 302 amino acids of which 18 amino acids at the N terminus represent the signal sequence. The extracellular domain is located at amino acids 19-256, a transmembrane domain is located at resides 257-277 and a cytoplasmic domain is located at residues 278-302. The nucleotide sequence of GL50 (3239 bp) is available in public databases (see Genbank accession no. NM_015259) (coding region representing 135-1043). Isoforms of GL50 exist by way of alternative splicing. The extracellular domain or fragments thereof of GL50 that can bind to its cognate receptor ICOS, can be linked or expressed as an N-terminal fusion to a binding pair member for use in accordance with the present invention.

Table 1 summarizes various exemplary costimulatory molecules and their receptors and includes embodiments of coreceptor ligand pair conjugates.

TABLE 1

| Construct name and orientation | Receptor | Receptor expression |
|---|---|---|
| CD80-CSA | CD28 | Constitutive on almost all human CD4 T cells and approximately 50% of CD8 T cells |
| GL50-CSA | ICOS | Detectable on resting T cells<br>Upregulated on activated CD4$^+$ T and CD8$^+$ T cells and NK cells |
| PD-L1-CSA | PD-1 | Inducible on CD4$^+$ and CD8$^+$ T cells, B cells, and monocytes<br>Low levels on NK-T cells |
| CSA-CD40L | CD40 | Constitutive on B cells, monocytes, DC, endothelial and epithelial cells |
| CSA-4-1BBL | CD137 | Inducible on activated T cells (peak 48 h, decline 96 h) as well as cytokine-treated NK cells<br>Constitutive on subsets of DC (low), human monocytes, follicular DC, CD4$^+$ CD25$^+$ regulatory T cells. |
| CSA-OX40L | OX40 | Inducible on activated CD4 (preferentially) and CD8 (strong antigen response) T cells (peak 48 h, decline 96 h) |
| CSA-LIGHT | HVEM | Constitutive on resting T cells, monocytes, and immature DC<br>Downregulated upon T cell activation and DC maturation |

Other immune co-stimulatory polypeptides can be used in accordance with the invention. For example US 2003/0219419 (the entire contents of which are incorporated herein by reference in their entirety) describes IL-2-CSA fusion proteins, and CSA-CD40L fusion proteins that are useful in the present invention. In summary, exemplary immune co-stimulatory polypeptides useful in accordance with the present invention include the following.

TABLE 2

| B7 and CD28 FAMILY MEMBERS | |
|---|---|
| LIGAND | RECEPTOR |
| CD80 (B7.1) | CD28, CTLA-4 (CD152) |
| CD86 (B7.2) | CD28, CTLA-4 |
| ICOSL (B7h, B7-H2, B7RP-1, GL50, LICOS) | ICOS (AILIM) |
| PD-L1 (B7-H1) | PD-1 |
| PD-L2 (B7-DC) | PD-1 |
| B7-H3 | Unknown |

TABLE 2-continued

B7 and CD28 FAMILY MEMBERS

| LIGAND | RECEPTOR |
|---|---|
| B7-H4 (B7x; B7S1) | Unknown (BTLA?) |
| Unknown (HVEM*) | BTLA |

*it is a TNF member

TABLE 3

TNF FAMILY MEMBERS

| LIGAND | RECEPTOR |
|---|---|
| OX40L | OX40 (CD134) |
| 4-1BBL | 4-1BB (CD137) |
| CD40L (CD154) | CD40 |
| CD27L (CD70) | CD27 |
| CD30L | CD30 |
| LIGHT | HVEM, LTβR, DcR3 |
| GITRL | GITR |
| BAFF (BLyS)** | BAFF-R, TACI, BCMA |
| APRIL** | TACI, BCMA |

**these are B cell related

TABLE 4A

References for nucleotide and/or amino acid sequences of B7 Family Members

| LIGAND (Human) | REFERENCE |
|---|---|
| CD80 (B7.1) | Freeman et al., J. Immunol. 143: 2714-2722(1989). |
| CD86 (B7.2) | Freeman et al., Science 262: 909-911(1993). |
| ICOSL | Wang et al., Blood 96: 2808-2813(2000). |
| | Yoshinaga et al., Int. Immunol. 12: 1439-1447(2000). |
| PD-L1 | Dong et al., Nat. Med. 5: 1365-1369(1999). |
| | Freeman et al., J. Exp. Med. 192: 1027-1034(2000). |
| PD-L2 | Tseng et al., J. Exp. Med. 193: 839-846(2001). |
| | Latchman et al., Nat. Immunol. 2: 261-268(2001). |
| B7-H3 | Steinberger et al., Submitted (SEP-2003) to EMBL/GenBank/DDBJ databases. |
| | Mingyi et al., J. Immunol 168: 6294-6297(2002). |
| B7-H4 | Zang et al., Proc. Natl. Acad. Sci. U.S.A. 100: 10388-92(2003). |
| (B7x; B7S1) | Sica et al., Submitted (APR-2003) to EMBL/GenBank/DDBJ databases. |

TABLE 4B

References for nucleotide and/or amino acid sequences of TNF Family Members

| LIGAND | REFERENCE |
|---|---|
| OX40L | Baum et al., Circ. Shock 44: 30-34(1994). |
| | Miura et al., Mol. Cell. Biol. 11: 1313-1325(1991). |
| | Godfrey et al., J. Exp. Med. 180: 757-762(1994). |
| 4-1BBL | Alderson et al., Eur. J. Immunol. 24: 2219-2227(1994). |
| CD40L | Graf et al., Eur. J. Immunol. 22: 3191-3194(1992). |
| | Hollenbaugh et al., EMBO J. 11: 4313-4321(1992). |
| CD27L (CD70) | Goodwin et al., Cell 73: 447-456(1993). |
| CD30L | Smith et al., Cell 73: 1349-1360(1993). |
| LIGHT | Mauri et al., Immunity 8: 21-30(1998). |
| GITRL | Gurney et al., Curr. Biol. 9: 215-218(1999). |
| BLyS | Moore et al., Science 285: 260-263(1999). |
| APRIL | Hahne et al., J. Exp. Med. 188: 1185-1190(1998). |

Antigens & Infectious Agents

The methods and compositions of the invention are useful for generating or enhancing an immune response against any antigen or infectious agent, including TAAs, antigens associated with an infectious agent, and an infectious agent itself. In accordance with the invention, an antigen associated with the targeted tumor or infectious agent (or the infectious agent itself) is presented to immune cells, thereby generating or enhancing an immune response.

1. TAAs

In one embodiment, the antigen is a TAA, and the invention provides cancer immunotherapy methods effective to generate or enhance a patient's immune response against a tumor. In accordance with this embodiment, the invention provides methods of reducing tumor size and methods of inhibiting the growth of tumor cells.

Representative tumor cells against which this invention is useful include, without limitation, carcinomas, which may be derived from any of various body organs including lung, liver, breast, bladder, stomach, colon, pancreas, skin, and the like. Carcinomas may include adenocarcinoma, which develop in an organ or gland, and squamous cell carcinoma, which originate in the squamous epithelium. Other cancers that can be treated include sarcomas, such as osteosarcoma or osteogenic sarcoma (bone), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), an esenchymous or mixed mesodermal tumor (mixed connective tissue types). In addition myelomas, leukemias, and lymphomas are also susceptible to treatment.

A number of TAAs associated with specific tumor types have been identified. These include human telomerase reverse transcriptase (hTERT), survivin, MAGE-1, MAGE-3, human chorionic gonadotropin, carcinoembryonic antigen, alpha fetoprotein, pancreatic oncofetal antigen, MUC-1, CA 125, CA 15-3, CA 19-9, CA 549, CA 195, prostate-specific antigens; prostate-specific membrane antigen, Her2/neu, gp-100, mutant K-ras proteins, mutant p53, truncated epidermal growth factor receptor, chimeric protein $p^{210}$BCR-ABL; E7 protein of human papilloma virus, and EBNA3 protein of Epstein-Barr virus. Any of these antigens, antigenic fragments thereof, and mixtures of antigens and/or fragments can be used in accordance with the invention to generate or enhance a patient's anti-tumor immune response. Table 5 lists some exemplary TAAs and diseases associated with such TAAs.

TABLE 5

| Antigen | Diseases |
|---|---|
| cTAGE-1 and variants | Cutaneous T cell lymphoma |
| BLA or globotriaosylceramide ($P^k$ antigen) | Burkitt's lymhoma |
| human T-cell leukemia virus-associated cell membrane antigens (HTLV-MA) | Adult T-cell leukemia'lymphoma (ATL) |
| Thymocyte surface antigen JL1 | Majority of acute leukemias |
| Adult T cell leukemia associated, human retrovirus associated antigen (ATLA) | Adult T cell leukemia |
| Epstein-Barr virus (EPV) antigens | Burkitt's lymphoma, Hodgkin's disease |
| Anaplastic lymphoma kinase (ALK), fusion proteins (NPM/ALK and variants) | CD30+ anaplastic large cell lymphoma (ALCL) |
| Common acute lymphoblastic leukemia antigen (CALLA) | Most acute lymphoblastic leukemias |

TABLE 5-continued

| Antigen | Diseases |
| --- | --- |
| Immunoglobulin Id; Type II glycoproteins (e.g., HM1.24; KW-2, KW-4, KW-5, KW-12); Oncofetal antigen immature laminin receptor protein (OFA-iLRP); EBV proteins (e.g., LMP2A) | Lymphoproliferative diseases |

Additional human TAAs recognized by T-cells may be found in, for example, Novellino et al. "A listing of human tumor antigens recognized by T cells: March 2004 update" *Cancer Immunology and Immunotherapy*, 54: 187-207 (2005) which is incorporated by reference herein. Many animal TAAs corresponding to animal correllaries of these diseases, and to other animal diseases, are known in the art and also included within the scope of the invention.

In one embodiment of the invention, the TAA is selected from the group consisting of human telomerase reverse transcriptase (hTERT) and survivin as TAAs. hTERT is expressed in >85% of human cancers, while its expression is restricted in normal tissues. See, e.g., Vonderheide et al., Immunity 1999, 10: 673-79. Similarly, survivin, which has been identified as an inhibitor of apoptosis, is absent from normal tissues but expressed in most tumor types including lung, colon, pancreas, prostate and breast cancer. See, e.g., Ambrosini et al., Nat. Med. 1997, 3: 917-21. Because these TAAs are expressed in the majority of cancer types and are rare or absent from normal tissues, they are attractive antigens for use in cancer immunotherapy methods according to the present invention.

In another embodiment of the invention, the TAA is associated with cervical cancer. Approximately 500,000 women worldwide develop cervical cancer yearly and it is the second leading cause of death from cancer in women. Cervical cancer has been directly linked to genital viral infection by human papillomavirus (HPV) and is a worldwide health problem. HPV type 16 in particular is found in roughly half of cervical cancers. Genital HPV types 16 and 18, and less frequently, types 31, 33, 35, 45, 51 and 56, also have been implicated in the etiology of cervical and other anogenital cancers. The HPV types found in cancer cells have transforming activity in in vitro studies and the viral transforming proteins, E6 and E7 (also known as "early" proteins), are consistently expressed in cervical cancer cell lines and in HPV-associated cancers. E6 and E7 are known to bind the tumor suppressors, p53 and retinoblastoma (Rb), respectively. In HPV-associated malignant transformation, late genes (L1 and L2) and some early genes (E1 and E2) are usually lost, leaving E6 and E7 as the only open reading frames frequently found in carcinomas. Expression of E6 and E7 is likely to overcome the regulation of cell proliferation normally mediated by proteins like p53 and Rb, allowing uncontrolled growth and providing the potential for malignant transformation.

Thus, in accordance with one specific embodiment of the invention, the TAA is one or more of E6 and E7. The use of E6 and E7 in accordance with the invention may offer several advantages. First, E6 and E7 are consistently expressed in most cervical cancers. Second, while most tumor antigens are derived from normal proteins or mutated self-protein, E6 and E7 are completely foreign viral proteins, and may harbor more antigenic peptides or epitopes than a mutant protein. Third, E6 and E7 play an important role in the induction and maintenance of the malignant phenotype, and without functional E6 and E7, these cells would cease to be tumorigenic.

The nucleotide and amino acid sequences of the E6 and E7 proteins from different species (e.g., human, bovine) and for different papillomavirus types (e.g., HPV16 and 18) are known in the art. See, e.g., the HPV sequence database at http://www.stdgen.lanl.gov/stdgen/virus/hpv/index.html.

The amino acid sequences of HPV16 E6, an HPV16 E6 variant, and E7 are set forth in FIGS. 6A (SEQ ID NO:11), 6B (SEQ ID NO:12) and 6C (SEQ ID NO:13), respectively.

2. Infectious Agents

Representative infectious agents against which this invention is useful include, without limitation, any virus, bacteria, fungi or protozoan. Table 6 lists examples of infectious agents.

TABLE 6

| | ETIOLOGICAL AGENT | GENUS | ASSOCIATED DISEASE |
| --- | --- | --- | --- |
| BACTERIAL | *Mycobacterium tuberculosis* | | Tuberculosis |
| | *Bacillus anthracis* | | Anthrax |
| | *Staphylococcus aureus* | | Sepsis |
| VIRAL | Adenoviridae | Mastadenovirus | I fectious canine hepatitis |
| | Arenaviridae | Arenavirus | Lymphocytic choriomeningitis |
| | Caliciviridae | Norovirus | Norwalk virus infection |
| | Coronaviridae | Coronavirus | Severe Acute Respiratory Syndrome |
| | | Torovirus | |
| | Filoviridae | Marburgvirus | Viral hemorrhagic fevers |
| | | Ebolavirus | Viral hemorrhagic fevers |
| | Flaviviridae | Flavivirus | West Nile Encephalitis |
| | | Hepacivirus | Hepatitis C virus infection |
| | | Pestivirus | Bovine Virus Diarrhea, Classical swine fever |
| | Hepadnaviridae | Orthohepadnavirus | Hepatitis |
| | Herpesviridae | Simplexvirus | cold sores, genital herpes, bovine mammillitis |
| | | Varicellovirus | chickenpox, shingles, abortion in horses, encephalitis in cattle |
| | | Cytomegalovirus | infectious mononucleosis |
| | | Mardivirus | Marek's disease |
| | Orthomyxoviridae | Influenzavirus A | Influenza |
| | | Influenzavirus B | Influenza |
| | Papillomaviridae | Papillomavirus | Skin warts, skin cancer, cervical cancer |
| | Picornaviridae | Enterovirus | Polio |
| | | Rhinovirus | Common cold |
| | | Aphthovirus | Foot-and-mouth disease |
| | | Hepatovirus | Hepatitis |
| | Poxviridae | Orthopoxvirus | Cowpox, vaccinia, smallpox |
| | Reoviridae | Rotaviruses | Diarrhea |
| | | Orbivirus | Blue tongue disease |

TABLE 6-continued

| ETIOLOGICAL AGENT | GENUS | ASSOCIATED DISEASE |
|---|---|---|
| | Retroviridae Gammaretrovirus | Feline leukemia |
| | Deltaretrovirus | Bovine leukemia |
| | Lentivirus | Human immunodeficiency, FIV, and SIV |
| | Rhabdoviridae Lyssavirus | Rabies |
| | Ephemerovirus | Bovine ephemeral fever |
| | Togaviridae Alphavirus | Eastern and Western equine encephalitis |
| PARASITIC | *Plasmodium* | Malaria |
| | *Leishmania* | Leishmaniasis |
| FUNGAL | *Aspergillis* | |
| | *Candida* | |
| | *Coccidia* | |
| | *Cryptococci* | |
| | *Geotricha* | |
| | *Histoplasma* | |
| | *Microsporidia* | |
| | *Pneumocystis* | |

Human and avian influenza, HIV, hepatitis C, tuberculosis, west nile virus, cryptococosis (meningitis) herpes, chlamydia, and anthrax are representative of infectious agents. Any antigen associated with the infectious agent can be used in accordance with the invention.

In accordance with one embodiment, the infectious agent itself is used in a conjugate according to the invention. In accordance with this embodiment, a conjugate comprising the infectious agent, such as a virus, and a binding pair member is used. Any infectious agent may be used, such as a virus, including a human or avian influenza virus or HIV, or any other virus. The infectious agent may be modified or attenuated to reduce or eliminate its infectivity.

For the purpose of illustration only, this aspect of the invention is described in more detail with reference to influenza. Influenza is a contagious disease caused by the influenza virus, and affects the respiratory tract, often resulting in symptoms in the nose, throat and lungs, as well as fever, headache, tiredness and aches. It can also lead to complications such as pneumonia, bronchitis, or sinus and ear infections or exacerbate chronic conditions. Influenza viruses are classified as type A, B or C. Strains belonging to types A and B circulate in the population and are associated with most cases of human influenza. Type A influenza causes the overwhelming majority of public health problems in humans.

Type A influenza viruses are subtyped depending on the composition of two of its proteins; hemagglutinin (H), a protein that facilitates binding and entry of the virus into the target cell, and neuraminidase (N), a protein involved in the release of newly formed virus particles from infected cells and spreading it through the body. Fifteen hemagglutinin subtypes (H1-H15) and 9 neuraminidase subtypes (N-1-N9) have been identified. Large outbreaks of influenza in humans have been caused by three hemagglutinin subtypes (H1, H2 and H3) and two neuraminidase subtypes (N1 and N2). For example, the hemagglutinin of the 1918 flu virus was H1, its neuraminidase was N1, so it is designated as an H1N1 subtype. Other outbreaks have included the H2N2 subtype in 1957, H3N2 in 1968, and H5N1 in the recent outbreaks in birds and humans in Southeast Asia, China, and now Europe and the Middle East.

Influenza A viruses constantly evolve by mechanisms which involve mutations or changes in the reactive or antigenic sites of hemagglutinin and neuraminidase, or by the sudden replacement of one hemagglutinin or neuraminidase subtype by another subtype. These mechanisms result in new virus subtypes and allow the influenza virus to evade the defenses of the immune system and spread. Antigenic variants of influenza A viruses emerge every year and demand an updated vaccine formulation based on ongoing international surveillance of influenza virus by the World Health Organization. Due to this phenomenon in which new influenza virus subtypes constantly emerge, such as H5N1 in recent years, more major outbreaks of influenza are expected to occur. In certain plausible bioterrorism scenarios, laboratory-derived viruses would similarly be designed to effect antigenic changes and hence to cause outbreaks that would evade established host defenses.

The conjugates of the present invention can be used in influenza vaccines that are easy to produce and manufacture quickly, whose antigenic component can be changed and updated based on the current health needs without difficulty, that selectively targets viral machinery and infected cells, and that can be administered post-infection for a therapeutic effect as well as pre-infection for prevention.

Thus, in accordance with one embodiment, an influenza antigen (or antigenic fragment thereof) is used as the antigen component of a conjugate of the present invention. For example, the antigen may comprise one or more of H1 and N1 (both highly immunogenic) and/or one or more of nucleoprotein (NP) and matrix protein 1 (MP1) and/or matrix protein 2 (MP2) (all highly conserved, structural proteins). Proteins from pandemic strains such as H5, also can be used as antigens in accordance with the invention. While not wanting to be bound by any theory, intracellular proteins such as NP and MP2 may provide a more universal vaccine because they exhibit little or no variance and therefore may prevent heterologous viral infections without the need for annual adjustment. For example, NP exhibits >90% protein sequence homology among influenza A isolates and contains dominant cytotoxic T cell target epitopes. Other influenza antigens useful in the present invention include PA, PB1 and PB2 (RNA polymerase subunits) and NS1 and NS2 (interferon response inhibitor and RNP nuclear export). See also, Brown, 2000, Biomed. Pharmacother. 54: 196-209; Steinhauer et al., 2002, 36: 305-32; De Jong et al., 2000, 40: 218-28; Alexander, Vet. Microbiol. 74: 3-13.

Thus, in accordance with one embodiment, a Type A influenza hemagglutinin protein (or antigenic fragment thereof) is used as the antigen component of a conjugate of the present invention. Currently the prevention of influenza is achieved by subcutaneous injection of an influenza vaccine with H as the major component. For example, H1 from influenza virus A/PuertoRico/8/34 (PR8) (H1N1) is the predominant, circulating H protein and has been well-characterized, and can be used in accordance with the invention. In another embodiment, a Type A influenza neuraminidase protein (or antigenic fragment thereof) is used as the antigen component of the conjugate. A composition comprising either an H protein-containing conjugate or an N protein-containing conjugate is useful as a vaccine against influenza. (For example, current influenza vaccines comprise an H protein as the major component, and have been shown to induce sufficient immunity to prevent an epidemic of homologous virus.) Alternatively, it may be advantageous to administer both a conjugate comprising an H protein and a conjugate comprising an N protein, or any combination of antigens, such as a combination of variable and conserved antigens. This could be effected by administering two or more compositions, each comprising a single antigen-containing conjugate, or by providing two or more conjugates (and, therefore, two or more antigens) in a single composition. In one embodiment, the antigen components of the conjugate(s) are chosen based on current public health needs.

In one embodiment, the conjugate comprises 4-1BBL as the immune co-simulatory polypeptide. While not wanting to be bound by any theory, it is believed that this conjugate, when administered to a patient in vivo, will bind to DCs through the interaction between 4-1BBL and the 4-1BB receptor on DCs, resulting in internalization of the vaccine and presentation of the influenza antigen on the surface of the DC, as well as activation and maturation of DCs. Activation of the DC may in turn lead to interaction with and activation of CD8 and CD4 T cells. Activated CD4 T cells may then interact with B cells and cause their activation and differentiation into antibody secreting cells, leading to a humoral response. Activation of CD8 T cells also may lead to differentiation and proliferation of more CD8 T cells which function to kill virus-infected cells. The conjugate also may bind directly to activated CD8 and CD4 T cells expressing the 4-1BB receptor, further amplifying the signal. In addition, the conjugate (via 4-1BBL) may bind directly to activated natural killer (NK) cells, which also function to kill virus-infected cells, all of which results in a more robust immune response. Thus, the conjugate will generate both cellular and humoral responses that support its efficacy in therapeutic and prophylactic vaccines.

The antigen components of conjugates useful as vaccines against other infectious agents can be selected in an analogous manner by those skilled in the art, based on the antigens associated with those infectious agents. For example, antigens associated with HIV include HIV envelope gp120 epitopes (e.g, variable loops such as V3), or other HIV proteins such as Gag proteins ($Pr55^{gag}$, matrix p17, capsid p24, nucleocapsid p7), p5; Pol (polymerase), Vif (viral infectivity factor p23); Vpr (viral protein R p15); Rev (regulator of viral gene expression p19); Vpu (viral protein U); Env (gp 160, gp120, gp41); Tat (trancripinal activator p14); and Nef (gegative effector p24). See, e.g., Peters, 201, Vaccine 2: 688-705; Michael, 2003, Clin. Med. 3: 269-72; Gandhi & Walker, 2002, Ann. Rev. Med. 53: 149-72; Haseltine, 1991, FASEB 5: 2349-60. Other antigens useful in vaccines include capsular polysaccharides of *Haemophilus influenzae* type b, capsusalr polysaccharides of *Neisseria meningitidis*, capsusalr polysaccharides of *Streptococcus pneumoniae*, surface antigens of Hepatitis B, and inactivated exotoxins of diphtheria and tetanus toxins. These antigens can be used in accordance with the present invention as described above with reference to influenza antigens.

Binding Pairs

An exemplary binding pair is biotin and streptavidin (SA) or avidin. SA or avidin fragments which retain substantial binding activity for biotin, such as at least 50% or more of the binding affinity of native SA or avidin, respectively, also may be used. Such fragments include "core streptavidin" ("CSA") a truncated version of the full-length streptavidin polypeptide which may include streptavidin residues 13-138, 14-138, 13-139 and 14-139. See, e.g., Pahler et al., J. Biol. Chem. 1987, 262:13933-37. Other truncated forms of streptavidin and avidin that retain strong binding to biotin also may be used. See, e.g. Sano et al., J Biol. Chem. 1995 Nov. 24, 270(47): 28204-09 (describing core streptavidin variants 16-133 and 14-138) (U.S. Pat. No. 6,022,951). Mutants of streptavidin and core forms of strepavidin which retain substantial biotin binding activity or increased biotin binding activity also may be used. See Chilcoti et al., Proc Natl Acad Sci USA. 1995 Feb. 28; 92(5):1754-8; Reznik et al., Nat. Biotechnol. 1996 August; 14(8):1007-11. For example, mutants with reduced immunogenicity, such as mutants mutated by site-directed mutagenesis to remove potential T cell epitopes or lymphocyte epitopes, can be used. See Meyer et al., Protein Sci. 2001 10: 491-503. Likewise, mutants of avidin and core forms of avidin which retain substantial biotin binding activity or increased biotin binding activity also may be used. See Hiller et al., J. Biochem. (1991) 278: 573-85; Livnah et al. Proc Natl Acad Sci USA (0: 5076-80 (1993). For convenience, in the instant description, the terms "avidin" and "streptavidin" as used herein are intended to encompass biotin-binding fragments, mutants and core forms of these binding pair members. Avidin and streptavidin are available from commercial suppliers. Moreover, the nucleic acid sequences encoding streptavidin and avidin and the streptavidin and avidin amino acid sequences can be found, for example, in GenBank Accession Nos. X65082; X03591; NM_205320; X05343; Z21611; and Z21554.

As used herein "biotin" includes biotin-containing moieties that are able to bind to surfaces, such as cell surfaces (including tumor cell surfaces), such as NHS-biotin and EZ-Link™ Sulfo-NHS-LC-Biotin (Pierce). Such protein reactive forms of biotin are available commercially.

The interaction between biotin and its binding partner, avidin or streptavidin, offers several advantages in the context of the present invention. For example, biotin has an extremely high affinity for both streptavidin ($10^{13}$ $M^{-1}$) and avidin ($10^{15}$ $M^{-1}$). Additionally, both streptavidin and avidin are tetrameric polypeptides that each bind four molecules of biotin. Immune co-stimulatory moieties comprising streptavidin or avidin therefore have a tendency to form tetramers and higher structures. As a result, they can cross-link their corresponding immune cell receptors for more potent signal transduction, such as through aggregation of receptors.

Those skilled in the art will recognize that other mechanisms (e.g., other conjugation methods using, for example, other linking moieties or chemical or genetic cross-linking) can be used to provide higher-order structures of immune co-stimulatory molecules, such as conjugates comprising dimers, trimers, tetramers and higher-order multimers of immune co-stimulatory molecules, which also will exhibit advantageous properties. Such conjugates are included within the scope of this invention.

Conjugates

A conjugate comprising an immune co-stimulatory polypeptide, antigen, or infectious agent and a member of a binding pair can be made by methods well known in the art. For example, the polypeptide/antigen/infectious agent and binding pair member can be covalently bound to each other or conjugated to each other directly or through a linker. In accordance with one embodiment, the polypeptide/antigen/infectious agent and binding pair member are components of a fusion protein. Fusion proteins can be made by any of a number of different methods known in the art. For example, one or more of the component polypeptides of the fusion proteins can be chemically synthesized or can be generated using well known recombinant nucleic acid technology. (As used herein, "nucleic acid" refers to RNA or DNA.) Nucleic acid sequences useful in the present invention can be obtained using, for example, the polymerase chain reaction (PCR). Various PCR methods are described, for example, in *PCR Primer: A Laboratory Manual*, Dieffenbach 7 Dveksler, Eds., Cold Spring Harbor Laboratory Press, 1995.

In accordance with one embodiment, an immune co-stimulatory polypeptide is bound via its C-terminus to the N-terminus the binding pair member. For example, an immune co-stimulatory polypeptide can be bound via its C-terminus to the N-terminus of core streptavidin (CSA). Thus the invention includes CD80-CSA fusion proteins, where the CD80 moiety is bound via its C-terminal to the N-terminal of CSA. In accordance with another embodiment, the immune co-stimulatory polypeptide is bound via its N-terminus to the C-terminus of the binding pair member. For example, an immune co-stimulatory polypeptide can be bound via its N-terminus to the C-terminus of CSA. For example, the invention includes CSA-4-1BBL, CSA-LIGHT, CSA-CD40L, and CSA-OX40L fusion proteins, where the CSA moiety is bound via its C-terminal to the N-terminal of the immune co-stimulatory polypeptide. The immune co-stimulatory polypeptide may be directly bound to the binding pair member or may be bound via one or more linking moieties, such as one or more linking polypeptides.

In accordance with one embodiment, the immune co-stimulatory polypeptide, antigen or infectious agent is biotinylated. Biotinylated conjugates can be made by methods known in the art, and exemplified below in the examples.

For example, Biotin AviTag technology from Avidity, Inc. (Denver, Colo.) can be used to generate biotinylated proteins or infectious agents. The Biotin AviTag is comprised of a unique 15 amino acid peptide that is recognized by biotin ligase, BirA, that attaches biotin to a lysine residue in the peptide sequence. Schatz, 1993, *Biotechnology*, 11: 1138-43. The Biotin AviTag can be genetically fused to any protein of interest, allowing the protein to be tagged with a biotin molecule.

One potential drawback to the Biotin AviTag technology is the possibility of a low degree of biotinylation, because the system biotinylates the protein at a single, unique lysine residue in the tag region. To overcome any such problem, the purified tagged proteins can be modified in vitro using purified biotin ligase. Because the biotinylation is performed enzymatically, the reaction conditions are gentler, the labeling is highly specific, and the reaction is more efficient than chemical modification of the protein using biotin derivatives. Alternatively, the methods described in Jordan, et al, 2003, *Clin. Diag. Lab. Immunol.* 10: 339-44, can be used to produce a genetically engineered biotinylated protein.

Fragments of an immune co-stimulatory polypeptide, binding pair member antigen, or infectious agent are useful in the present invention, as long as the fragment retains the activity of the referent full-length moiety. Thus, for example, an immune co-stimulatory fragment should retain its immune co-stimulatory activity (e.g., retain its ability to bind its receptor or ligand), a binding member fragment should retain its ability to bind with its binding partner, and an antigen or infectious agent fragment should retain its ability to induce an immune response against the referent full-length antigen or infectious agent. Fragments can be screened for retained activity by methods that are routine in the art. Exemplary fragments of immune co-stimulatory polypeptides are set forth above.

The conjugates may include a linker such as a peptide linker between the binding pair member and the immune co-stimulatory polypeptide, antigen, or infectious agent. The linker length and composition may be chosen to enhance the activity of either or both functional ends of the conjugate (e.g., co-stimulatory polypeptide/antigen.infectious agent or binding pair member). The linker is generally from about 3 to about 15 amino acids long, more preferably about 5 to about 10 amino acids long, however, longer or shorter linkers may be used or the linker may be dispensed with entirely. Flexible linkers (e.g. (Gly$_4$Ser)$_3$) such as have been used to connect heavy and light chains of a single chain antibody may be used in this regard. See Huston, et al. (1988) *Proc. Nat. Acad. Sci. USA*, 85:5879-5883; U.S. Pat. Nos. 5,091,513, 5,132,405, 4,956,778; 5,258,498, and 5,482,858. Other linkers are FENDAQAPKS or LQNDAQAPKS. One or more domains of and immunoglobulin Fc region (e.g CH1, CH2 and/or CH3) also may be used as a linker. Chemical linkers also may be used.

Nucleic acids and polypeptides that are modified, varied, or mutated also are useful in the present invention, as long as they retain the activity of the referent nucleic acid or polypeptide. For example, nucleic acid and polypeptide sequences suitable for use in the present invention can have at least about 80% sequence identity (including at least 80% sequence identity) to a referent nucleic acid or polypeptide, i.e., to a nucleic acid encoding a known immune co-stimulatory polypeptide or binding pair member. In some embodiments, the nucleic acid sequence or polypeptide has at least about 85%, at least about 90%, at least about 95%, or at least about 99% sequence identity to the referent nucleic acid or polypeptide.

The invention encompasses nucleic acids with base changes that are "silent," in that they encode the same amino acid (i.e. degenerate nucleic acid sequences). The invention also encompasses nucleic acids that encode polypeptides with conservative amino acid substitutions, and such polypeptides. Conservative amino acid substitutions (for example, substituting one hydrophobic residue with a different hydrophobic residue) are well known in the art and can be effected, e.g., by point mutations and the like. The suitability of a given modified sequence, variant or mutant can be confirmed using receptor binding and/or biological screening methods that are known in the art, such as those discussed above with reference to fragments.

As used herein, "% sequence identity" is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in the aligned sequences. The total number of aligned nucleotides or amino acids refers to the minimum number of nucleotides or amino acids that are necessary to align the second sequence, and does not include alignment (e.g., forced alignment) with non-homologous sequences, such as those that may be fused at the N-terminal or C-terminal of the sequence of interest (i.e., the sequence encoding the immune co-stimulatory polypeptide or binding pair member). The total number of aligned nucleotides or amino acids may correspond to the entire coding sequence or may correspond to fragments of the full-length sequence as defined herein.

Sequences can be aligned using the using the algorithm described by Altschul et al. (1997, Nucleic Acids Res., 25:3389-3402) as incorporated into the BLAST (basic local alignment search tool) programs, available at ncbi.nlm.nih.gov on the World Wide Web. BLAST searches or alignments can be performed to determine percent sequence identity between a nucleic acid molecule (the "query sequence") and any other sequence or portion thereof using the Altschul algorithm. BLASTN can be used to align and compare the identity between nucleic acid sequences, while BLASTP can be used to align and compare the identity between amino acid sequences. When utilizing BLAST programs to calculate the percent identity between a nucleic acid sequence encoding a therapeutic polypeptide and another sequence, the default parameters of the respective programs can be used including the default for gap penalty.

Nucleic acids of the present invention may be detected by methods such as Southern or Northern blot analysis (i.e., hybridization), PCR, or in situ hybridization analysis.

Polypeptides are typically detected by immunocytochemistry in transfected cell lines or by sodium dodecyl sulphate (SDS)-polyacrylamide gel electrophoresis followed by Coomassie Blue-staining or Western blot analysis using antibodies (monoclonal or polyclonal) that have specific binding affinity for the particular polypeptide. Many of these methods are discussed in detail in Sambrook et al. (1989, Molecular Cloning: A Laboratory Manual, $2^{nd}$ Ed., Cold Spring Harbor Laboratory Press, Cold Spring Harbor, N.Y.).

Nucleic acid sequences encoding an immune co-stimulatory polypeptide and the binding pair member can be operably linked to one another in a construct using conventional molecular biology techniques. See, for example, *Molecular Cloning: A Laboratory Manual* (Sambrook et al., 2001, $2^{nd}$ Ed., Cold Spring Harbor Laboratory Press) or *Short Protocols in Molecular Biology* (Ausubel et al., 2002, $5^{th}$ Ed., Current Protocols). Constructs suitable for use in these methods are commercially available and used routinely in the art. Constructs can include elements necessary for expression such as promoter sequences, regulatory elements such as enhancer sequences, and response elements and/or inducible elements that modulate expression of a nucleic acid sequence. As used herein, "operably linked" refers to (i) positioning of a promoter and/or other regulatory element(s) relative to a nucleic acid sequence in such a way as to direct or regulate expression of the nucleic acid; and/or (ii) positioning the nucleic acid encoding the immune co-stimulatory polypeptide and the nucleic acid encoding the binding pair member, such that the coding sequences are "in frame," i.e., such that the construct encodes a fusion protein comprising the immune co-stimulatory polypeptide and the binding pair member.

A construct can be propagated or expressed to generate a polypeptide in a host cell by methods known in the art. As used herein, the term "host" or "host cell" is meant to include not only prokaryotes, such as *E. coli*, but also eukaryotes, such as yeast, insect, plant and animal cells. Animal cells include, for example, COS cells and HeLa cells. A host cell can be transformed or transfected with a DNA molecule (e.g., a construct) using any of the techniques commonly known to those of ordinary skill in this art, such as calcium phosphate or lithium acetate precipitation, electroporation, lipofection and particle bombardment. Host cells containing a vector of the present invention may be used for purposes such as propagating the vector, producing a nucleic acid (e.g., DNA or RNA), expressing an immune co-stimulatory polypeptide or fragments thereof, or expressing a fusion protein, as described above.

FIGS. 1A & 1B, 2A & 2B, 3A & 3B, 4A & 4B, 5A & 5B, and 7A & 7B show representative nucleic acid sequences (SEQ ID NOs. 1, 3, 5, 7, 9 & 14) that include coding sequences for immune co-stimulatory moieties that comprise core streptavidin and an immune co-stimulatory polypeptide, and the corresponding encoded amino acid sequences (SEQ ID NOs. 2, 4, 6, 8, 10 & 15).

Immunotherapy

One embodiment of the present invention provides a method of generating or enhancing an immune response against a first antigen or infectious agent by administering to a patient in need thereof (a) a first conjugate comprising (i) a conjugate member comprising a first immune co-stimulatory polypeptide and (ii) a conjugate member comprising a first member of a binding pair, and (b) a second conjugate comprising (i) a conjugate member comprising the first antigen or the infectious agent and (ii) a conjugate member comprising a second member of the binding pair. In an alternative embodiment, immune cells are treated with the first and second conjugates and then administered to the patient. As discussed above, any immune co-stimulatory polypeptide and any antigen associated with a tumor or infectious agent (or the infectious agent itself) may be used, as may any binding pair.

The present invention include the use of chimeric co-stimulatory molecules with and without conjugation to the antigen of interest.

In embodiments where the conjugates are administered directly to the patient, the first conjugate and the second conjugate can be administered at substantially the same time or at different times. In one embodiment, the conjugates are bound together via the binding activity of the binding pair members before administration to the patient. For example, the first and second conjugates can be combined in vitro and administered in a single composition. In another embodiment, the first conjugate is administered first, followed by administration of the second conjugate after a time sufficient for the immune co-stimulatory polypeptide to bind to immune cells. This time period, for example, may vary from one to a few hours, to from one day to a few days, to from one week or longer.

The first and second conjugates can be administered to the patient systemically or locally, such as by intravenous, intranasal, peritoneal, or subcutaneous injection. In one embodiment, one or more of the composition(s) are administered locally via direct injection into a tumor site, such as by intratumoral injection, or into a site of local infection. In another embodiment one or more of the compositions are administered by different routes. For example, or one or more compositions can be administered locally and one or more can be administered systemically.

In embodiments where the conjugates are use to treat immune cells which are then administered directly to patient, the immune cells can be treated with the first and the second conjugates at substantially the same time or at different times. In one embodiment, the first and second conjugates are bound together via the binding activity of the binding pair members before being used to treat immune cells. For example, the first and second conjugates can be combined in a single composition and used to treat immune cells in vitro, such as by contacting immune cells with the composition. In another embodiment, immune cells are treated with the first conjugate, followed after a period of time by treatment with the second conjugate. This time period, for example, may vary from one to a few hours, to from one day to a few days, to from one week or longer. The treated immune cells are administered to the patient by any means described above, including systemic or local administration, such as intratumoral injection or injection into a site of local infection.

In accordance with one embodiment, the method further comprises administering a third conjugate or treating immune cells with a third conjugate. In one embodiment, the third conjugate comprises (i) a conjugate member comprising an immune co-stimulatory polypeptide and (ii) a conjugate member comprising a second antigen associated with the tumor or infectious agent or the infectious agent itself. The immune co-stimulatory polypeptide of the third conjugate may be the same as or different from the immune co-stimulatory polypeptide of the first conjugate, and the second antigen may be the same as or different from the first antigen. In a specific aspect of this embodiment, the immune co-stimulatory polypeptide and second antigen are bound together via interactions of binding pair members associated with each of the immune co-stimulatory polypeptide and second antigen. In accordance with this embodiment, the first and second binding pair members of the third conjugate may be the same as or different from the first and second binding pair members of the first and second conjugates.

In one embodiment, the first conjugate comprises an immune co-stimulatory polypeptide that binds to a constitutive receptor, such as CD80, LIGHT, and CD40L, and the third conjugate comprises an immune co-stimulatory polypeptide that binds to an inducible receptor, such as 4-1BBL and OX40L.

Table 7 below provides a listing of costimulatory molecules that are constitutive and inducible.

TABLE 7

| Constitutive | Inducible |
|---|---|
| CD80-CSA | CSA-4-1BBL |
| CSA-CD40L | CSA-OX40L |
| CSA-LIGHT | PD-L1-CSA |
|  | GL50-CSA |

Efficacy of cancer immunotherapy can be assessed by determining the decrease in tumor cell proliferation and/or tumor size. The number of tumor cells is not static and reflects both the number of cells undergoing cell division and the number of cells dying (e.g., by apoptosis). Increasing an individual's immune response against tumor cells may inhibit proliferation of the cells. Proliferation of tumor cells as used herein refers to an increase in the number of tumor cells (in vitro or in vivo) over a given period of time (e.g., hours, days, weeks, or months). Inhibiting the proliferation of tumor cells can be measured by a decrease in the rate of increase in tumor cell number, a complete loss of tumor cells, or any decrease in proliferation therebetween. A decrease in the size of a solid tumor is an indication of an inhibition of proliferation of tumor cells.

The present invention offers an advantage over prior art cancer vaccines by providing the ability to target TAAs specifically to DCs through the interaction of the immune co-stimulatory polypeptide (such as 4-1BBL) with the its receptor. Moreover, the invention provides a vaccine that can be administered to a patient by injection and taken up by the DC in vivo, leading to antigen presentation and activation without requiring the isolation and ex vivo manipulation of DCs or the use of gene therapy.

Efficacy of immunotherapy against infection can be assessed by determining the patient's infection burden, and by assessing clinical endpoints, such as fever or swelling.

The use of avidin/biotin binding pairs in accordance with the invention (or other mechanisms for providing higher order structures of immune co-stimulatory molecules) offers the further advantage of providing a tetrameric structure (or other multimeric structure) that permits cross-linking of the immune co-stimulatory receptor for a stronger response and that permits delivery of multiple antigen molecules to DCs. In one embodiment, the first binding pair member, i.e., the binding pair member of the first conjugate (comprising the first immune co-stimulatory polypeptide) is avidin, streptavidin or core streptavidin, and the second binding pair member, i.e. the binding pair member of the second conjugate (comprising the first antigen or the infectious agent) is biotin. In another embodiment, the first binding pair member is biotin and the second binding pair member is avidin, streptavidin, or core streptavidin.

The use of 4-1 BBL as the immune co-stimulatory polypeptide may offer further advantages, because stimulation of DCs with 4-1BBL has been shown to nullify the suppressive function of $T_{reg}$ cells that play a dominant role in tumor evasion of the immune system. Thus, conjugates of the present invention comprising 4-1BBL and a TAA will deliver the TAA to DCs for effective presentation, activate DCs for the elaboration of various cytokines, and nullify the function of $T_{reg}$ cells while boosting the function of Teff and NK cells for tumor eradication.

Modified Immune Cells

The invention also provides modified immune cells, and methods of making them, that are useful in immunotherapy methods as described above. In accordance with this aspect of the invention, there is provided a method of modifying immune cells to generate or enhance an immune response to a tumor expressing a first tumor associated antigen or to an infectious agent. The method comprises contacting immune cells expressing a receptor for a first immune co-stimulatory polypeptide with (a) a first conjugate comprising (i) a conjugate member comprising the first immune co-stimulatory polypeptide and (ii) a conjugate member comprising a first member of a binding pair; and (b) a second conjugate comprising (i) a conjugate member comprising an antigen associated with the tumor or infectious agent or the infectious agent and (ii) a conjugate member comprising a second member of the binding pair. In accordance with this method, the first conjugate is conjugated to the immune cells via binding between the immune co-stimulatory polypeptide and the receptor, and the second conjugate is conjugated to the immune cell via binding between the first and second binding pair members.

The immune cells may be contacted with the first and second conjugates by any means, and this may be effected in vivo or in vitro. For example, an in vivo method may comprise administering the first and second conjugates to a patient comprising the immune cells and comprising or at risk of comprising the tumor or infectious agent. In accordance with this method, the first and second conjugates may be administered substantially simultaneously (in the same or separate compositions) or sequentially (in separate compositions). In one embodiment where the patient comprises a tumor, at least one of the first and second conjugates is administered by intratumoral injection.

An exemplary in vitro method may comprise contacting immune cells with the first and second conjugates in vitro, such as by contacting with a single composition comprising the first and second conjugates, or by contacting with first and second compositions comprising the first and second conjugates, respectively. When the conjugates are provided in a single composition, they may be bound together via binding between the first and second binding pair members, as provided in the composition.

Any immune co-stimulatory polypeptide, antigen or infectious agent, and binding pair members can be used in this aspect of the invention, including each described above.

Any immune cell expressing a receptor for the first immune co-stimulatory polypeptide can be modified in accordance with this method. In one embodiment, the immune cells are T cells or neutrophils. Exemplary T cells include CD4+ cells, CD8+ cells, natural killer cells, monocytes and dendritic cells.

In a further embodiment of this aspect of the invention, the immune cells comprises a receptor for a second immune co-stimulatory polypeptide, and the method further comprises contacting the immune cells with a third conjugate comprising (i) a first conjugate member comprising the second immune co-stimulatory polypeptide and (ii) a second conjugate member comprising a antigen associated with the tumor or infectious agent (or the infectious agent itself). In this embodiment, the second immune co-stimulatory polypeptide may be the same as or different from the first immune co-stimulatory polypeptide and the second antigen, if present, may be the same as or different from the first antigen, if present. In another specific embodiment, the first and second conjugate members further comprising first and second members of a binding pair, respectively. In accordance with that embodiment, the first and second binding pair members of the third conjugate are the same as or different from the first and second binding pair members of the first and second conjugates. Additionally, the first conjugate member may be bound to the second conjugate member via binding between the first and second binding pair members.

As with the first and second conjugates discussed above, the third conjugate may comprise any immune co-stimulatory polypeptide, antigen or infectious agent and binding pair members, including any described herein.

In a related aspect, the invention provides a population of immune cells made by this method. Such immune cells generate or enhance an immune response to the tumor when contacted with other immune cells.

The invention also provides a modified immune cell expressing a receptor for a first immune co-stimulatory polypeptide, wherein the modified immune cell is modified with (a) a first conjugate comprising (i) a conjugate member comprising the first immune co-stimulatory polypeptide and (ii) a conjugate member comprising a first member of a binding pair; and (b) a second conjugate comprising (i) a conjugate member comprising a first antigen or infectious agent and (ii) a conjugate member comprising a second member of the binding pair. In accordance with this embodiment, the first conjugate is conjugated to the immune cell via binding between the immune co-stimulatory polypeptide and the receptor, and the second conjugate is conjugated to the immune cell via binding between the first and second binding pair members.

As with the methods described above, any immune co-stimulatory polypeptide, antigen or infectious agent, and binding pair members can be used in this aspect of the invention, including each described above.

Further, any immune cell expressing a receptor for the first immune co-stimulatory polypeptide can be modified in accordance with this method. In one embodiment, the immune cell is a T cell or neutrophil. Exemplary T cells include CD4+ cells, CD8+ cells, natural killer cells, monocytes and dendritic cells.

Immunostimulatory Moieties

The invention also provides immunostimulatory moieties that have immunostimulatory activity. The immunostimulatory moieties are useful when administered alone, or when used as an adjuvant in conjunction with the administration of an antigen or other immunostimulatory agent. For example, the immunostimulatory moieties are useful in the context of vaccines, cancer immunotherapy, and the treatment of immune-based disorders. The immunostimulatory moieties can be formulated in compositions suitable for administration to an animal, and can be administered to an animal in need of immunostimulation, such as an animal receiving a vaccine, cancer immunotherapy, or undergoing treatment for an immune-based disorder.

In accordance with one embodiment, the immunostimulatory moiety comprises any of the immune co-stimulatory polypeptides described above, such as 4-1BBL, CD86, ICOSL, PD-L1, PD-L2, B7-H3, B7-H4, OX40L, CD27L, CD30L, LIGHT, BAFF, APRIL, CD80 and CD40L. In another embodiment, the immune co-stimulatory polypeptide is selected from the group consisting of 4-1BBL, ICOSL, PD-L1, PD-L2, OX40L, CD27L, CD30L, LIGHT, BAFF and APRIL. In yet another embodiment, the immune co-stimulatory polypeptide is 4-1BBL.

In accordance with one specific aspect of this embodiment, the immunostimulatory moiety further comprises streptavidin or core streptavidin. For example, the immunostimulatory moiety may be a conjugate or fusion protein comprising an immunostimulatory polypeptide and core streptavidin.

In another embodiment, the immunostimulatory moiety consists essentially of the immune co-stimulatory polypeptide and streptavidin or core streptavidin. In accordance with this embodiment, the immunostimulatory moiety does not comprise, and is not conjugated or otherwise bound to any other immunostimulatory agent, such as another immune co-stimulatory polypeptide or antigen.

The invention also includes an immunostimulatory method that comprises administering an immunostimulatory moiety to a patient in need of immune stimulation. In one embodiment of this method, the immunostimulatory moiety comprises an immune co-stimulatory polypeptide and streptavidin or core streptavidin. In another embodiment, the immunostimulatory moiety consists essentially of the immune co-stimulatory polypeptide and streptavidin or core streptavidin. In a further embodiment, the method further comprises administering an antigen to the patient, simultaneously or sequentially (either before or after) administration of the immunostimulatory moiety. In some embodiments of simultaneous administration, the immunostimulatory moiety and antigen are administered in a single composition, such as a mixture comprising the immunostimulatory moiety and antigen. In other embodiments of simultaneous administration, the immunostimulatory moiety and antigen are administered in separate compositions. In some embodiments, the antigen is administered as an antigen-containing conjugate as described above, such as a conjugate comprising an antigen and a member of a binding pair. In other embodiments, the antigen is not administered as a conjugate comprising a member of a binding pair.

Another embodiment of the immunostimulatory method consists essentially of administering an immunostimulatory moiety that consists essentially of the immune co-stimulatory polypeptide and streptavidin or core streptavidin. In accordance with this embodiment, no other immunostimulatory agent, such as another immune co-stimulatory polypeptide or antigen, is administered that would become conjugated or otherwise bound to the immunostimulatory moiety. Thus, for example, no biotinylated molecule, such as biotinylated cells or protein conjugate comprising biotin, is administered.

While not wanting to be bound by any theory, it is believed that the immunostimulatory moieties of the invention stimulate interactions between cell surface immune receptors and their ligands, thereby promoting humoral and cellular immune responses. Immunostimulatory moieties comprising streptavidin (or core streptavidin) form stable tetramers and oligomers that effectively engage receptors, and stimulate B cells, monocytes, and dendritic cells for the production of cytokines, chemokines, and up-regulation of immunostimulatory molecules.

The following examples illustrate the invention in more detail, and are not intended to limit the scope of the invention in any respect.

EXAMPLES

Experimental Methods

Animals. Adult inbred BALB/c (H-$2^d$) and C57BL/6 mice are purchased from Jackson Laboratories (Bar Harbor, Me.). TCR transgenic OT-I, DO11.10, C57BL/6.SJL animals are be purchased from Taconics (Germantown, N.Y.) and maintained under NIH Guidelines.

Establishment of A20 cells expressing OVA. An OVA construct was obtained from Dr. Tom Mitchell of the University of Louisville and directionally cloned into the pcDNA3 vector (Invitrogen, San Diego, Calif.) restricted with BglII and EcoRI. After bacterial transformation and selection on ampicillin medium, several clones were subjected to mini plasmid preparation and digested with BglI/EcoRI to identify positive clones. A clone containing the insert was then used for large plasmid preparation and transfection into A20 cells using Lipofectamine™ 2000 (Invitrogen) kit according to the manufacturer's instructions. Cells are be selected in media containing G418 (Geneticin) and expression of OVA is determined using Western blots and antibodies against OVA or T cell proliferation assays.

Establishment of TC-1 transplantable cervical cancer model. A TC-1 tumor model was established in C57BL/6 mice. The tumorigenic TC-1 cell line was derived by co-transformation of primary C57BL/6 mouse lung epithelial cells with HPV-16 E6 and E7 and an activated ras oncogene, and has been characterized as a model for human cervical carcinoma. TC-1 cells form tumors in syngeneic C57BL/6 mice. To establish the model, $1 \times 10^5$ tumor cells were transplanted into the right flank of C57BL/6 mice and animals were monitored for tumor growth.

Expression and purification of the recombinant 4-1BBL using insect DES expression system. Stable transfectants expressing 4-1BBL using the *Drosophila* DES Expression System (Invitrogen; Carlsbad, Calif.) are established as described in Singh et al., 2003, *Cancer Res.* 63: 4067-73. Transfectants are induced for recombinant protein expression in *Drosophila* serum-free medium (Gibco; Carlsbad, Calif.) supplemented with 1 mM copper sulfate for 72 hours in an incubator shaker set at 25° C. and 105 rpm. Culture supernatant is harvested by centrifugation and subjected to large-scale purification using cobalt (II)-carboxymethylaspartate crosslinked agarose immobilized metal affinity resin (BD-Talon, BD Biosciences) or Ni-NTA metal affinity resin (Qiagen), taking advantage of the 6×-His-tag engineered into the proteins.

Briefly, culture medium containing 4-1BBL are precipitated by dropwise addition of 95% ethanol to produce a final concentration of 10% ethanol. After an overnight incubation at 4° C. the precipitated 4-1BBL is redissolved in 1/10 of its starting volume with binding buffer (50 mM sodium phosphate pH 7.0; 500 mM sodium chloride; 0.5% Tween-20; 1% glycerol; 5 mM 2-mercaptoethanol). The metal affinity resin is equilibrated using 5× gel bed volume of binding buffer, added to the redissolved protein solution containing 4-1BBL, and incubated with end-over-end rotation for 45 minutes at room temperature. The 4-1BBL bound metal affinity resin is washed 2× with 50-100 ml of wash buffer (50 mM sodium phosphate pH 7.0; 500 mM sodium chloride). Bound 4-1BBL is eluted from the metal affinity resin with 2× gel bed volume of elution buffer (50 mM sodium phosphate pH 7.0; 500 mM sodium chloride 150 mM imidazole).

Purified 4-1BBL eluates are pooled and loaded into Amicon Ultra™ (Millipore; Bedford, Mass.) centrifugal filter devices with 30 kD molecular weight cut off membrane. The centrifugal filter devices are centrifuged at 3000 rpm (2000× g) at 4° C. for 15 minutes. Sterile PBS is added to the retentate and the filters are centrifuged again at 3000 rpm (2000×g). The retentate containing the concentrated/desalted 4-1BBL is aspirated from the centrifugal filter devices, placed in sterile cryovials, and stored in liquid nitrogen. The purity of the isolated proteins is assessed by SDS-polyacrylamide gel electrophoresis. Protein concentration is determined using the BCA protein assay (Pierce) according to the manufacturer's instructions.

Expression and purification of biotinylated OVA. The OVA construct described above is subcloned into the pAN and pAC vectors from Avidity, Inc. (Denver, Colo.) to express N-terminal as well as C-terminal AviTag-protein fusions, respectively. After bacterial transformation and selection on ampicillin medium, several clones are subjected to mini plasmid preparation and digested with the appropriate restriction enzymes to identify positive clones. A clone with the insert is used for large plasmid preparation. Plasmids are used to transform AVB100 *E. coli*, a strain with the birA ligase gene stably integrated into the chromosome. Protein expression is induced with L-arabinose for high level of expression of OVA with the biotin tag. The expressed proteins are purified using an AviTag antibody agarose. Purified OVA is assessed for concentration, endotoxin level, and biotinylation using Western blot and alkaline phosphatase conjugated streptavidin for probing. If necessary, endotoxin is removed using Detoxi-Gel Endotoxin Removing kit (Pierce). Biotinylated OVA is conjugated with a CSA-4-1BBL fusion protein and tested in in vivo proliferation assays using OT-I TCR transgenic cells, as discussed below. The protein is aliquoted and frozen in −70° C. until use.

Proliferation assays. For in vivo proliferation assay, spleen and lymph node cells are harvested from OT-I ($OVA_{257\text{-}264}/K^b$) TCR transgenic animals. Cells are labeled with 5 µM CFSE (carboxyfluorescein diacetate succinimidylester) and one million CFSE-labeled cells are transferred into $CD45.1^+$ congeneic B6-SJL mice by tail-vein injection. After 24 hours, animals are challenged with 10 µg OVA alone, OVA mixed with or conjugated to CSA or CSA-4-1BBL. Spleen and lymph nodes cells are harvested after 3 days and proliferation is determined by analysis of CFSE dilution in $CD8^+$ $CD45.1^-$ (OT-1) cell populations in the lymphoid gate. Cells harvested from some animals that did not receive OVA protein are used to determine the parent population for analysis.

In vitro proliferation assays are performed as follows: CFSE-labeled DO11.10 ($OVA_{323\text{-}339}/I\text{-}A^d$) TCR transgenic cells from BALB/c mice are used as responders against irradiated A20 transfectants expressing OVA at various ratios for 3 days. Cultures are harvested and analyzed in flow cytometry for proliferation.

Flow cytometry. Flow cytometric analysis is performed by first titrating the primary and secondary antibodies of interest and then using the optimum concentrations in flow cytometry using standard procedures. See, e.g., Mhoyan et al., 1997, *Transplantation* 64: 1665-70. Isotype-matched antibodies serve as negative controls. Samples are run on a FACS Calibur or Vantage (Becton Dickinson; Mountain View, Calif.) and analysis is performed using FlowJo software (TreeSoft).

Immunotherapy. Vaccinations are performed as follows. Briefly, CSA-4-1BBL fusion protein is mixed with biotinylated OVA in PBS at various molar ratios and then injected intraperitoneally into BALB/c mice for pre-vaccination, or for immunotherapy into animals that have been inoculated subcutaneously in the flank with a lethal dose of viable A20 ($1 \times 10^6$) cells. Controls include animals without vaccination or those vaccinated with control proteins. Once detected, tumors are measured every other day using calipers and tumor size is reported as the average of the longest diameter and the perpendicular diameter±standard error. Animals are euthanized when the tumor size reaches approximately 20 mm in diameter to avoid discomfort.

Statistics. The effect of treatments on tumor survival is estimated using Kaplan-Meier curves. The differences in survival between different groups is assessed using the log-rank test (generalized Savage/Mantel Cox). Procedures involving the comparison of data from groups of individual animals will first have the equality of variance examined using the F test (two groups) or Levene's test (multiple groups). When variances are not equal, log transformations are performed. When normally distributed sample means are to be compared, the Student's t test (two groups) or the Newman-Keuls test (multiple groups) is used. When the data is not normally distributed, the Mann-Whitney U test (two groups) or the Kruskal-Wallis test (multiple groups) is used. Statistical significance is defined as $P<0.05$.

Example 1

CSA-4-1BBL Augments Alloantigen-Driven Responses

As discussed above, 4-1BBL plays an important role in the regulation of adaptive and innate immune responses. 4-1BBL serves as a costimulatory molecule for the activation of $CD4^+$ and $CD8^+$ T cells, NK cells, and DCs and inhibits the suppressive function of $T_{reg}$ cells. Therefore, this molecule can serve as a specific adjuvant for the generation of an effective tumor response for cancer therapy.

The CSA-4-1BBL fusion protein forms tetrameric/oligomeric structure due to the presence of the core streptavidin moiety, and is a soluble molecule. The immunostimulatory activity of CSA-4-1BBL on T cell responses was demonstrated using allogeneic mixed lymphocytes reactions (MLR) as follows.

C57BL/6 mice lymph node cells were used as responders against BALB/c irradiated splenocytes in the presence or absence of CSA-4-1BBL. Cultures were labeled with $[^3H]$ thymidine for the last 18 hours of the culture period and proliferation was assessed. Cultures supplemented with CSA-4-1BBL showed potent proliferative activity as compared with controls (FIG. 8).

Example 2

CSA-4-1BBL Enhances T Cell Proliferation

Figure 9:
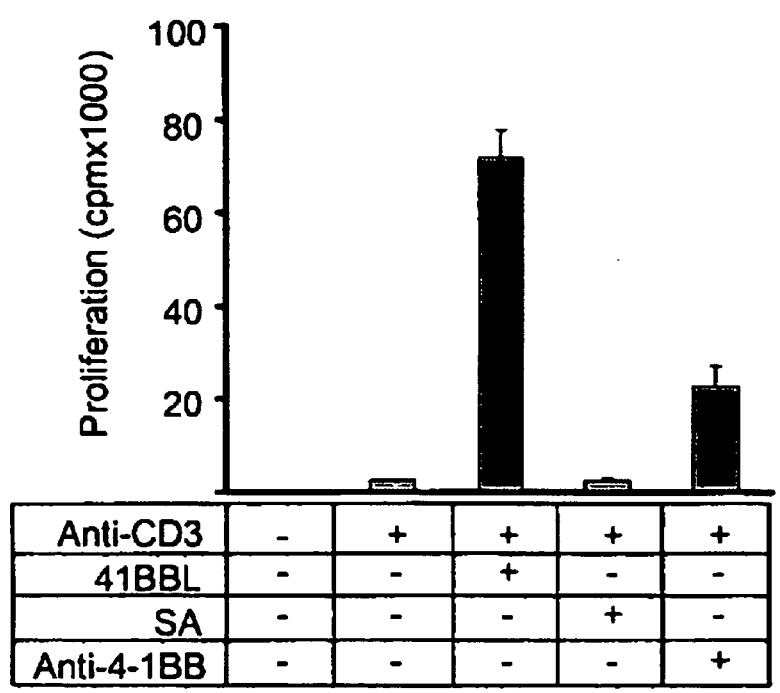
FIG. 9 shows the results of ex vivo T cell proliferation where CD8$^+$ T cells sorted from C57B/6 mice were stimulated with soluble anti-CD3 monoclonal antibody (0.5 µg/ml) and irradiated splenocytes in the presence or absence of CSA-41BBL fusion protein (0.5 µg/ml), control CSA protein (0.19 µg/ml), or anti-4-1BB monoclonal antibody clone 3H3 (5 µg/ml).

To assess the relative activity of the 4-1-BBL fusion protein to a monoclonal antibody against 4-1BB, $CD4^+$ and $CD8^+$ T cells sorted by flow cytometry were polyclonally stimulated with a suboptimum concentration of anti-CD3 antibody in the presence of various amounts of 4-1BBL fusion protein and antibody in proliferation assays. The fusion protein had 70-fold more activity on the proliferation of T cells than the antibody (FIG. 9).

Because this antibody Ab has been shown to have potent activity in animal models of cancer immunotherapy, see, e.g., Melero et al., 1998, Cell Immunol. 190: 167-72; Melero et al., 1997 Nat. Med. 3: 682-85, this data indicates that the CSA-4-1BBL fusion protein will be a useful component of cancer vaccines, both as an adjuvant and as a vehicle to deliver TAAs to DCs.

Example 3

Effect of a Biotinylated OVA/CSA-4-1-BBL Conjugate on $CD8^+$ T Cells

Ovalbumin peptide (OVA) was biotinylated using a commercially available kit (Pierce Biotechnology, Rockford, Ill.). Biotinylated OVA was premixed in vitro with CSA-4-1BBL fusion protein for conjugation at various ratios and injected intraperitoneally into naïve C57BL/6.SJL animals adoptively transferred with one million OT-1 T cells. Specifically, one million OT-I $CD8^+$ T cells were labeled with CFSE and transferred into B6.SJL mice that were immunized with biotinylated ovalbumin (10 µg/injection) ("OVA") and CSA-4-1BBL (1 µg/injection) mixed with biotinylated OVA ("41BBL+OVA") or conjugated OVA-biotin/CSA-4-1BBL ("41BBL-OVA"). (FIG. 10) The last panel of FIG. 10 ("41BBL-OVA*") shows the response for 5 µg of CSA-4-1BBL conjugated to 10 µg biotinylated OVA. For controls, core streptavidin ("SA") was used at equimolar level as CSA-4-1BBL.

Figure 10:
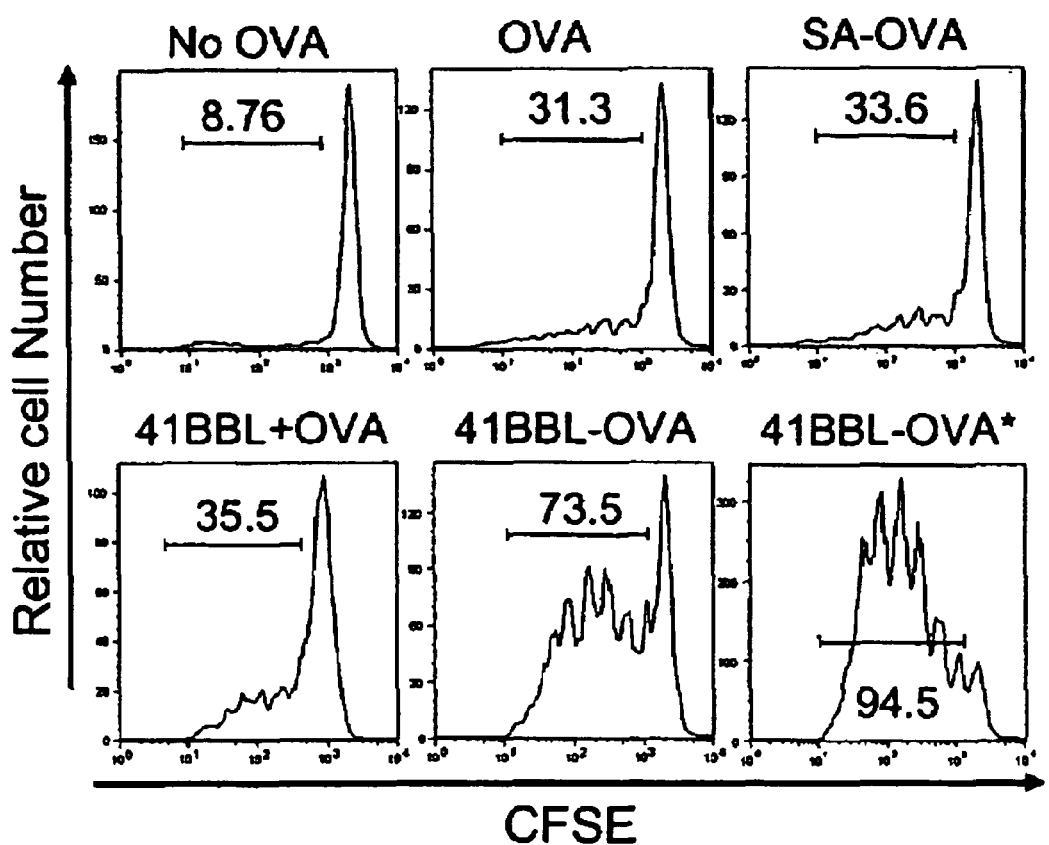
FIG. 10 shows the proliferative response of antigen specific CD8+ T cells when one million OT-I CD8$^+$ T cells were labeled with CFSE and transferred into B6.SJL mice that were immunized with biotinylated OVA (10 µg/injection) and CSA-4-1BBL fusion protein (1 µg/injection) mixed with biotinylated OVA (41BBL+OVA) or a conjugate comprising biotinylated OVA and CSA-4-1BBL. The last panel (*) shows the response for 5 µg of CSA-4-1BBL conjugated to 10 µg biotinylated OVA. Core streptavidin (SA) was used at equimolar level as 4-1BBL.

As shown in FIG. 10, 4-1BBL/OVA conjugates generated a potent (73.5%) proliferative response in OT-1 cells as compared with control "SA/OVA" conjugates (33.6%) or unconjugated, single proteins, "41BBL+OVA" (35.5%). The proliferative response was dose-dependent since a 5 µg dose of CSA-4-1BBL generated a much better response (94.5%) than a 1 µg dose (73.5%).

This example shows that the CSA-4-1BBL fusion protein increased the proliferative response of antigen-specific $CD8^+$ T cells, indicating that the 4-1BBL-CSA/biotinylated antigen construct can successfully deliver antigen to professional APCs and activate these cells for the generation of an effective immune response.

Example 4

CSA-4-1BBL Delivers Antigens to DCs

This example demonstrates that CSA-41BBL effectively delivers antigen to DC. Biotinylated PE was used as a fluorescent antigen. Biotinylated PE (250 ng) was conjugated with 250 ng CSA-41BBL on ice for 30 min. Jaws II Dendritic cells ($5\times10^5$/well) were cultured for 16 hours with biotinylated PE (250 ng/ml) or biotinylated PE/CSA-41BBL conjugate. The level of PE was detected using flow cytometry. FIG. 11A is a histogram showing the PE+ cells. The gray filled area represents untreated cells, the black dashed line represents cells treated with biotinylated PE, and the black line represents cells treated with biotinylated PE/CSA-41BBL conjugate. FIG. 11B shows the mean fluorescence intensity (MFI) of PE for each treatment, and demonstrates that the conjugate-treated cells exhibited a significantly greater response.

Example 5

CSA-4-1BBL Activates DCs

This example demonstrates that 4-1BBL activates dendritic cells. Jaws II Dendritic cells ($5\times10^5$/well) were untreated or treated with 5 µg/ml CSA-41BBL conjugate or 5 µg/ml lipopolysaccharide (LPS) in the presence of 5 ng/ml GM-CSF for 48 hours in 24-well plates. CD86 and MHC class II levels were analyzed using flow cytometry, as show in FIG. 12A. The light gray filled area represents isotype treated cells, the dark gray filled are represents untreated cells, the black line represents CSA-4-1BBL treated cells, and the dashed line represents LPS treated cells. FIG. 12B shows the mean fluorescence intensity (MFI) of CD86 and MHC class II, and demonstrates that the CSA-4-1BBL treated cells exhibited a significantly greater response.

Example 6

CSA-4-1BBL Delivers Antigens to DCs and Activates DCs In Vivo

Figure 13:
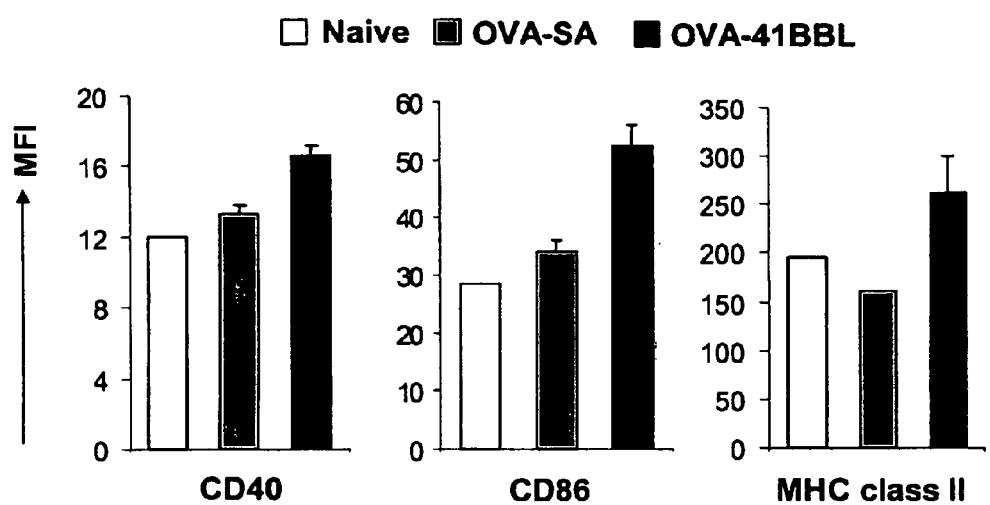
FIG. 13 shows the mean florescence intensity of CD40, CD86 and MHC class II expression on DC cells from naïve, biotinylated OVA/CSA treated, and biotinylated OVA/CSA-4-1BBL treated animals.

This example demonstrates that CSA-4-1BBL delivers biotinylated antigens to dendritic cells and drive these cells to activation in vivo. Biotinylated OVA was contacted with CSA-41BBL to yield a biotinylated OVA/CSA-4-1BBL conjugate. That conjugate or a biotinylated OVA/CSA conjugate was injected intravenously into naïve C57BL/6 mice. 24 hours later, animals were euthanized and spleen cells were harvested. Dendritic cell activation was analyzed using flow cytometry in CD11c+ cell populations. The mean florescence intensity (MFI) of CD40, CD86 and MHC class II expression on dendritic cells from naïve, biotinylated OVA-SA treated, and biotinylated OVA/CSA-41-BBL treated animals were determined, as shown in FIG. 13. This figure demonstrates that the biotinylated OVA/CSA-41-BBL treated animals exhibited a significantly greater response.

Example 7

CSA-4-1BBL Neutralizes the Suppressive Function of Treg Cells

As discussed above, naturally occurring $CD4^+CD25^+$ $FoxP3^+$ Treg cells constitutively express the 4-1BB receptor and, as such, respond to 4-1BBL stimulation. The following example demonstrates the stimulatory activity of the 4-1BBL fusion protein on Treg cells.

$CD4^+$ $CD25^-$Teff cells and $CD4^+CD25^+$ Treg cells were isolated using flow sorting, cultured in a 1:1 ratio in the presence of irradiated syngeneic cells and anti-CD3 antibody. To differentiate between the proliferation of $CD4^+CD25^+$ (DP) versus $CD4^+CD25^-$ (SP) T cells in co-culture experiments, $CD4^+CD25^-$ T cells were stained with carboxyfluorescein diacetate succinimidylester (CFSE, Molecular Probes, OR) and used in suppression assays. Briefly, cells were washed with PBS, incubated in 4 ml of 2.5 μM CFSE/ $1 \times 10^6$ cells (ratio was kept when lower amount of cells were labeled) for 7 min at room temperature. Cells were then incubated in two volumes of fetal bovine serum for 1 min, and washed 2 times with PBS to ensure removal of all excess CFSE. Proliferation was assessed using flow cytometry.

Figure 15:
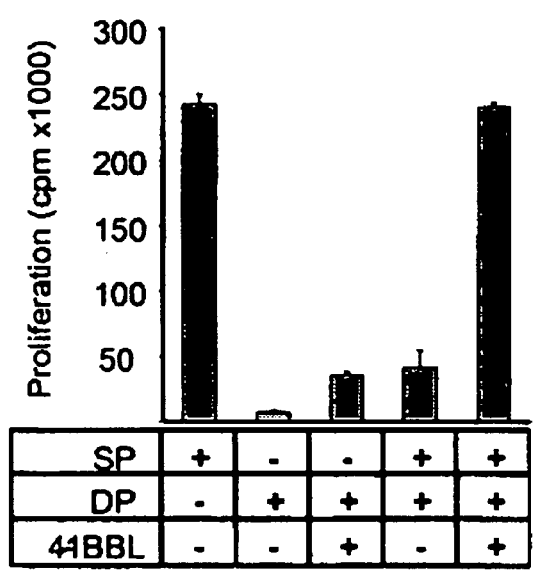
FIG. 15 shows the results of ex vivo T cell proliferation where CD4$^+$ CD25$^-$ (single positive, SP) and CD4$^+$CD25$^+$ (double positive, DP) T cells were sorted from the spleen and peripheral lymph nodes of naïve BALB/c mice, and cultured alone or in a 1:1 ratio in the presence of 0.5 µg/ml anti-CD3 antibody and irradiated splenocytes with or without 1 µg/ml of 4-1 BBL.

Treg cells did not respond to anti-CD3 stimulation as they are anergic, but showed moderate proliferation in response to 4-1BBL (FIG. 15). Notably, Treg cells inhibited the proliferative response of Teff cells, an effect that could be reversed by the addition of 4-1BBL. This is consistent with data using naïve Treg cells, where the suppressive effect of expanded cells was neutralized by the presence of CSA-4-1BBL (see below).

These data confirm the immunomodulatory effects of 4-1BBL, and its utility for cancer immunotherapy. For example, the 4-1BBL fusion protein boosts Teff functions while downregulating the inhibitory function of Treg cells for a more robust anti-tumor immune response.

Example 8

Dual Role of 4-1BBL

The role of 4-1BB/4-1BBL-mediated signaling in the regulation of Treg function has been the subject of two recent studies with opposing findings. While one study demonstrated that 4-1BB signaling neutralizes the suppressive function of Treg cells, Choi et al., 2004, *J. Leukoc. Biol.* 75: 785-91, the other reported that 4-1BB signaling mediates Treg proliferation without a major effect on their suppressive function, Zheng et al., 2004, *J. Immunol.* 173: 2428-34. To clarify this discrepancy, the role of 4-1BB signaling in Treg function was investigated using a CSA-4-1BBL fusion protein.

$CD4^+CD25^-$ (single positive; SP) and $CD4^+CD25^+$ (double positive; DP) T cells were sorted from the spleen and peripheral lymph nodes of naïve BALB/c mice and cultured alone or at 1:1 ratio for 3 days. Cultures were supplemented with irradiated splenocytes, an anti-CD3 antibody (0.5 μg/ml), and the concentrations (μg/ml) of 4-1BBL or equimolar amounts of control CSA protein indicated in FIG. 14A. $CD4^+CD25^+$ double positive (DP) T cells purified from naïve BALB/c mice using flow sorting markedly inhibited the proliferative response of single positive (SP) $CD4^+CD25^-$ Teff cells induced by an antibody against CD3 in co-culture experiments. This suppressive effect was effectively and specifically reversed by supplementing cultures with 1 μg/ml CSA-4-1BBL, but not control CSA used at an equimolar level.

To test whether the observed reversal of suppression by the CSA-4-1BBL fusion protein is due to the restoration of the proliferative response of SP cells, SP cells were labeled with CFSE and used in co-culture experiments in the presence of CSA-4-1BBL (0.5 μg/ml) or CSA as a control protein. The CSA-4-1BBL increased the proliferation of SP cells from 44% for control and 46% for CSA protein to 60%. DP cells significantly reduced the proliferation of SP T cells (16%), which was significantly restored (34%) by 4-1BBL, but not CSA control protein (17%). (FIG. 14B) These data demonstrate that the 4-1BBL fusion protein down-regulates the suppressive function of Treg cells.

Thus, our work shows that the CSA-4-1BBL fusion protein manifested two opposing activities on Treg cells. One the one hand, it synergized with anti-CD3 antibodies and IL-2 to promote Treg cell expansion. On the other hand, it blocked the suppressive function of both naïve and activated Treg cells, but only when the Treg cells were in contact with the 4-1BBL fusion protein, since its removal from the culture medium resulted in recovery of the suppressive function.

This latter effect of 4-1BBL may have some significance in the context of tumors and infections that use Treg cells as immune evasion mechanisms.

Example 9

Use of Antigen-4-1-BBL Conjugate as Cancer Vaccine (a) Production of A20 Transfectants Expressing OVA as a Soluble Protein.

The OVA construct described above are transfected into A20 cells using Lipofectamine™ 2000 kit according to the manufacturer's (Invitrogen) protocol. Stable transfectants are selected in G418 selection medium, cloned at single cell level, and tested for the expression of OVA using Western blots. Clones with significant level of OVA expression are as stimulators for DO11.10 $CD4^+$ T cells specific for OVA peptide in CFSE proliferation assays as described with reference to FIG. 10 above. Once confirmed positive for OVA expression, one million live A20 cells are injected subcutaneously into the right flank of BALB/c mice. Animals are monitored for tumor development and survival every other day, and euthanized when tumors reach a size of 20 mm in diameter. Animals inoculated with the parental A20 cells will serve as control for tumor growth. A20 cell transfectants expressing OVA will form tumors when injected into syngeneic BALB/c mice.

(b) Production of CSA-4-1BBL Fusion Protein Using Insect DES System.

A CSA-4-1BBL protein is made using the DES expression system (Invitrogen) and our established protocols. See, e.g., Singh et al., 2003, Cancer Res. 63: 4067-73; Yolcu et al., 2002, Immunity 17: 795-808. The fusion protein is purified using immobilized metal based affinity chromatography taking advantage of the 6×His tag engineered into the CSA-4-1BBL fusion protein. The protein is desalted, concentrated by ultrafiltration, and analyzed by SDS-PAGE for purity. Protein preparations are assessed for concentration using the bicinchoninic acid (BCA) assay (Pierce) and tested for the presence of endotoxin using QCL-1000® Chromogenic LAL endpoint assay from Cambrex.

(c) Biotinylation of OVA

Maleimide activated, endotoxin-free, chicken OVA (Pierce) is biotinylated using the DSB-X Biotin Labeling Kit according to the manufacturer's (Molecular Probes, San Diego, Calif.) protocol. Following extensive dialysis in PBS, biotinylated OVA is assessed for concentration, endotoxin level, and biotinylation using Western blot and alkaline phosphatase conjugated streptavidin for probing. If necessary, endotoxin will is removed using Detoxi-Gel Endotoxin Removing kit (Pierce). Biotinylated OVA is conjugated with the CSA-4-1BBL fusion protein. The protein conjugate is aliquoted and frozen at −80° C. until use.

(d) Use of Biotinylated OVA/CSA-4-1-BBL Conjugate as Cancer Vaccine

CSA-4-1BBL and biotinylated OVA are premixed in PBS at various molar ratios, such as 1:1, 1:5, 1:10, 5:1, and 10:1 4-1BBL:OVA, and injected intraperitoneally into a group of BALB/c mice at various doses (such as 10, 50, and 100 ug of OVA) at three weekly intervals. Animals injected with streptavidin conjugated to biotinylated OVA, biotinylated OVA alone, or unbiotinylated OVA mixed with CSA-4-1BBL will serve as controls.

Animals are challenged subcutaneously with 1 million live A20 tumor cells in the right flank, monitored for tumor development and survival every other day, and euthanized when tumors reach a size of 20 mm in diameter.

Vaccination with the biotinylated OVA/CSA-4-1-BBL conjugate will generate a potent anti-tumor immune response, leading to the prevention of tumor growth. Vaccination with unconjugated 4-1BBL and OVA may also generate a response, but any such response will be smaller than that generated by the antigen/4-1-BBL conjugate. Vaccination with OVA alone or CSA-OVA may only produce minimal responses, and as such should be ineffective in preventing tumor growth.

Example 10

Early/Late Vaccination with Antigen-4-1-BBL Conjugate

As discussed above, tumors evade the immune system by various mechanisms developed over the course of tumor growth. The efficacy of the conjugates of the present invention early in tumor progression is demonstrated by vaccinating animals concurrently with tumor challenge, when immune evasion mechanisms have not been established. The efficacy of the conjugates of the present invention against established tumors is demonstrated by vaccinating animals once tumors have been established, and have fully developed immune evasion mechanisms.

(a) Efficacy Early in Tumor Progression

BALB/c mice are challenged with one million live A20 cells on the right flank and simultaneously vaccinated intraperitoneally with biotinylated OVA/CSA-4-1BBL conjugate. Vaccination with the antigen/4-1BBL conjugate is repeated once a week for four weeks, by which time the tumor in control animals will reach a size of 10-15 mm in diameter. Unmanipulated animals and animals vaccinated with CSA-OVA conjugates will serve as controls.

(b) Efficacy Against Established Tumors

BALB/c mice are inoculated subcutaneously in the right flank with 1 million live A20 tumor cells. Animals are monitored for tumor development and vaccinated with biotinylated OVA/CSA-4-1BBL conjugate when tumors reach a size of 4-6 mm in diameter. The vaccination protocol will initially involve weekly intraperitoneal. injections until the tumor either disappears or reaches a size of 20 mm in diameter.

Animals that effectively eradicate their tumors will be challenged with 2 million live A20 cells 60 days after tumor disappearance to test the memory response.

While not wanting to be bound by any theory, the antigen/4-1BBL conjugate of the invention may have greater efficacy in preventing the growth of tumor when administered early in tumor progression, as compared with administration once tumors are established, due to the lack of various suppressive mechanisms early in the course of tumor progression. Nevertheless, the antigen/4-1BBL conjugate will show efficacy in eradicating established tumors due to the specific targeting of antigen to DCs for efficient antigen presentation, activation of DCs for the generation of a danger signal (adjuvant effect), and downregulation of Treg cells' suppressive functions. In addition to the indirect effect on DCs, repeated injection with the vaccine may further boost the immune system by engaging 4-1BB receptor on activated T and NK cells, leading to their vigorous proliferation, survival, and memory T cell function.

Example 11

Efficacy of Antigen-4-1-BBL Conjugate by Bystander Effect

The following example will demonstrate that the biotinylated OVA/CSA-4-1BBL conjugate generates an immune responses against undefined A20 tumor antigens (other than OVA), either by bystander effect or epitope spreading.

BALB/c animals are inoculated with A20 expressing OVA in the right flank and parental unmodified A20 cells in the left flank. Once tumors are palpable, animals are vaccinated with the biotinylated OVA/CSA-4-1BBL conjugate. The vaccination schedule outlined above is followed, but may be modified as needed to enhance efficacy. Animals are monitored for the growth of both tumor types.

Alternatively, animals having successfully eradicated their tumor following vaccination with biotinylated OVA/CSA-4-1BBL conjugate (such as in the example above) are challenged subcutaneously with 2 million parental A20 cells on the opposite flank 60 days after the eradication of A20 tumors expressing OVA.

The biotinylated OVA/CSA-4-1BBL conjugate vaccine will show efficacy against parental A20 tumors that lack OVA as a TAA. For example, an effective immune response against OVA will lead to the killing of the tumor, shedding of tumor antigens, and capture and presentation by APCs for the generation of T cell responses against a new set of TAAs. The eradication of parental tumors may further be facilitated by bystander effects generated against A20-OVA tumors.

Example 12

Production Of Biotinylated Antigen Using Bacterial Expression System

In some circumstances, it may be advantageous to produce genetically biotinylated antigens for used as the antigenic component of the vaccine of the present invention. The Biotin AviTag technology of Avidity, Inc. (Denver, Colo.) may be used in this regard. The Biotin AviTag is comprised of a unique 15 amino acid peptide that is recognized by biotin ligase, BirA, that attaches biotin to the lysine residue in the peptide sequence. The Biotin AviTag can be genetically fused to any protein of interest, allowing the protein to be tagged with a biotin molecule.

cDNA encoding OVA is subcloned into the pAN and pAC vector to express N-terminal as well as C-terminal AviTag-protein fusions, respectively. AVB100 *E. coli* B strain with a birA gene stably integrated into the chromosome is transformed and induced with L-arabinose for high level of expression of OVA carrying a biotin tag. The expressed proteins are purified using an AviTag antibody agarose. Purified OVA is assessed for concentration, endotoxin level, and biotinylation using BCA kit, QCL-1000® Chromogenic LAL kit, and Western blots probed with alkaline phosphatase conjugated streptavidin. If necessary, endotoxin is removed using Detoxi-Gel Endotoxin Removing kit (Pierce).

Biotinylated OVA is conjugated with CSA-4-1BBL as described above. The protein conjugate is aliquoted and frozen at −80° C. until use.

Example 13

Use of Antigen/4-1BBL Conjugates Comprising TERT or Survivin

The biotinylated antigen/CSA-4-1BBL conjugate exemplified above with biotinylated OVA/CSA-4-1BBL can be used in any vaccine setting with any antigen. In the context of cancer vaccines, two universal human TAAs, telomerase reverse transcriptase and survivin, may be advantageous antigenic components of a biotinylated antigen/CSA-4-1BBL conjugate of the present invention.

Example 14

E7/4-1BBL Conjugates

As discussed above, a conjugate of the present invention comprising the human papillomavirus E7 antigen as the antigen component is useful against cervical cancer. This example relates to this specific embodiment of the invention.
(a) Production of Biotinylated HPV-16 E7

Biotinylated E7 is used as the antigenic component of a conjugate according to the present invention useful as an HPV vaccine. In one embodiment, full-length E7 protein is to provide a maximum number of epitopes. A cDNA encoding full-length HPV-16 E7 is cloned by RT-PCR using total RNA from TC-1 cells. After sequence verification, the cDNA is subcloned into the pMIB/V5-His vector (Invitrogen) in frame with the 6x-His tag for constitutive expression and secretion in the DES system. Secreted protein is purified using a metal affinity resin as described above. Purified E7 is biotinylated in vitro using EZ-Link Sulfo-NHS-LC-Biotin following the manufacturer's protocol (Pierce). Briefly, purified, concentrated E7 is buffer-exchanged in phosphate buffered saline (PBS) and incubated with EZ-Link Sulfo-NHS-LC-Biotin at room temperature for 1 hour. Unconjugated biotin is removed using tangential flow filtration (Spectrum Labs, NJ).
(b) Production of E7/4-1BBL Conjugates A conjugate comprising E7 and 4-1BBL is produced using biotinylated E7 and a CSA-4-1BBL fusion protein, following the general procedures described above. For comparison, an E7/4-1BBL fusion protein is produced as follows. cDNA encoding E7 and 4-1BBL is subcloned into the pMIB/V5-His vector (Invitrogen) in frame with the 6x-His tag for constitutive expression and secretion in the DES system, and the protein is expressed and purified as described above.
(c) Binding Activity of E7/4-1BBL Conjugate The biotin binding and 4-1BB receptor binding activity of the E7/4-1BBL conjugate is assessed as follows.

For biotin binding, TC-1 cells are biotinylated and incubated with CSA-4-1BBL (100 ng/$10^6$ cells) in PBS on ice. Cells are extensively washed with PBS, stained with a fluorochrome-labeled antibody against 4-1BBL, and analyzed using flow cytometry. Biotinylated cells conjugated with CSA serve as controls.

To test binding of the conjugate or fusion protein to 4-1BB receptor on activated T cells, splenocytes from C57BL/B6 mice are activated with 5 µg/ml of concanavalin A (Con A) for 36 hrs, washed with PBS and incubated with various concentrations of the conjugate or fusion protein on ice. Cells are washed extensively and stained with the appropriate fluorochrome-labeled antibodies to 4-1BBL, core streptavidin, or E7, and analyzed in flow cytometry.

Binding of CSA-4-1BBL conjugate to biotinylated E7 is determined by first forming conjugates using the proteins in a 1:4 ratio (CSA-4-1BBL:E7), following the stoichiometry of CSA-biotin binding, and then testing the conjugates in a sandwich ELISA. Briefly, the conjugated proteins are bound to 96-well plates coated with anti-E7 antibody, washed, and then incubated with a reactive anti-streptavidin antibody to measure the amount of E7/4-1BBL complex present. After confirming formation of conjugates, they are assessed for the ability to bind to 4-1BB receptor on activated T cells as described above.

Example 15

Immune Responses Induced by E7/4-1BBL Conjugate (a) Optimization of Dose.

Optimum doses of a vaccine comprising an E7/4-1-BBL conjugate may be assessed as follows. A conjugate comprising biotinylated E7 and CSA-4-1BBL is formed by mixing biotinylated E7 and CSA-4-1BBL at two ratios (such as CSA-4-1BBL:E7 of 1:4 and 1:8) using 1, 10 or 50 µg biotinylated E7. Comparable amounts of control unbiotinylated E7 also are used. (These doses of E7 are based on studies demonstrating that vaccination with 50 µg of E7 is effective to generate a protective immune response against TC-1 cells.) Optimum ratios of 4-1BBL:E7 and optimum amounts of antigen can be determined and adjusted experimentally, by assessing immune responses to the vaccine under various protocols, such as those described below.
(b) Tetramer Analysis Tetramer staining permits assessment of vaccine efficacy with regard to the expansion of CD8$^+$ T cells. C57BL/6 female mice are injected intraperitoneally with the above-described vaccine preparations in PBS. Mice injected with PBS, CSA-4-1BBL, CSA-4-1BBL+unbiotinylated E7, or E7-4-1BBL fusion protein serve as controls. A second equivalent dose is given intraperitoneally 10 days later, and three days after the last vaccination, splenocytes are harvested and the number of E7-specific CD8+ T cells are quantitated using tetramer technology and flow cytometry. Briefly, splenocytes from immunized animals are labeled with FITC-anti-CD8 antibody and PE-tetramers of MHC class I H-2D$^b$ molecules loaded with the immunodominant epitope of E7, peptide 49-57 (RAHYNIVTF). (The tetramer can be obtained from the National Institutes of Health Tetramer Facility (Atlanta, Ga.)). Class I H-2D$^b$ molecules loaded with Sendai virus nucleoprotein 324-332 peptide (FAPGNYPAL) serves as a negative control. After staining, cells are analyzed by flow cytometry to quantify the percentage of CD8+ T cells positive for the tetramer.

(c) Intracellular IFN-γ Analysis.

The characterization of vaccine-induced CD8+ T cells for the expression of IFN-γ, a signature cytokine for effector CD8$^+$ T cells, permits assessment of the function of the T cells. Female C57BL/6 mice are injected intraperitoneally with an optimum dose of biotinylated E7/CSA-4-1BBL conjugate vaccine (determined as described above), and 10 days later splenocytes from immunized animals are harvested and cocultured with irradiated TC-1 cells expressing E7 for 5 days, and then supplemented with the Golgi transport inhibitor brefeldin A overnight. Live cells are harvested using Ficoll gradients and incubated with anti-mouse Fcγ receptor antibody (2.4G2 from American Type Culture Collection) for 1 hour followed by staining with FITC-labeled anti-CD8 antibody. Cells are then fixed, permeabilized, stained for PE-labeled anti-IFN-γ antibody (Pharmingen) and analyzed by flow cytometry. Cells stained with isotype antibodies serve as controls. Splenocytes from animals immunized with PBS, E7-4-1BBL fusion protein, or CSa-4-1BBL+unbiotinylated E7 serve as controls.

(d) Killing Response

The ability of vaccine-induced CD8$^+$ T cells to lyse TC-1 cells expressing E7 molecule is assessed as follows. Splenocytes harvested from animals vaccinated as described above are cocultured in the presence of 100 μg/ml E7 protein for 5 days. Cultures are supplemented with 50 U/ml exogenous IL-2 to support the growth of CD8+ T cells. Viable splenocytes are recovered using Ficoll gradients and used as effector cells against TC-1 target cells at various effector:target ratios (such as 1:1, 10:1, 20:1, 40:1, and 80:1) in the JAM assay. See, e.g., Singh et al., 2003, *Cancer Res.* 63: 4067-73. Because direct killing of tumor cells by CD8$^+$ T cells is important to cancer immunotherapy, demonstration of efficacy in this assay will further support the efficacy of the vaccine against cervical cancer.

(e) CD4+ T Cell Proliferation Response

The efficacy of biotinylated E7/CSA-4-1BBL in the induction of a CD4+ T cell response is assessed as follows. Splenocytes from immunized animals are labeled with CFSE and cocultured with recombinant E7 protein under the same culture conditions as described above, except that IL-2 is not be added to the cultures. Cells are harvested at various days during culturing, stained with an APC-CD4 antibody, and analyzed for proliferation using flow cytometry. Cultures without E7 protein or with OVA protein serve as controls. Because there is a general consensus that a CD4+ T cell response is important for CD8+ T cell and B cell responses, demonstration of efficacy in this assay will further support the efficacy of the vaccine against cervical cancer.

(f) Humoral Response

The ability of in vivo treatment with a biotinylated E7/CSA-4-1BBL vaccine to generate a humoral response is assessed as follows. Blood from vaccinated mice is collected, and serum is isolated and used to screen Maxisorb ELISA plates (Nalgene Nunc International) coated with E7 protein. Anti-E7 IgG and IgM is detected with horseradish peroxidase-conjugated goat anti-mouse IgG and goat anti-mouse IgM antibodies. Controls include sera harvested from animals immunized with PBS and control proteins such as those described above.

The biotinylated E7/CSA-4-1BBL conjugate vaccine will generate potent responses in these assays. Vaccination with E7-4-1BBL fusion protein may also generate a response, but any such response is expected to be of smaller magnitude. Vaccination with CSA-4-1BBL plus unbiotinylated E7 may produce a response, but any such response will not be as strong as that of the conjugate vaccine because the uptake of E7 antigen by APCs will be a random event, and not as efficient as the targeted delivery of E7 to APCs achieved by the conjugate.

Example 16

Therapeutic Efficacy of E7/4-1BBL Conjugate

The efficacy of a vaccine comprising an E7/4-1BBL conjugate of the present invention in preventing and eradicating tumor formation in TC-1 transplantable tumor models is assessed in two different settings. The first setting involves vaccination prior to tumor injections, when the immune evasion mechanisms have not yet developed. The second setting involves vaccination against established tumors with fully developed immune evasion mechanisms. C57BL/6 mice are injected with TC-1 cells to induce tumor formation, and vaccinated pre- and post-TC-1 injection with biotinylated E7/CSA-4-1BBL conjugate. Immune responses are assessed as described above. Mice also are monitored for tumor development and survival every other day, and euthanized when tumors reach a size of 20 mm in diameter.

(a) Efficacy of E7/4-1BBL Conjugate Against Subsequent Tumor Challenge.

The following example will demonstate that immunization with an E7/4-1BBL conjugate of the present invention generates protective immunity against a subsequent tumor challenge.

Female C57BL/6 mice are injected intraperitoneally with PBS alone, CSA-4-1BBL alone, CSA-4-1BBL mixed with unbiotinylated E7, a biotinylated E7/CSA-4-1BBL conjugate of the invention, and a E-7-4-1BBL fusion protein. Doses optimized as described above are used. A second equivalent dose is given subcutaneously 14 days after the first dose. TC-1 cells are harvested, resuspended in sterile PBS, and used for injection fourteen days after the last immunization. Mice are challenged subcutaneously in the right flank with $1 \times 10^5$ TC-1 cells (day 0) and observed for 60 days. As a control to verify the specificity of the conjugate for E7$^+$ tumors, one set of immunized mice are challenged with A20 cancer cells. Mice are monitored for tumor development and survival every other day, and euthanized when tumors reach a size of 20 mm in diameter. Animals that do not develop tumors are re-challenged with $1 \times 10^6$ TC-1 cells 60 days after the first tumor challenge to test the memory response. At fourteen day intervals, mice from each group are sacrificed and their splenocytes are harvested. Splenocytes are used to determine CD8+ T cell responses using tetramer staining and cytokine staining as described above.

(b) Efficacy of E7/4-1BBL Conjugate Against Existing Tumors

The therapeutic effects of an E7/4-1BBL conjugate of the present invention against pre-existing tumors is demonstrated as follows.

Female C57BL/6 mice are injected subcutaneously on the right flank with TC-1 cells and vaccinated when 100% of the mice have palpable tumors. Vaccines are administered doses optimized as described above intraperitoneally every week until the tumor size reaches 20 mm in diameter, at which time the mice are euthanized. The growth rate of the tumors and morbidity is assessed for 60 days. In addition, long-term survival is assessed and followed over 90 days.

Vaccination with a biotinylated E7/CSA-4-1BBL conjugate of the invention will generate a potent anti-tumor immune response in both settings, leading to the prevention of tumor growth and the eradication of existing tumors. Vaccination with unconjugated CSA-4-1BBL and E7 and with the E7-4-1BBL fusion protein may also generate an anti-tumor response, but any such response will be minimal and likely ineffective in preventing tumor growth or eradicating existing tumors.

Example 17

Conjugates Comprising Influenza A Antigens cDNAs of influenza proteins of interest (e.g., H1, N1, NP and/or MP2) are generated by the reverse transcriptase-polymerase chain reaction from influenza A RNA. The cDNAs are subcloned into the pCSA vector, and transfected into *Drosophila* insect cells for the establishment of stable transfectants.

Taking advantage of a 6×-His tag engineered into the proteins, the secreted H1, N1, NP and MP2 proteins are purified from the *Drosophila* culture media using a metal affinity resin and tangential flow filtration (methods and techniques already employed by ApoImmune). Purified proteins are analyzed by gel electrophoresis, immunoblot techniques, matrix assisted laser desorption/ionization-mass spectrometry (MALDI-MS), and analytical ultracentrifugation.

CSA-4-1BBL (made as described above) is mixed at a molar ratio of 1:4 with biotinylated H1, N1, NP or MP2 to form an Influenza A antigen/4-1 BBL conjugate. Briefly, biotinylated H1, N1, NP or MP2 is incubated with CSA-4-1BBL for one hour at 4 C. Unbiotinylated H1, N1, NP or MP2 are incubated with CSA-4-1BBL to serve as unconjugated controls. The conjugates can be formulated into compositions useful as vaccines.

Example 18

Vaccination Against Influenza A (a) Dosing Optimization

C57BL/6 mice are vaccinated with varying doses of the Influenza A antigen/4-1BBL conjugates described above. Immune responses in the mice are determined using standard immunological techniques including tetramer technology, cytokine staining, cytotoxity assays, and the measurement of humoral responses, as described above. Initial results are used to determine an optimal dosing regimen for the vaccines.

(b) Vaccination with Infection Challenge

The protective and therapeutic efficacy of the Influenza A antigen/4-1BBL conjugate vaccines is demonstrated in mice challenged with influenza A as follows. Human influenza virus-infected animals are treated with Influenza A antigen/4-1BBL conjugate vaccines pre- and post-infection and viral titers are measured to determine the efficacy of treatment. Lungs from vaccinated and control infected animals are harvested days 1, 3, 5, 7, and 9 post-infection. Weight loss is determined daily as an indirect measurement of morbidity.

In another series of experiments, lung pathology is evaluated and pulmonary viral titers are determined. For this purpose, lungs are homogenized and viral supernatants are collected following centrifugation of the homogenate at 1500×g for 15 min and frozen at −80° C. until subsequent analysis. Dilutions of viral supernatants from lungs are added to $3 \times 10^4$ MDCK cells/well in a 96-well U-bottom plate for 24 hours at 37° C., media is removed from wells and serum-free media is added. Four days later, virus titers are determined by using standard curve of known virus concentration and the Reed-Munch calculation of TCID after identifying the dilution at which the culture supernatants no longer agglutinate chicken red blood cells.

Example 19

Immune Co-Stimulatory CD40L Moiety

The human monocytic leukemia THP-1 and mouse A20 B-cell lymphoma lines used in this example were purchased from the American Type Culture Collection (ATCC, Rockville, Md., USA). A20 cells were cultured in DMEM (GIBCO, Gaithersburg, Md., USA) supplemented with 10% heat-inactivated fetal bovine serum (FBS; Valley Biomedical, Winchester, Va., USA), 12 mM L-glutamine, 100 U/ml penicillin, 100 μg/ml streptomycin (all from GIBCO) and 50 μM 2-mercaptoethanol (Sigma, St. Louis, Mo., USA). THP-1 cells were cultured in RPMI supplemented with 5% FBS, 100 U/ml penicillin and 0.1 mM Hepes buffer (GIBCO) at 37° C. in a humidified 5% $CO_2$ incubator. Cells were grown in suspension at 37° C. in 5% $CO_2$.

The Chinese Hamster ovary (CHO) and stable mouse CD154 transfected CHO(CHO-mCD40L) lines used in this example were provided by Dr. Gail Bishop (University of Iowa) and were maintained in RPMI 1640 (GIBCO) containing 100 mM Hepes, 50 μg/ml gentamicin and 5% FBS.

Primary monocytes isolated by counterflow elutriation from human peripheral blood mononuclear cells were a gift from Dr. Larry Wahl (NICDR).

Immortalized macrophage cell lines from CD40 knock out mice (CD40KO cell line) were established by infecting bone marrow cells with the murine recombinant J2 retrovirus containing the v-myc and v-raf oncogenes as previously described. See, e.g., Clemon-Miller et al., 2000, Immunobiol. 202: 477-92.

For the generation of stable human CD40 expressing transfectants, the J2 transformed lines were electroporated with 10 μg of DNA at 600 v, 20μsecs, and 2 pulses. Zeocin (100 μg/ml) was added to the medium 24 hr after transfection and resistant colonies were stained for surface expression of CD40. High CD40 expressing cells were sorted using the FACS Vantage SE (Becton Dickinson, San Jose Calif., USA) and maintained for use in these studies.

(a) Cloning and Expression of CSA-CD40L Moieties

Figure 16:
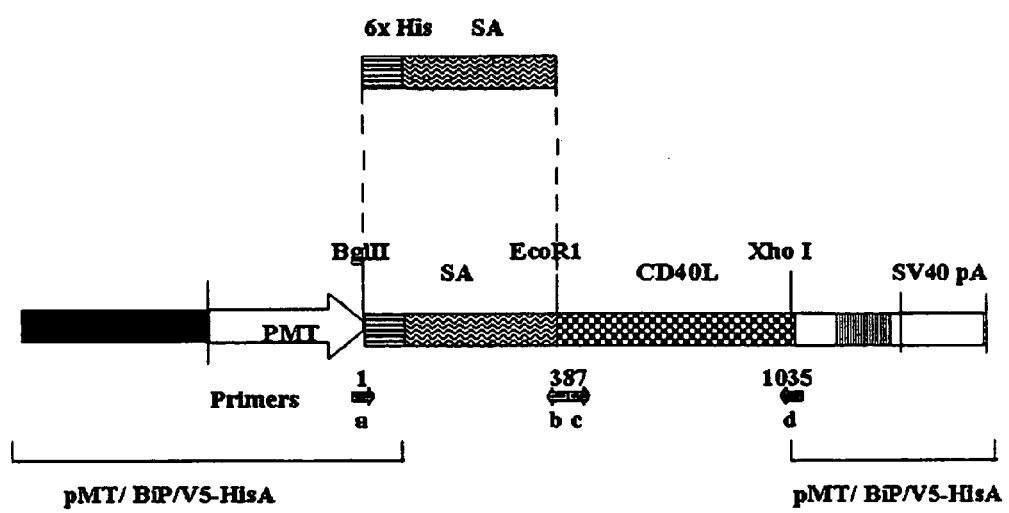
FIG. 16 shows the construction of CSA-hCD40L and CSA-mCD40L constructs. Arrows indicate primers (a, b, c, d) and their orientations used for cloning purposes.

The gene encoding CSA was cloned using genomic DNA isolated from *Streptomyces avidinii* as a template and specific primers in PCR (a and b in FIG. 16). The extracellular domain of human CD40L was cloned using the first strand cDNA generated from total RNA isolated from phytohaemagglutinin (PHA) activated human peripheral blood lymphocytes as a template and CD40L-specific primers (c and d in FIG. 16) in PCR. The murine CD40L was cloned in the same manner as CSA-hCD40L using total RNA isolated from mouse splenocytes activated with concanavalin A (ConA).

The CSA/CD40L gene was then subcloned in frame into the pMT/BiP/V5-His CuSO$_4$-inducible vector for expression into the *Drosophila* S2 expression system (DES; Invitrogen, San Diego, Calif., USA). *Drosophila* S2 cells were transfected with 20 µg of the recombinant vector using the Calcium Phosphate Transfection kit according to the manufacturer's protocol (Invitrogen). Stable transfectants were established by cotransfection with 1 µg of pCoHygro vector and maintenance in the presence of 300 µg/ml hygromycin. The expression of recombinant proteins was achieved using copper sulfate at a final concentration of 500 µM. Culture supernatants were collected 3 days after the induction, precipitated with 40% ammonium persulfate, and dialyzed against PBS.

Recombinant proteins were purified using a modified metal-ion affinity chromatography method as previously described. See, e.g., Lehr et al., 2000, Protein Expression Purif., 19: 362-68. Briefly, culture supernatants or precipitated proteins were passed through a Pharmacia XK 16 column packed with chelating sepharose fast flow (Pharmacia Biotech, Upsala, Sweden) and the recombinant proteins were eluted with 50 mM imidazole. Protein concentration was determined using Bradford dye-binding method or ELISA (R&D Systems, Minneapolis, Minn., USA).

(b) Characterization of CSA-CD40L Moieties by Western Blot and ELISA

The expression of CSA-hCD40L was detected and quantified using the Quantikine CD40L immunoassay, which uses polyclonal Abs specific for CD40L pre-coated onto a microplate as described by manufacturer's instructions (R&D Systems). For Western blot analysis, supernatants of CSA-hCD40L and CSA-mCD40L were first fractionated by sodium dodecyl sulfate-polyacrylamide gel electrophoresis under native and denaturing conditions and then transferred onto polyvinylidene difluoride membranes using a semidry-blot apparatus (BioRad, Hercules, Calif., USA). Membranes were first incubated in blocking buffer and then in goat anti-SA Ab (Pierce, Rockford, Ill., USA) at 1:1000 dilution in the blocking buffer for 1 hour at room temperature. Membranes were then washed extensively and incubated with horseradish peroxidase-conjugated antigoat antibody at 1:4000 dilutions for 1 hour. Finally, the proteins were detected using a chemiluminescent substrate according to the manufacturer's instructions (ECL, Amersham Biosciences, UK).

Transfectants expressed high levels of CSA-CD40L moieties that formed stable tetramers and higher order structures under nondenaturing PAGE conditions. Dissociation into monomers occurred only under denaturing conditions following heating at 100° C., but not 60° C. These data demonstrate that CD40L polypeptides of the immune co-stimulatory moieties do not interfere with the expression, proper folding, and existence of CSA as oligomers.

(c) Receptor Binding and Activation Assays

One million CD40 positive mouse A20 B cell lymphoma or human macrophage THP-1 cells were incubated with 200 ng/ml of CSA-CD40L (human or mouse) moieties or control CSA protein at 4° C. for 30 min. After several washes with PBS, the bound proteins were detected using FITC conjugated anti-streptavidin antibody (Vector Laboratories, Burlingame, Calif., USA) in flow cytometry. CSA was used as a negative control to detect nonspecific binding. The effect of stimulation with CSA-CD40L on the expression of CD80 and MHC class II molecules was determined by culturing $0.5 \times 10^6$ THP-1 cells with 100 ng/ml of CSA-hCD40L or CSA or coculturing with $0.5 \times 10^6$ CHO cells transfected with the membrane form of CD40L for 48 hours. Cells were then washed and stained with saturating concentrations of FITC conjugated anti-CD80 (L307.4) and HLA class II (TU36) antibodies (BD-PharMingen, San Diego, Calif., USA) and analyzed by flow cytometry.

Figure 17:
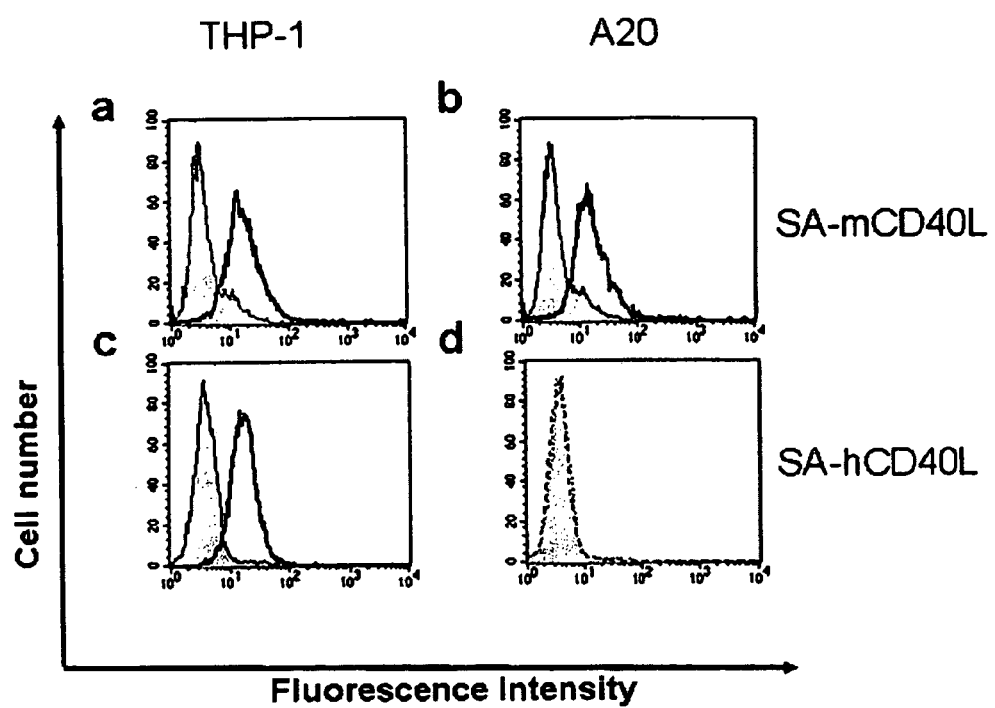
FIG. 17 shows the flow cytometry analysis demonstrating binding of CSA-mCD40L and CSA-hCD40L to CD40 receptors, where human THP-1 and mouse A20 cell lines were incubated with CSA-mCD40L or CSA-hCD40L, stained with FITC labeled anti-streptavidin antibody, and analyzed in flow cytometry. Panels (a) and (b) show binding of CSA-mCD40L to human and mouse cell lines, respectively, and panels (c) and (d) show binding of CSA-hCD40L to human and mouse cell lines, respectively.

CSA-mCD40L bound to both human and murine CD40 receptors (FIGS. 17A & B, dark line), as determined by flow cytometry and shown in FIG. 17. In contrast, CSA-hCD40L interacted only with its receptor on human cells, with minimal to undetectable binding to murine cells (FIGS. 17C & D, dark line), demonstrating its species specificity. These interactions were CD40-specific since there was no detectable binding when CSA used as a control protein (FIG. 17, grey filled areas).

Figure 18:
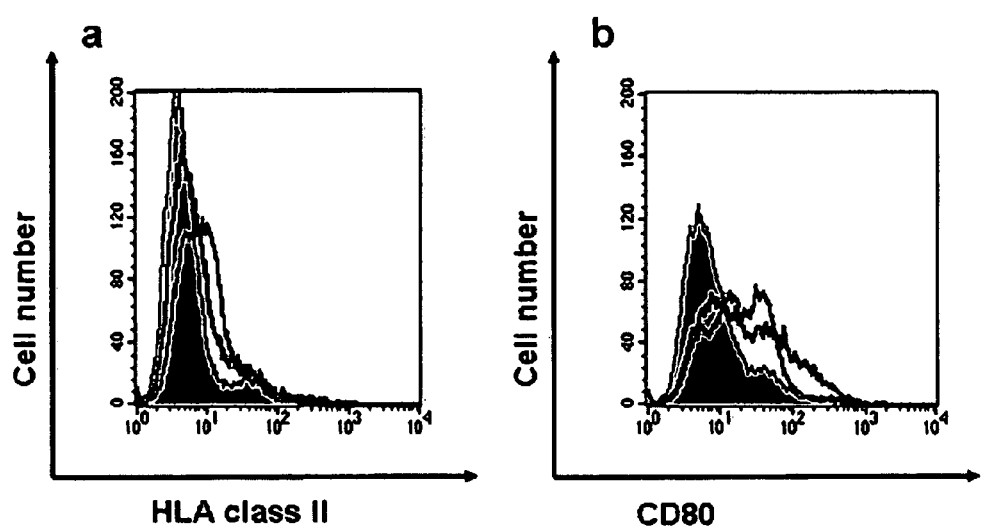
FIG. 18 shows the flow cytometry analysis demonstrating upregulation of HLA class II and costimulatory molecules on macrophages stimulated with CSA-hCD40L, where a human THP-1 cell line was stimulated with 100 ng/ml of CSA-hCD40L for 48 hours (thin solid lines) and analyzed using antibodies to HLA class II (FIG. 18A) and CD80 (FIG. 18B) molecules in flow cytometry. Cells incubated with CSA protein (solid histograms) and CHO cell transfectants expressing membrane-bound mouse CD40L (thick solid line) served as negative and positive controls, respectively.

The upregulated expression of both MHC class II and CD80 molecules was detected on the surface of THP-1 cells using antibodies to HLA class II (FIG. 18A) and CD80 (FIG. 18B) molecules in flow cytometry at all CSA-hCD40L protein concentrations tested, with maximum upregulation achieved at 100 ng protein/$5 \times 10^5$ cells after 48 hours of stimulation. CSA-hCD40L (thin solid lines) was more effective than the membrane bound form of CD40L expressed on CHO cells (thick solid line) in upregulating HLA class II molecules (MFI of 55.8 versus 35.5). In contrast, the upregulation of CD80 by both forms of CD40L was almost comparable (MFI of 33.6 versus 36.2). The upregulated expression was specific to CSA-hCD40L since incubation with CSA protein (solid histograms) did not significantly affect the expression of CD80 and HLA class II molecules over background levels.

(d) Preparation of Bone Marrow-Derived DCs

Bone marrow was flushed from the femurs of 6- to 8-week old mice, dispersed into single cells by pipetting, and red blood cells were lysed with ammonium chloride potassium (ACK) solution. The single cell suspensions were then depleted for T and B cells using a cocktail of TIB 105, TIB 146 and clone RL-172 hybridoma cell culture saturated supernatants for 30 minutes on ice. (Culture supernatants were a gift of Dr. Tatiana Zorina, University of Pittsburgh, Pa.). Cells were incubated with rabbit complement for 30 minutes at 37° C. and cultured overnight (37° C., 5% CO$_2$) in complete medium (RPMI 1640, 2 mM L-glutamine, 100 µg/ml penicillin and streptomycin, 10% FBS, 0.1 mM non-essential amino acids, 1 mM sodium pyruvate, 1 µg/ml indomethacin and 50 µM N-methyl-L-arginine) (Sigma) in six-well plates at a concentration of $10^6$ cells/ml. Non-adherent cells were collected by gentle pipetting, counted, and resuspended at a concentration of $10^5$ cells/ml in complete medium supplemented with recombinant murine granulocyte-macrophage colony-stimulating factor (5 ng/ml) and rmIL-4 (5 ng/ml) (All from US Biological, Swampscott, Mass., USA). Cells were cultured in six-well plates (4 ml/well) for 5 days.

On the fifth day, DCs present in the culture were typed for the expression of cell surface MHC and costimulatory molecules and incubated with varying concentrations (01-0.5 µg/$10^6$ cells) of CA-mCD40L, medium alone, or CSA. Cells were harvested on various days and analyzed for the expression of maturation markers using PE-labeled monoclonal antibody (HL3) against CD11c and FITC labeled mAbs to CD80 (16-10A1) and CD86 (GL1) (all from PharMingen).

Figure 19:
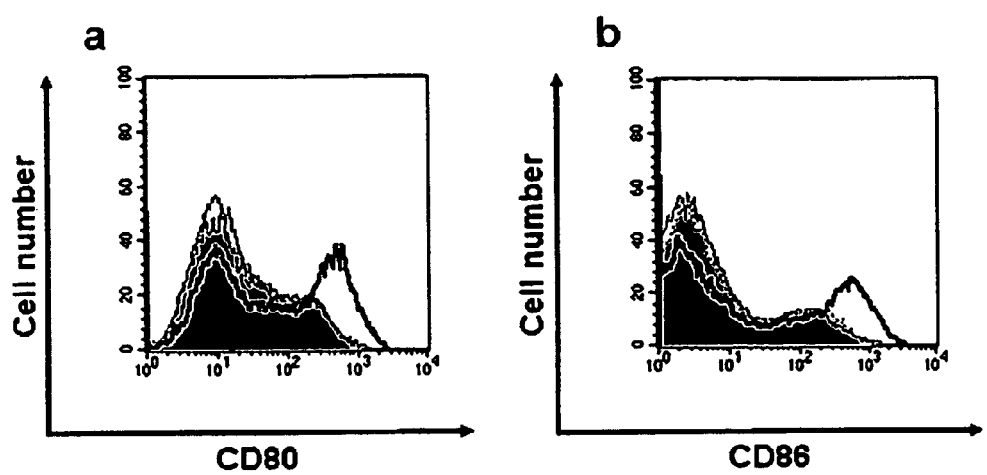
FIG. 19 shows the flow cytometry analysis demonstrating the phenotypic maturation of murine DCs stimulated with CSA-mCD40L, where bone marrow-derived immature DCs were stimulated with varying concentrations of CSA-mCD40L (open histograms) for various time periods, and analyzed using specific antibodies for the expression of CD80 (FIG. 19A) and CD86 (FIG. 19B). Cells left unstimulated (thin solid lines) or stimulated with CSA protein (solid histograms) served as controls. Data are shown for 200 ng protein per $10^6$ cells stimulated for 48 hours.

The immature dendritic cells from day 5 murine bone marrow cultures that were incubated with various concentrations of mouse CSA-CD40L (01-0.5 µg/$10^6$ cells) for 48 hours showed increased expression of both CD80 and CD86 costimulatory molecules (FIGS. 19A & B), with the effect on the upregulation of CD80 expression greater than that for CD86 (3 versus 2 fold) at 0.2 μg protein concentration per $10^6$ cells. Higher concentrations of CSA-CD40L fusion proteins or longer incubation periods did not result in further upregulation (data not shown). This effect was specific to the immune co-stimulatory moiety because cells incubated with CSA protein had minimal to undetectable changes in the expression of costimulatory molecules over background levels.

(e) Analysis of Pro-Inflammatory Cytokine Production

Human monocytes were plated in 96-well microtiter plates and stimulated using 1 μg/ml of a commercially available trimeric recombinant human CD40L (rhsCD40L)+1 μg/ml enhancer (Alexis Biochemicals, San Diego, Calif., USA) and 100 ng/ml of CSA-hCD40L, CSA-mCD40L, or CSA. Supernatants were harvested after 18 hours of incubation and assayed by ELISA using the OptEIA™ sets for all cytokines (PharMingen). Analysis was performed using E-max Precision microplate reader (Molecular Devices, Sunnyvale, Calif., USA).

Figure 20:
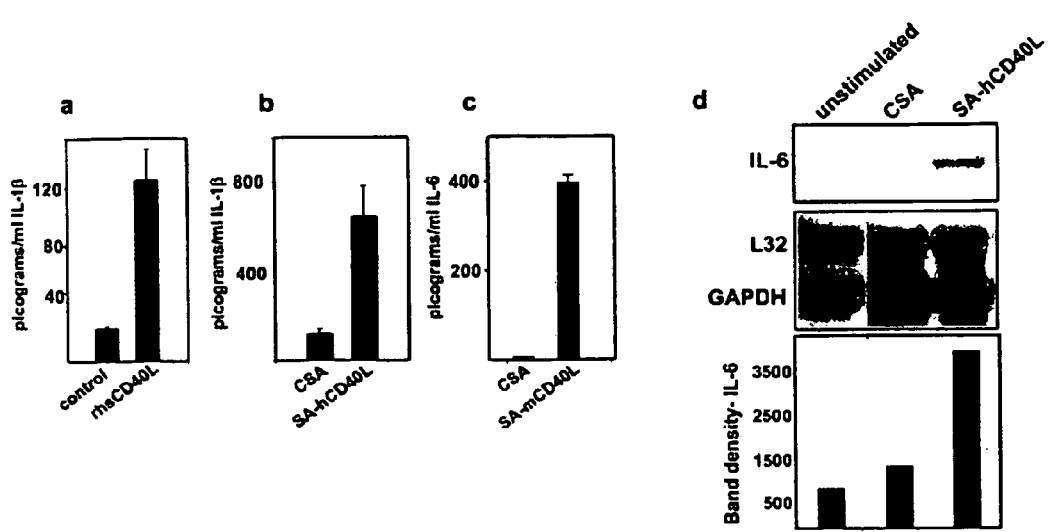
FIG. 20 shows the secretion of cytokines by human monocytes stimulated with CSA-CD40L, where primary elutriated human monocytes were stimulated with 1 µg/ml of each rhsCD40L+ enhancer (FIG. 20A) and 100 ng/ml of CSA-hCD40L (FIG. 20B) or 250 ng/ml of CSA-mCD40L (FIG. 20C) or CSA for 18 hours, and supernatants were analyzed for IL-1β and IL-6 content by ELISA.

Ligation of human monocytes with CSA-hCD40L resulted in a 5-fold stimulation of human IL-1β production above CSA alone, which is equivalent to the levels induced by rhsCD40L (FIGS. 20A & B). Similarly, stimulation of human monocytes with CSA-mCD40L resulted in a robust stimulation of human IL-6 (FIGS. 20C & D). Thus, human and murine CSA-CD40L fusion proteins are both capable of stimulating CD40 on human monocytes to produce IL-β and IL-6.

(f) RNAse Protection Assay

Analysis of cytokine mRNA synthesis was performed by RNAse protection assay. Cells were plated in a 6-well plate and stimulated via CD40 using CSA-CD40L moieties for 3 to 4 hours. CHO transfectants expressing CD40L and rhsCD40L with enhancer were used as controls. RNA was extracted using Trizol as described by manufacturer's instructions (Invitrogen). RNA (5 μg) was hybridized with a radiolabeled probe generated from the human cytokine/RNA template set, mCK-3b (RiboQuant, BD-PharMingen, San Diego, Calif., USA), at 55° C. overnight. RNAse treatment was carried out at 37° C. for 45 minutes, following which the protected probe was purified and resolved by electrophoresis using a 5% polyacrylamide gel (BioRad) in TBE buffer. The gel was dried and exposed to Kodak Biomax XL X-ray film (Eastman Kodak, Rochester, N.Y., USA). With the undigested probe as markers, a standard curve was plotted as migration distances versus nucleotide length on semi log paper. The identity of the RNAse-protected bands in the samples was then extrapolated from the graph.

A shown in FIG. 20D, stimulation with CSA-hCD40L resulted in a 2.8-fold increase in IL-6 mRNA over CSA alone.

Taken together, these data indicate that both human and murine CSA-CD40Ls are capable of inducing CD40 signaling in monocytes and macrophages.

(g) CSA-hCD40L Stimulates iNOS Production in IFN-γ Primed Macrophages

CD40 ligation of IFN-γ primed macrophages results in the stimulation of nitric oxide production, which plays a critical role in the microbicidal and cytotoxic activities of macrophages. Inducible nitric oxide synthase (iNOS) belongs to a family of nitric oxide synthases that catalyze the synthesis of nitric oxide from L-arginine. Th1 and Th2 T helper cells can differentially regulate arginine metabolism in macrophages. Th1 cells induce iNOS production by macrophages while Th2 cells induce macrophages to produce arginase which is associated with anti-inflammatory function. Thus, macrophage iNOS production is a hallmark of a Th1 type of immune response.

Figure 21:
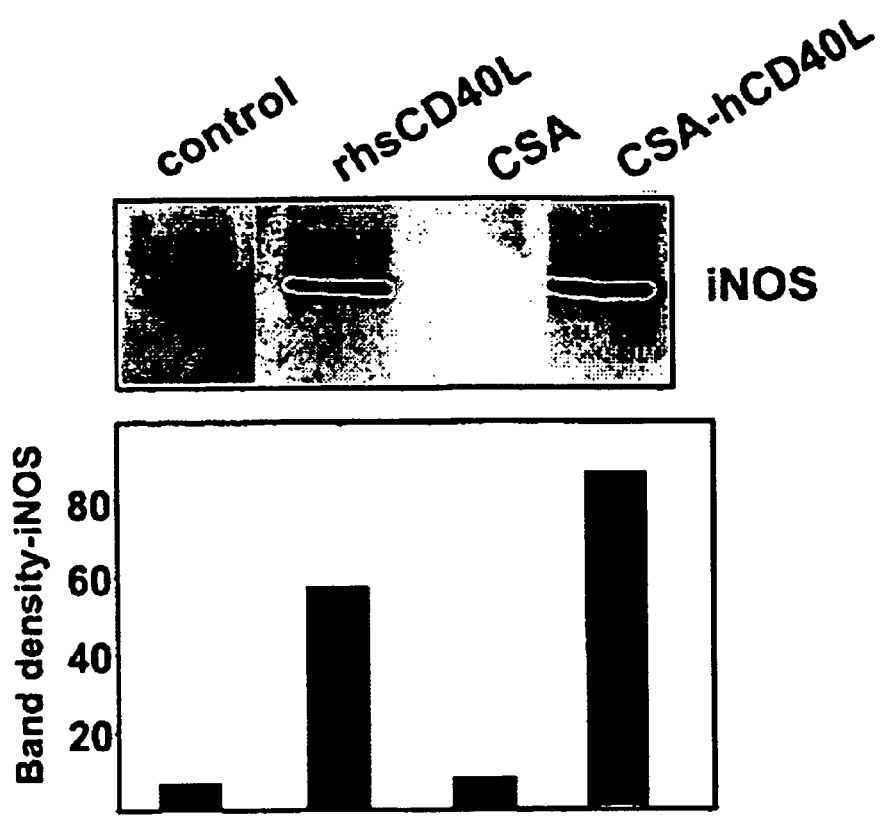
FIG. 21 shows the stimulation of iNOS expression in macrophages stimulated with CSA-hCD40L, where the murine CD40KO macrophage line transfected to express human CD40 was primed with IFN-γ for 24 hours and cells were then stimulated with 1 µg/ml of commercial rhsCD40L with the enhancer or 300 ng/ml of CSA-hCD40L or CSA proteins for 24 hours, and cell lysates were analyzed by Western blot using anti-iNOS antibody. The histogram represents the density of the iNOS bands.

The ability of CSA-CD40L moieties to stimulate iNOS production in murine macrophages was demonstrated as follows. CD40KO-human CD40 cells were primed for 24 hours with IFN-γ and subsequently stimulated with CSA-hCD40L, rhsCD40L, or CSA alone for 24 h. Cell lysates were normalized and analyzed by Western blot using anti-iNOS Ab. As demonstrated in FIG. 21, stimulation of macrophages with CSA-hCD40L or rhsCD40L, but not CSA, resulted in the stimulation of iNOS production. Stimulation with 1 μg/ml of commercial rhsCD40L resulted in a 6-fold stimulation of iNOS above background, while stimulation with 300 ng/ml of CSA-hCD40L resulted in a 9-fold stimulation of iNOS above CSA alone. These data indicate that CSA-hCD40L is a potent stimulator of macrophage iNOS production.

Example 20

In Vivo Killing Response Induced by CSA-4-1BBL

Naïve C57BL/6 mice were immunized intravenously with 50 μg ovalbumin (OVA) as the antigen, and two doses (12.5 μg and 25 μg, respectively) of CSA-4-1BBL or LPS as an adjuvant. Naïve animals were used as a control.

Figure 22:
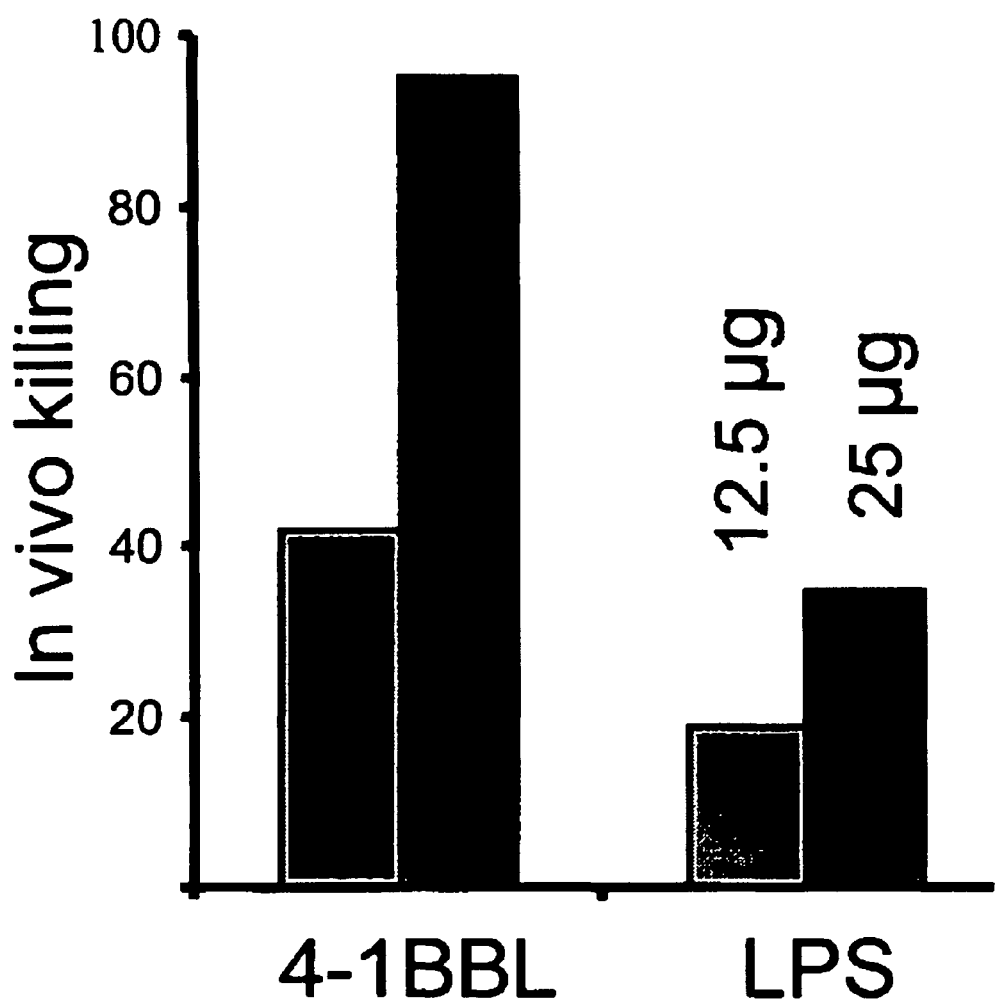
FIG. 22 shows the strong in vivo adjuvant effect of CSA-4-1BBL as compared to LPS at doses of 12.5 and 25 µg, with 50 µg OVA as the antigen. Results are reported in terms of in vivo killing percentage.

Seven days later, all mice received CFSE labeled target cells, which were prepared as follows. Splenocytes from naïve C57BL/6 mice were divided into two populations. The first population was labeled with 0.25 μM CFSE ($CFSE^{low}$) and the second population was labeled with 2.5 μM CFSE and then pulsed with 2 μg/ml $OVA_{257-264}$ peptide (SIINFEKL) for 1 hour ($CFSE^{hi}$). Cells were mixed at a ratio of 1:1 ad a total of $1 \times 10^7$ cells were injected intravenously into recipient animals. Spleens were harvested 48 hours later, and CSFE fluorescence intensity was analyzed by flow cytometry. Results are shown in FIG. 22, expressed as the percentage lysis of the peptide-pulsed $CFSE^{hi}$ peak as compared to the reference $CFSE^{low}$ peak, normalized to naïve animals. As shown in FIG. 22, immunization with OVA and CSA-4-1BBL generated a potent in vivo killing response in target cells, and CSA-4-1BBL demonstrated a stronger adjuvant effect than LPS at both concentrations tested.

Example 21

Figure 23:
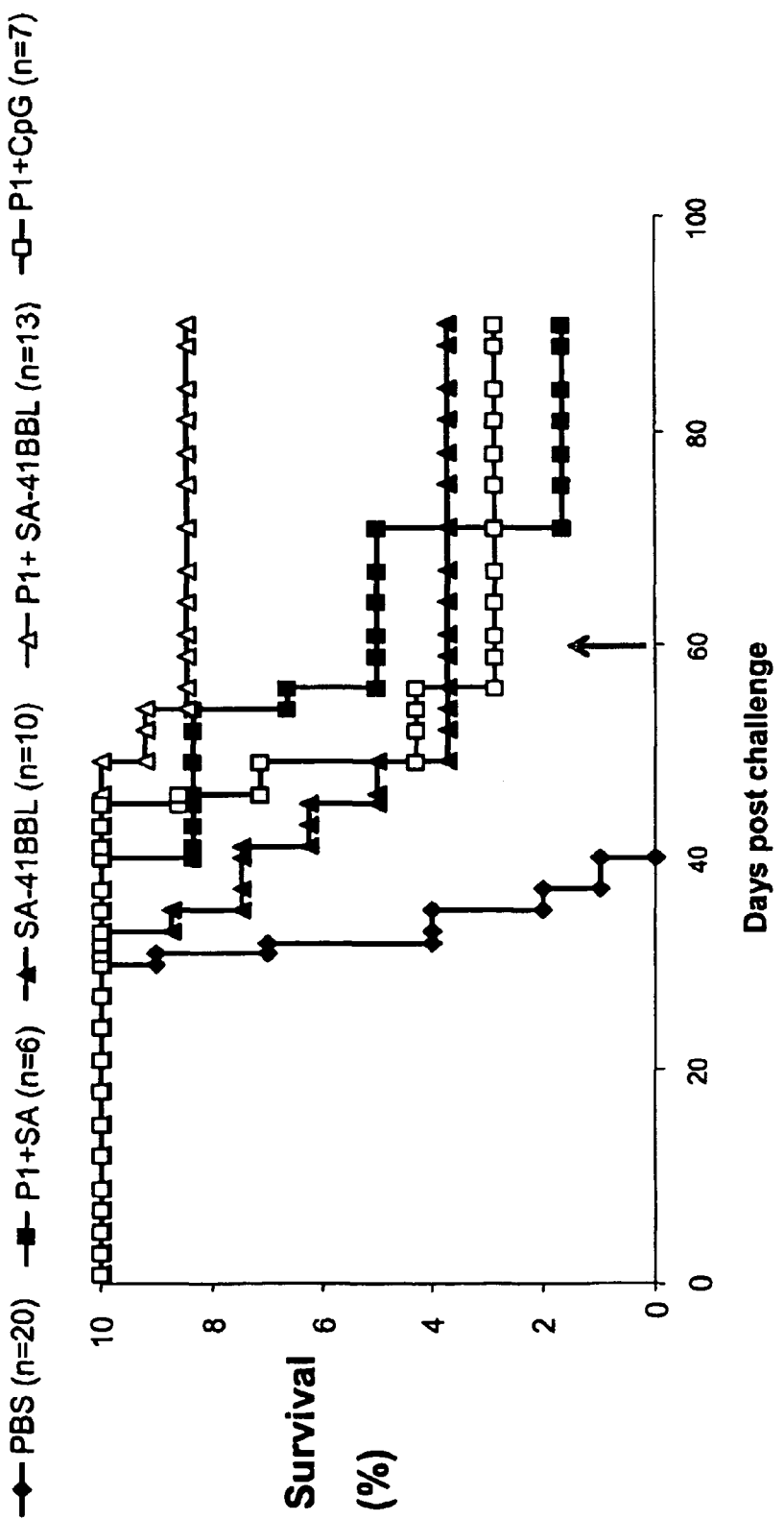
FIG. 23 shows the effects on existing cervical tumors of vaccination with (i) PBS (♦, n=20); (ii) 50 µg P1+12.5 µg CSA (■, n=6) (iii) 25 µg CSA-4-1BBL (▲, n=10); (iv) 50 µg P1+25 µg CSA-4-1BBL (Δ, n=13), or (v) 50 µg P1+10 µg CpG (□, n=7). Vaccination with the combination of P1 and CSA-4-1BBL resulted in significantly enhanced survival rates, while vaccination with either P1 or CSA-4-1BBL provided some successful immunotherapy.

Costimulation with 4-1BBL Greatly Enhanced the Immune Response to HPV16 E7 Protein in Mice, Controlled TC-1 Tumors, and Induced Anti-Tumor Memory Naïve B6 mice were challenged subcutaneously in the right flank with $1 \times 10^5$ live TC-1 cells which stably express the human papillomavirus-16 E7 protein, in a vaccination protocol based on the administration of the CD8+ T cell epitope of the HPV16 E7 epitope P1 (having the amino acid sequence RAHYNIVTF). FIG. 23 shows survival of mice in this TC-1 tumor model. After 10 days, mice received one subcutaneous injection of either (i) PBS (♦, n=20); (ii) 50 μg P1+12.5 μg CSA (■, n=6) (iii) 25 μg CSA-4-1BBL (▲, n=10); (iv) 50 μg P1+25 μg CSA-4-1BBL (Δ, n=13), or (v) 50 μg P1+10 μg CpG (□, n=7).

As shown in FIG. 23, immunization with P1 or CSA-4-1BBL achieved some successful immunotherapy, but better results (including enhanced survival) were achieved by immunization with both P1 and CSA-4-1BBL. All animals receiving only PBS developed tumors.

The surviving animals were re-challenged at day 60 (black arrow). Tumor growth was monitored 3 times a week. Administration of CSA-4-1BBL and P1 together after the tumor challenge significantly increased the survival of animals compared to P1 or CSA-4-1BBL alone, or P1 and CpG. Importantly, none of the surviving animals in the P1+CSA-4-1BBL group developed tumor upon secondary challenge, demonstrating immunological memory.

Example 22

Vaccination with OVA/CSA-4-1BBL Prevents Tumor Growth

Figure 24:
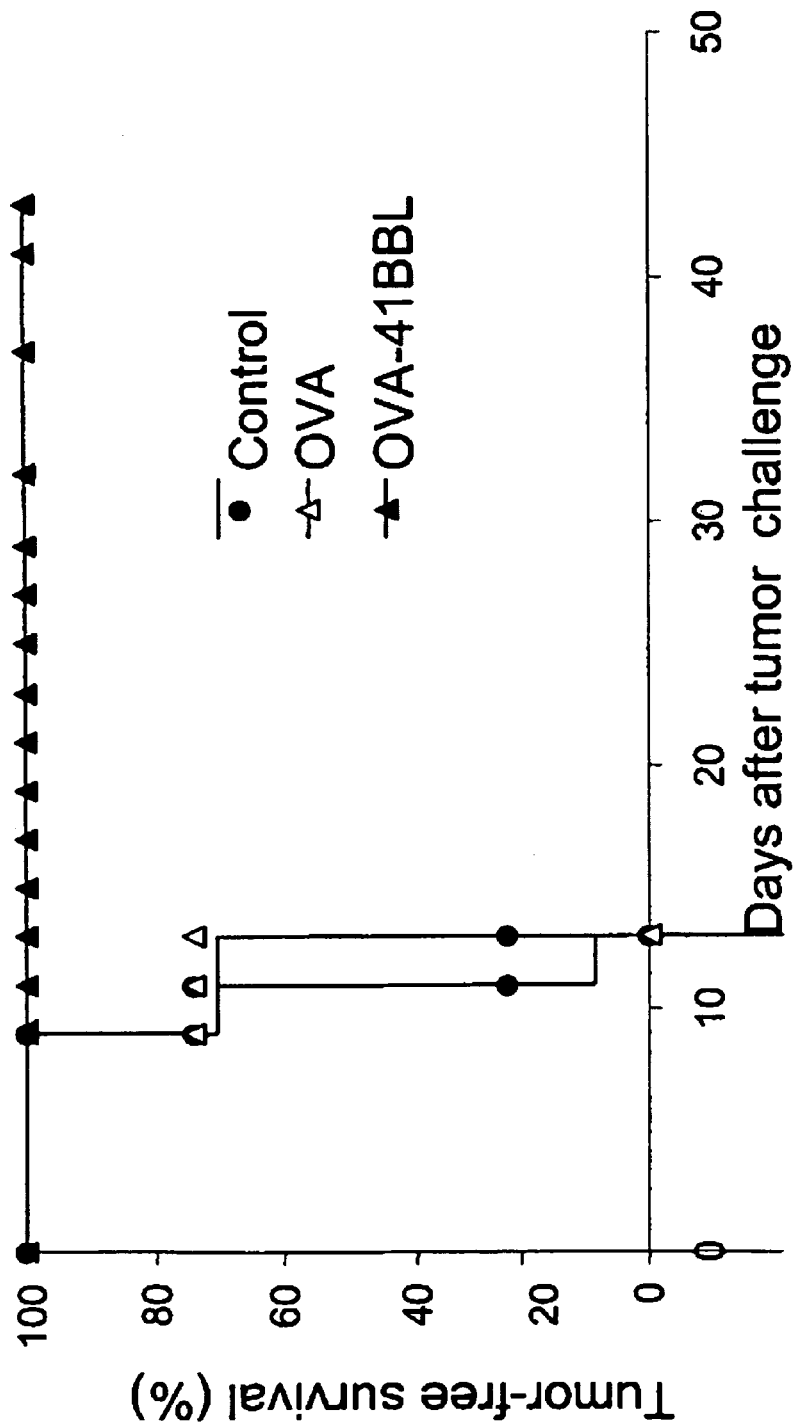
FIG. 24 shows the results of vaccination with a biotinylated OVA/CSA-4-1BBL conjugate in preventing tumor growth. Tumor-free survival of mice vaccinated with OVA (Δ), a biotinylated OVA/CSA-4-1BBL conjugate (▲) and control mice (●) are shown, with mice vaccinated with the biotinylated OVA/CSA-4-1BBL conjugate showing 100% survival.

Naïve C57BL/6 mice were immunized with 50 µg OVA or 50 µg biotinylated OVA conjugated to 25 µg CSA-4-1BBL. Some animals were left untreated as controls. After 7 days, mice were challenged subcutaneously in the right flank with $1 \times 10^5$ OVA-expressing EG.7 tumor cells. Tumor growth was monitored three times a week using calipers. The results (tumor-free survival) are shown in FIG. 24. As shown, all control animals and animals vaccinated with OVA developed tumors, while all animals vaccinated with biotinylated OVA/CSA-4-1BBL did not develop tumors, demonstrating that vaccination with biotinylated OVA/CSA-4-1BBL resulted in 100% prevention of the growth of thyoma tumors.

Example 23

4-1BBL Strongly Enhances the Antigen-Specific CTL Response In Vivo

Figure 25:
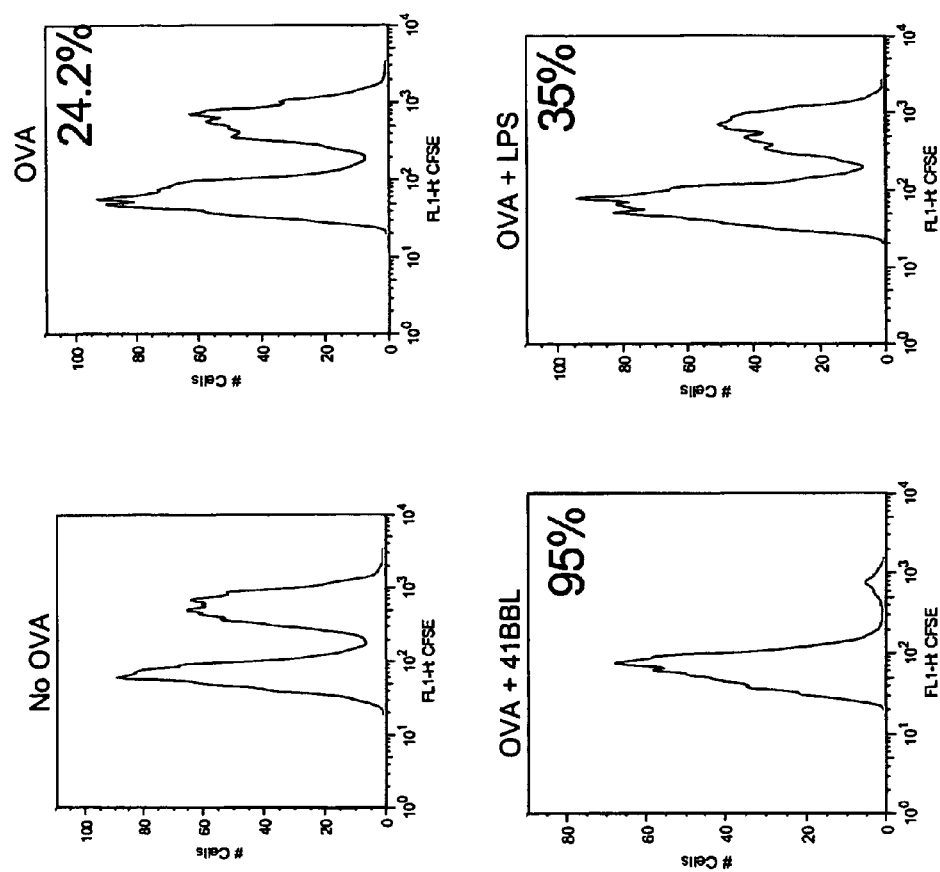
FIG. 25 shows flow cytometry of CFSE stained cells, demonstrating that 4-1BBL could enhance the antigen specific CTL response in vivo to higher levels compared to antigen alone, or antigen and LPS. Results are expressed on the corner of each panel as percentage lysis of the peptide pulsed CFSEhi peak as compared with the reference CFSElow peak normalized to naïve animal.

Naïve C57BL/6 mice were immunized intravenously with (i) 50 µg OVA, (ii) 50 µg OVA and 25 µg CSA-4-1BBL, (iii) 50 µg OVA and 25 µg anti-CD137 antibody or (iv) 50 µg OVA and 25 µg LPS. Naïve animals were used as control. Seven days later, all mice received CFSE labeled target cells. Briefly, splenocytes from naïve C57BL/6 were divided into two population. The first population was labeled with 0.25 µM CFSE (CFSElow). The second population was labeled with 2.5 µM CFSE and then pulsed with 2 µg/ml $OVA_{257-264}$ SIINFEKL peptide for 1 hour (CFSEhi). Cells were mixed at a ratio of 1:1 and a total of $1 \times 10^7$ cells were injected intravenously into recipient animals. Spleens were harvested 48 hours later and CFSE fluorescence intensity was analyzed by flow cytometry, with the results shown in FIG. 25. The results are expressed on the corner of each panel as percentage lysis of the peptide pulsed CFSEhi peak as compared with the reference CFSElow peak normalized to naïve animal. This assay revealed that 4-1BBL could enhance the antigen specific CTL response to higher levels (95%) compared to antigen (OVA) alone (24.2%), or antigen and LPS (35%), resulting in killing of majority of target cells.

Example 24

4-1BBL Costimulation Increases Antigen Presentation to CD8+ T-Cells In Vivo

Figure 26:
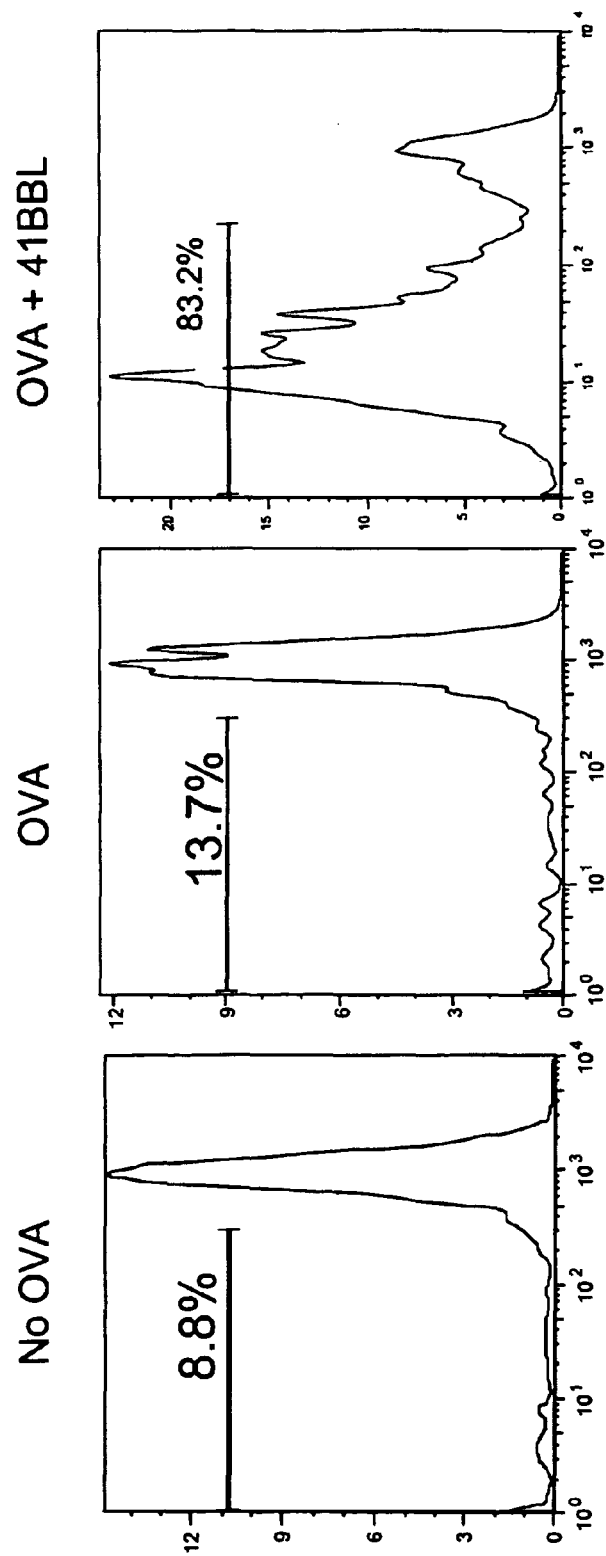
FIG. 26 shows flow cytometry data demonstrating that 4-1BBL costimulation increased antigen presentation in vivo.

Naïve B6-SJL (CD45.1+) animals were immunized intravenously with (i) 10 µg OVA, (ii) 10 µg OVA and 5 µg 4-1BBL, or (iii) left untreated. After 2 days, animals received $1 \times 106$ CFSE labeled OT-1 cells (CD45.2+) by intravenous injection. Spleen were harvested 3 days later and proliferation of OT-1 cells were analyzed using flow cytometry, as shows in FIG. 26. Administration of 4-1 BBL together with the antigen increased the antigen presentation to CD8+ T cells as demonstrated by proliferation of majority of OT-1 cells. (83.2% for OVA+4-1BBL; 13.7% for OVA; 8.8% for no treatment).

Example 25

4-1BBL Costimulation Increases Antigen Uptake by Dendritic Cells

Figure 27:
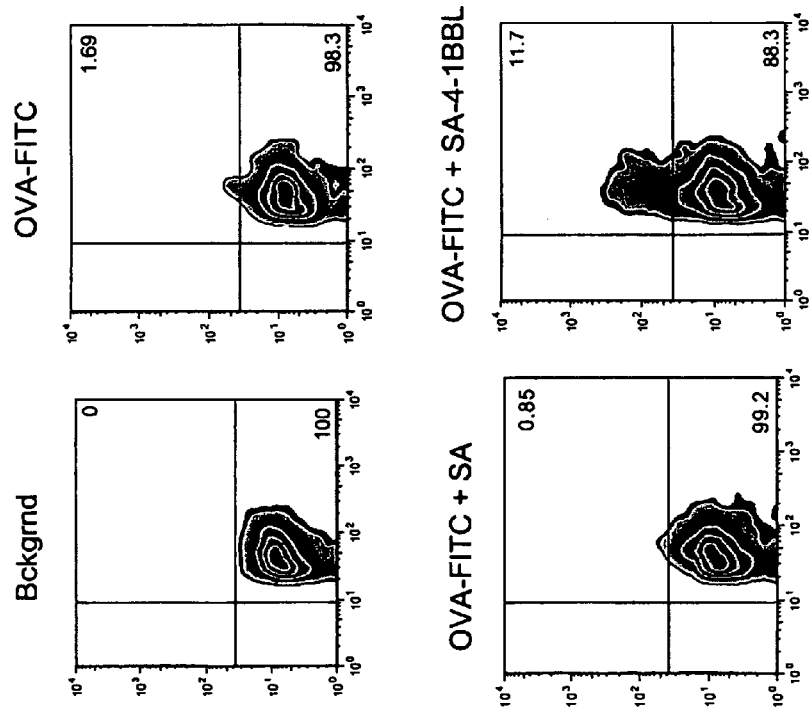
FIG. 27 shows flow cytometry data demonstrating that 4-1BBL costimulation increases antigen uptake by dendritic cells in vivo.

Naïve BALB/c mice were injected subcutaneously with 25 µg OVA-FITC, 25 µg OVA-FITC and 10 µg CSA, or 25 µg OVA-FITC and 25 µg CSA-4-1BBL. After 3 hours, inguinal lymph nodes at the site of injection were harvested. FITC+ cells in CD11c+ population was analyzed using flow cytometry to determine in vivo fluorescently-labelled antigen update, as seen in FIG. 27. As shown, 4-1BBL signaling increased the antigen uptake by CD11c+ DCs whereas the control CSA protein had no effect.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other exemplary embodiments are set forth below and in the claims that follow.

What is claimed is:

1. A combination comprising: (a) a conjugate comprising a 4-1BBL immune co-stimulatory polypeptide and avidin or streptavidin; and (b) an antigen associated with an infectious agent.

2. The combination of claim 1, wherein said antigen is bound to said 4-1BBL conjugate.

3. The combination of claim 1, wherein said antigen is conjugated to a biotin moiety, to form an antigen-biotin conjugate.

4. The combination of claim 3, wherein said antigen-biotin conjugate is bound to said 4-1BBL conjugate via said biotin moiety.

5. The combination of claim 1, wherein said antigen is not bound to said 4-1BBL conjugate.

6. The combination of claim 1, wherein said infectious agent is a bacteria.

7. The combination of claim 6, wherein said bacteria is selected from the group consisting of *Mycobacterium tuberculosis, Bacillus anthracis,* and *Staphylococcus aureus.*

8. The combination of claim 1, wherein said infectious agent is a virus.

9. The combination of claim 8, wherein said virus is selected from the group consisting of *Adenoviridae, Arenaviridae Caliciviridae, Coronaviridae, Filoviridae, Fla-*

*viviridae, Hepadnaviridae, Herpesviridae, Orthomyxoviridae, Papillomaviridae, Picornaviridae, Poxyiridae, Reoviridae, Retroviridae, Rhabdoviridae*, and *Togaviridae*.

10. The combination of claim 1, wherein said infectious agent is a parasite.

11. The combination of claim 10, wherein said parasite is selected from the group consisting of *Plasmodium* and *Leishmania*.

12. The combination of claim 1, wherein said infectious agent is a fungus.

13. The combination of claim 12, wherein said fungus is selected from the group consisting of *Aspergillis, Candida, Coccidia, Cryptococci, Geotricha, Histoplasma, Microsporidia*, and *Pneumocystis*.

14. The combination of claim 1, further comprising a pharmaceutically acceptable excipient.

15. The combination of claim 1, wherein said 4-1BBL conjugate is provided in a container that also contains said antigen.

16. The combination of claim 1, wherein said 4-1BBL conjugate is provided in a separate container from said antigen.

17. The combination of claim 1, wherein said conjugate comprises the amino acid sequence of SEQ ID NO: 8.

* * * * *